US010273497B2

(12) United States Patent
Riechmann et al.

(10) Patent No.: US 10,273,497 B2
(45) Date of Patent: Apr. 30, 2019

(54) PLANT TOLERANCE TO LOW WATER, LOW NITROGEN AND COLD II

(71) Applicants: Mendel Biotechnology, Inc., Hayward, CA (US); Monsanto Technology LLC, St. Louis, MO (US)

(72) Inventors: Jose Luis Riechmann, Barcelona (ES); Oliver J. Ratcliffe, Oakland, CA (US); T. Lynne Reuber, San Mateo, CA (US); Katherine Krolikowski, Oakland, CA (US); Jacqueline E. Heard, Wenham, MA (US); Omaira Pineda, Vero Beach, FL (US); Cai-Zhong Jiang, Davis, CA (US); Robert A. Creelman, Castro Valley, CA (US); Roderick W. Kumimoto, Sacramento, CA (US); Paul S. Chomet, Mystic, CT (US)

(73) Assignees: Mendel Biotechnology, Inc., Hayward, CA (US); Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/713,497

(22) Filed: Sep. 22, 2017

(65) Prior Publication Data
US 2018/0087062 A1    Mar. 29, 2018

Related U.S. Application Data

(60) Division of application No. 14/666,086, filed on Mar. 23, 2015, now Pat. No. 9,783,819, which is a continuation of application No. 13/232,907, filed on Sep. 14, 2011, which is a division of application No. 11/981,667, filed on Mar. 7, 2008, now Pat. No. 8,022,274.

(60) Provisional application No. 60/961,403, filed on Jul. 20, 2007.

(51) Int. Cl.
C12N 15/82 (2006.01)
C07K 14/415 (2006.01)

(52) U.S. Cl.
CPC .......... *C12N 15/827* (2013.01); *C07K 14/415* (2013.01); *C12N 15/8271* (2013.01); *C12N 15/8273* (2013.01)

(58) Field of Classification Search
None
See application file for complete search history.

(56) References Cited

U.S. PATENT DOCUMENTS

| 5,859,326 A | 1/1999 | An |
|---|---|---|
| 2003/0121070 A1 | 6/2003 | Adam et al. |
| 2004/0034888 A1* | 2/2004 | Liu .................. C07H 21/04 800/289 |
| 2007/0061911 A9 | 3/2007 | Zhang et al. |
| 2008/0313756 A1* | 12/2008 | Zhang ............. C07K 14/415 800/260 |
| 2009/0044297 A1 | 2/2009 | Andersen et al. |
| 2009/0049566 A1 | 2/2009 | Zhang et al. |
| 2009/0138981 A1 | 5/2009 | Repetti et al. |

OTHER PUBLICATIONS

Wells, Biochemistry 29:8509-8517, 1990.*
Ngo et al., (The Protein Folding Problem and Tertiary Structure Prediction, K. Merz., and S. Le Grand (eds.) pp. 492-495, 1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Doerks et al., (TIG, 14:248-250, 1998).*
Smith et al. (Nature Biotechnology, 15:1222-1223, 1997).*
Bork et al. (TIG, 12:425-427, 1996).*
Yang et al. (PNAS, 98:11438-11443, 2001 ).*
NCBI Accession No. XP_003544838 (GI:356552982) (Nov. 8, 2011); "Predicted: MADS-box transcription factor 27-like [Glycine max]".
NCBI Accession No. NP_179848 (GI:15227254) (Aug. 13, 2001); Lin, X., et al.; "putative MADS-box protein AGL17 [*Arabidopsis thaliana*]".
NCBI Accession No. NP_179033 (GI:15225607) (Aug. 13, 2001); Lin, X., et al.; "putative MADS-box protein [*Arabidopsis thaliana*]".
NCBI Accession No. NP_195507 (GI:15235748) (Aug. 13, 2001); Mayer, K., et al.; "MADS-box protein AGL17-like protein [*Arabidopsis thaliana*]".
NCBI Accession No. CAD40988 (GI:38344968) (Nov. 14, 2003); Feng, Q., et al.; "OSJNBa0072F16.13 [*Oryza sativa* (japonica cultivar-group)]".
NCBI Accession No. NP_001047230 (GI: 115446901) (Oct. 2, 2006); Ohyanagi, H., et al.; "Os02g0579600 [*Oryza sativa* (japonica cultivar-group)]".
NCBI Accession No. NP_001048018 (GI:115448477) (Oct. 2, 2006); Ohyanagi, H., et al.; "Os02g0731200 [*Oryza sativa* (japonica cultivar-group)]".
NCBI Accession No. BAC99345 (GI: 37805928) (Oct. 22, 2003); Sasaki, T., et al.; "putative transcription factor MADS23 [*Oryza sativa* (japonica cultivar-group)]".
NCBI Accession No. NP_001241489 (GI:359806370) (Dec. 10, 2011); "uncharacterized protein LOC100805092 [Glycine max]".

(Continued)

*Primary Examiner* — Vinod Kumar
(74) *Attorney, Agent, or Firm* — Dentons US LLP

(57) ABSTRACT

Polynucleotides incorporated into nucleic acid constructs have been introduced into plants and were ectopically expressed. The encoded polypeptides of the invention have been shown to confer at least one regulatory activity and confer earlier flowering, longer floral organ retention, increased cold tolerance, greater tolerance to water deprivation, altered carbon-nitrogen balance sensing, increased low nitrogen tolerance, and/or increased tolerance to hyperosmotic stress as compared to a control plant.

13 Claims, 10 Drawing Sheets

Figure 1:
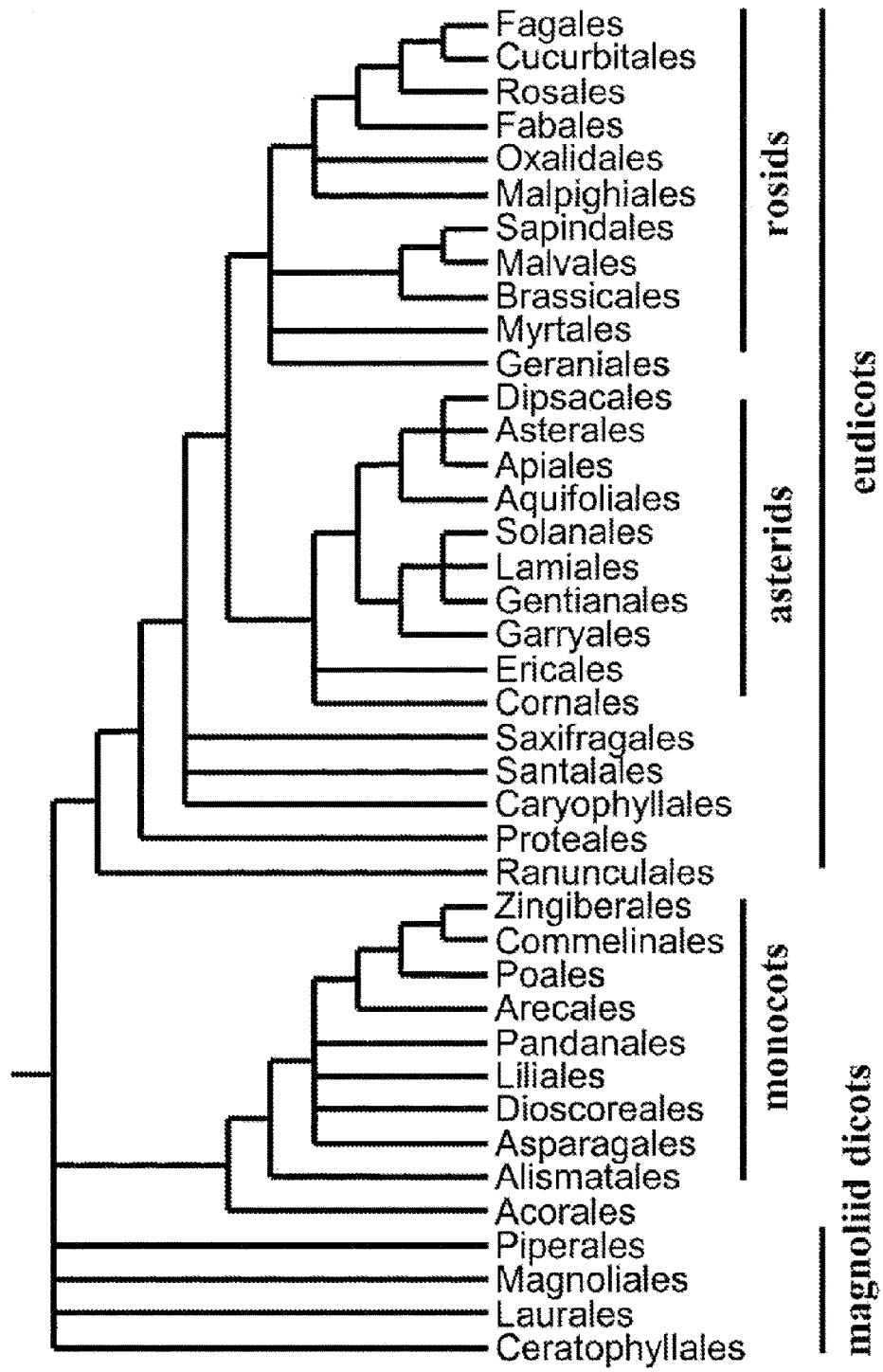

Specification includes a Sequence Listing.

(56) References Cited

OTHER PUBLICATIONS

NCBI Accession No. XP_003518271 (GI:356498871) (Nov. 8, 2011); "Predicted: MADS-box transcription factor 27-like [Glycine max]".
NCBI Accession No. XP_004973502 (GI:514796247) (Jun. 26, 2013); "Predicted: MADS-box transcription factor 27-like [Setaria italica]".
NCBI Accession No. XP_004975863 (GI:514801929) (Jun. 26, 2013); "Predicted: MADS-box transcription factor 27-like [Setaria italica]".
NCBI Accession No. AAG09919 (GI:9964296) (Sep. 2, 2000); Heuer, S., et al.; "MADS box protein 2 [Zea mays]".
NCBI Accession No. GI:1816459 (GenBank: CAA71739.1) (Feb. 3, 1997); Zachgo, S., et al.; "DEFH125 protein [Antirrhinum majus]".
NCBI Accession No. NP_191282 (GI:30694601) (May 13, 2003); Haas, B. J.; "MADS-box protein [*Arabidopsis thaliana*]".
Bork et al., "Go hunting in sequence databases but watch out for the traps," *TIG* 12:425-427, 1996.
Guo et al., "Protein tolerance to random amino acid change," *PNAS* 101:9205-9210, 2004.
Keskin et al., "A new, structurally nonredundant, diverse data set of protein-protein interfaces and its implications," *Protein Science* 13:1043-1055, 2004.
Ngo et al., "Computational Complexity, Protein Structure Prediction, and the Levinthal Paradox," In: The Protein Folding Problem and Tertiary Structure Prediction, K. Merz., and S. Le Grand (eds.), pp. 492-495, 1994.
Smith et al., "The challenges of genome sequence annotation or 'The devil is in the details'," *Nature Biotechnology* 15:1222-1223, 1997.
Thornton et al., "From structure to function: Approaches and limitations," *Nature Structural Biology; Structural Genomics Supplement*, Nov. 2000.
Yang et al., "Expression of the REB transcriptional activator in rice grains improves the yield of recombinant proteins whose genes are controlled by a *Reb*-responsive promoter," *PNAS* 98:11438-11443, 2001.
Wells, "Additivity of Mutational Effects in Proteins," *Biochemistry* 29:8509-8517, 1990.
Doerks et al., "Protein annotation: detective work for function prediction," *TIG* 14:248-250, 1998.
NCBI Accession No. (AL035538) (Feb. 26, 1999); *Arabidopsis thaliana* DNA chromosome 4, BAC clone F20D10 (ESSA project).

\* cited by examiner

```
                          <---------------- MADS DNA binding domain ---------------->
G152   (4)   MGRGKIVIQKIDDSTSRQVTFSKRRKGLIKKAKELAILCDAEVCLIIFSNTDKLYDFA
G1760  (2)   MGRGKIVIQRIDDSTSRQVTFSKRRKGLIKKAKELAILCDAEVGLIIFSSTGKLYDFA
G860   (16)  MGRGKIAIKRINNSTSRQVTFSKRRNGLLKKAKELAILCDAEVGVIIFSSTGRLYDFS
G153   (14)  MGRGKIVIRRIDNSTSRQVTFSKRRSGLLKKAKELSILCDAEVGVIIFSSTGKLYDYA
G3980  (10)  MGRGKIVIRRIDNSTSRQVTFSKRRNGLLKKAKELAILCDAEVGVMIFSSTGKLYDFA <-- I nuclear localization domain -->  <-- K protein interaction domain
G152   (4)   S-SSVKSTIERFNTAKMEEQELMNPASEVKFWQREAETLRQELHSLQENYR-QLTGVE
G1760  (2)   S-SSMKSVIDRYNKSKIEQQQLLNPASEVKFWQREAAVLRQELHALQENHR-QMMGEQ
G860   (16)  S-SSMKSVIERYSDAKGETSSENDPASEIQFWQKEAAILKRQLHNLQENHR-QMMGEE
G153   (14)  SNSSMKTIIERYNRVKEEQHQLLNHASEIKFWQREVASLQQQLQYLQECHR-KLVGEE
G3980  (10)  S-SSMKSVMDRYSKSKEEPCQLGSSASEIKFWQREAAMLRQQLHNLQESHRRKMMGEE -------- K protein interaction domain --------      Activation domain
G152   (4)   LNGLSVKELQNIESQLEMSLRGIRMKREQILTNEIKELTRKRNLVHHENLELSRKVQR
G1760  (2)   LNGLSVNELNSLENQIEISLRGIRMRKEQLLTQEIQELSQKRNLIHQENLDLSRKVQR
G860   (16)  LSGLSVEALQNLENQLELSLRGVRMKKDQMLIEEIQVLNREGNLVHQENLDLHKKVNL
G153   (14)  LSGMNANDLQNLEDQLVTSLKGVRLKKDQLMTNEIRELNRKGQIIQKENHELQNIVDI
G3980  (10)  LSGLTVKELQNLENQLEISLHGVRMKKDQLLMGEIQELNRKGNLIHQENVELYKKVYG Activation domain
G152   (4)   IHQENVELYK------KAYGTSNTNGLGHHELVDAVYESHAQVRLQLSQP--EQSHYK
G1760  (2)   IHQENVELYK------KAY-MANTNGFTHREVAVADDESHTQIRLQLSQP--EHSDYD
G860   (16)  MHQQNMELHEKV-SEVEGVKIANKNSLLTNGLDMR-DTSNEHVHLQLSQPQHDHETHS
G153   (14)  MRKENIKLQKK----VHGRTNAIEGNSSVDPISNG-TTTYAPPQLQLIQLQPAPREKS
G3980  (10)  TQDDN-----------E----TNRDSVLTNGLGIG-EDLQVPVNLQLSQPQQQQQHYK G152   (4)   TSSNS
G1760  (2)   TPPRANE
G860   (16)  KAIQLNYFSFIA
G153   (14)  IRLGLQLS
G3980  (10)  ASSGTTKLGLQLH
```

Fig. 4

```
G152   (4)   MGRGKIVIQKIDDSTSRQVTFSKRRKGLIKKAKELAILCDAEVCLIIFSNTDKLYDFAS-
G1760  (2)   MGRGKIVIQRIDDSTSRQVTFSKRRKGLIKKAKELAILCDAEVGLIIFSSTGKLYDFAS-
G3980  (10)  MGRGKIVIRRIDNSTSRQVTFSKRRNGLLKKAKELAILCDAEVGVMIFSSTGKLYDFAS-
G3981  (12)  MGRGKIVIRRIDNSTSRQVTFSKRRNGLLKKAKELAILCDAEVGVMIFSSTGKLYDFAS-
G3485  (8)   MGRGKIVIRRIDNSTSRQVTFSKRRNGLLKKAKELAILCDAEVGVMIFSSTGKLYDFAS-
G860   (16)  MGRGKIAIKRINNSTSRQVTFSKRRNGLLKKAKELAILCDAEVGVIIFSSTGRLYDFSS-
G3982  (6)   MGRGKIVIQRIDKSTSRQVTFSKRRSGLLKKAKELAILCDAEVGVVIFSSTGKLYEFSS-
G3479  (18)  MGRGKIVIRRIDNSTSRQVTFSKRRNGIFKKAKELAILCDAEVGLVIFSSTGRLYEYAS-
G3488  (30)  MGRGKIVIRRIDNSTSRQVTFSKRRNGIFKKARELAILCDAEVGLVIFSSTGRLYEYAS-
G3480  (20)  MGRGKIVIRRIDNSTSRQVTFSKRRNGIFKKAKELAILCDAEVGLMIFSSTGRLYEYSS-
G3489  (24)  MGRGKIVIRRIDNSTSRQVTFSKRRNGIFKKAKELAILCDAEVGLVIFSSTGRLYEYSS-
G3481  (22)  MGRGKIVIRRIDNSTSRQVTFSKRRNGLLKKAKELSILCDAEVGLVVFSSTGRLYEFSS-
G153   (14)  MGRGKIVIRRIDNSTSRQVTFSKRRSGLLKKAKELSILCDAEVGVIIFSSTGKLYDYASN
G3484  (26)  MGRGKIAIRRIDNSTSRQVTFSKRRNGLLKKARELSILCDAEVGLMVFSSTGKLYDYAS-
G3483  (32)  MGRGKIEIKRIDNATSRQVTFSKRRSGLFKKARELSILCDAEVGLLVFSSTSRLYDFAS-
G3487  (28)  MGRGKIEIKRIDNATSRQVTFSKRRGGLFKKAKELAILCDAEVGLVVFSSTGRLYHFAS-
```

Fig. 5A

```
G152   (4)   SSVKSTIERFNTAKMEEQELMNPASEVKFWQREAETLRQELHSLQENYR-QLTGVELNGL
G1760  (2)   SSMKSVIDRYNKSKIEQQQLLNPASEVKFWQREAAVLRQELHALQENHR-QMMGEQLNGL
G3980  (10)  SSMKSVMDRYSKSKEEPCQLGSSASEIKFWQREAAMLRQQLHNLQESHRRKMMGEELSGL
G3981  (12)  SSMKSVMDRYSKSKEEPCQLGSSASEIKFWQREAAMLRQQLHNLQESHR-KMMGEELSGL
G3485  (8)   SSMKSVMDRYSKSKEEPCQLGSSASEIKFWQREAAMLRQQLHNLQESHRRKMMGEELSGL
G860   (16)  SSMKSVIERYSDAKGETSSENDPASEIQFWQKEAAILKRQLHNLQENHR-QMMGEELSGL
G3982  (6)   TSMKSIIERHTKTKEDHHQLLNHGSEVKFWQREAATLRQQLQDLQENHR-KLMGEELQGL
G3479  (18)  TSMKSVIDRYGRAKEEQQHVANPNSELKFWQREAASLRQQLHSLQENHR-QLMGQDLSGL
G3488  (30)  TSIKSVIDRYGRAKEEE-HVADPNTELKFWQREAASLRQQLHNLQENHRRQLMGQNLSGL
G3480  (20)  TSMKSVIDRYGKSKDEQQAVANPNSELKFWQREAASLRQQLHNLQENHR-QLMGEDLSGL
G3489  (24)  TSMKSVIDRYGKAKEEQQVVANPNSELKFWQREAASLRQQLHNLQENYR-QLTGDDLSGL
G3481  (22)  TNMKTVIDRYTNAKEEL-LGGNATSEIKIWQREAASLRQQLHNLQESHK-QLMGEELSGL
G153   (14)  SSMKTIIERYNRVKEEQHQLLNHASEIKFWQREVASLQQQLQYLQECHR-KLVGEELSGM
G3484  (26)  TSMKAVIERYNKLKEETHHLMNPASEEKFWQTEAASLRQQLQYLQECHR-QLMGEELTGL
G3483  (32)  SSMKSIIERYNETKEDPHQTMNASSEAKEY-------------MSSDLF-KVVKVGIS-V
G3487  (28)  TSMESVIERYEE-REGHHQTMSASAEAKLWQREAGSLRQQLHNLQEHHR-KLLGQQLSGL
```

Fig. 5B

```
G152   (4)   SVKELQNIESQLEMSLRGIRMKREQILTNEIKELTRKRNLVHHENLELSRKVQRIHQENV
G1760  (2)   SVNELNSLENQIEISLRGIRMRKEQLLTQEIQELSQKRNLIHQENLDLSRKVQRIHQENV
G3980  (10)  TVKELQNLENQLEISLHGVRMKKDQLLMGEIQELNRKGNLIHQENVELYKKVYGTQDDNE
G3981  (12)  TVKELQNLENQLEISLRGVRMKKDQLLMDEIQELNRKGNLIHQENVELYQKVYGTKDDNK
G3485  (8)   TVKELPNLENQLEISLHGVRMKKDQLLMGEIQELNRKGNLIHQENVELYKKVYGTQDDNE
G860   (16)  SVEALQNLENQLELSLRGVRMKKDQMLIEEIQVLNREGNLVHQENLDLHKKVNLMHQQNM
G3982  (6)   NVEDLHRLENQLEMSLRGVRMKKVQMLTDEVHELRRKGHLIHQENNELYEKVKLLQQENK
G3479  (18)  GVKELQTLENQLEMSIRCIRTKKDQLMIDEIHELNRKGSLIHQENMELYRKVNLIRQENA
G3488  (30)  GVKGLQNLENQLEMSICCIRTKKDQLLVDEIHELNRKGSLIQQDNMGLHRKVNLIRQENA
G3480  (20)  NVKELQSLENQLEISLRSVRTKKDHVLIDEIHELNRKGSLVHQENMELYKKISLIRQENA
G3489  (24)  NVKELQSLENQLETSLRGVRAKKDHLLIDEIHDLNRKASLFHQENTDLYNKINLIRQEND
G3481  (22)  GVRDLQGLENRLEISLRNIRMRKDNLLKSEIEELHVKGSLIHQENIELSRSLNVMSQQKL
G153   (14)  NANDLQNLEDQLVTSLKGVRLKKDQLMTNEIRELNRKGQIIQKENHELQNIVDIMRKENI
G3484  (26)  GIKELQNLENQLEMSLKGVRMKKDQILTNEIKELRQKGNIIHQENVELYQKMEQIQKENA
G3483  (32)  DSRYLY------------------CIIFHQA-----------------------------
G3487  (28)  DVRDLQNLENQLETSLRNIRLKMDQLIFYQIQELNRKGYLMHQENIELHNKVNLLHQENI
```

Fig. 5C

```
G152    (4)  ELYKKAYG--------TSNTNGLGHHELVDAVYESHAQVRLQLSQPEQ-----SHYKTSS-
G1760   (2)  ELYKKAY---------MANTNGFTHREVAVADDESHTQIRLQLSQPEH-----SDYDTPP-
G3980  (10)  ----------------TNRDSVLTNGLGIG-EDLQVPVNLQLSQPQQQQ---QHYKASS-
G3981  (12)  ----------------TNRDSVLTNGLGIG-EDLQVPVNLQLSQPQQ-----QHYKEPS-
G3485   (8)  ----------------TNRDSVLTNGLGIG-EDLQVPVNLQLSQPSTSNNTTRHLQELQK
G860   (16)  ELHEKVSEVE--GVKIANKNSLLTNGLDMR-DTSNEHVHLQLSQPQH-----DHETHSK-
G3982   (6)  ELCKKAYGTR--DVSAANGTALVPFGFAIG-REQFEPIQLHLSQPEP-----ENIETSR-
G3479  (18)  ELYKKLYETG--AENEANRDSTTPYNFAVI-EEANTPARLELNPPSQ----QNDAEQTT-
G3488  (30)  ELYKKLYEKE--AEGEVNRDSTTPYNFVVA-EGANVPIHLELNIPLQ----ENGVEQPV-
G3480  (20)  ELYKKIYETE--GPSEVNRDSPTPYNFAVI-EKTNVPVQLGLSTLPQ----HSDAEQST-
G3489  (24)  ELHKKIYETE--GPSGVNRESPTPFNFAVV-ETRDVPVQLELSTLPQ----QNNIEPST-
G3481  (22)  ELYNKLQACEQRGATDANESSSTPYSFRII-QNANMPPSLELSQSQQR---EGECSKTA-
G153   (14)  KLQKKVHGRT--NAIEGNSSVDP---ISNG-TTTYAPPQLQLIQLQP-----APREKSI-
G3484  (26)  ELQKKVYEAR--STNEENVASNPSYNVRNG-YDSLASISLQLSQPQSQYKYSEPSTKAM-
G3483  (32)  ------------------------------------------------------------
G3487  (28)  KLRRKAYGQG----VNEHPTSTTVRHSILNTENEDVRINLELSVQRD------KSETPS-
```

Fig. 5D

```
G152    (4)  --------------------NS----------------------------------
G1760   (2)  --------------------RANE--------------------------------
G3980  (10)  ------------------GTTKLGLQLH----------------------------
G3981  (12)  ------------------GTTKLGLQLH----------------------------
G3485   (8)  WADCNCIDPYTGCVCFTIAIKKNGLRFKPRCLRINVVAYRPQTNWLKDFNLKLSEKEKAT
G860   (16)  ------------------AIQLNYFSFIA---------------------------
G3982   (6)  --------------------ASGSK------------------------------
G3479  (18)  --------------------PPKLG------------------------------
G3488  (30)  ------------------APKLGLQLNQ---------------------------
G3480  (20)  ------------------APKLGLQLNP---------------------------
G3489  (24)  ------------------APKLGLQLIP---------------------------
G3481  (22)  ------------------APELGLHLP----------------------------
G153   (14)  --------------------RLGLQLS----------------------------
G3484  (26)  --------------------KLGLQLH----------------------------
G3483  (32)  --------------------------------------------------------
G3487  (28)  --------------------VG----------------------------------
```

Fig. 5E

```
G152   (4)  ----
G1760  (2)  ----
G3980  (10) ----
G3981  (12) ----
G3485  (8)  LACM
G860   (16) ----
G3982  (6)  ----
G3479  (18) ----
G3488  (30) ----
G3480  (20) ----
G3489  (24) ----
G3481  (22) ----
G153   (14) ----
G3484  (26) ----
G3483  (32) ----
G3487  (28) ----
```

Fig. 5F

PLANT TOLERANCE TO LOW WATER, LOW NITROGEN AND COLD II

RELATIONSHIP TO COPENDING APPLICATIONS

This application is a division of U.S. non-provisional application Ser. No. 14/666,086, filed Mar. 23, 2015, which application is a continuation of U.S. non-provisional application Ser. No. 13/232,907, filed Sep. 14, 2011 (abandoned), which application is a division of U.S. non-provisional application Ser. No. 11/981,667, filed Mar. 7, 2008 (now U.S. Pat. No. 8,022,274), which claims the benefit of U.S. provisional application 60/961,403, filed Jul. 20, 2007. The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION

The present invention relates to plant genomics and plant improvement, increasing a plant's water use efficiency and abiotic stress tolerance, and the yield that may be obtained from a plant.

BACKGROUND OF THE INVENTION

The Effects of Various Factors on Plant Yield.

Yield of commercially valuable species in the natural environment may be suboptimal as plants often grow under unfavorable conditions, such as at an inappropriate temperature or with a limited supply of soil nutrients, light, or water availability. Various factors that may affect yield, crop quality, appearance, or overall plant health include:

Nutrient Limitation

Nitrogen (N) and phosphorus (P) are critical limiting nutrients for plants. Phosphorus is second only to nitrogen in its importance as a macronutrient for plant growth and to its impact on crop yield.

Nitrogen and carbon metabolism are tightly linked in almost every biochemical pathway in the plant. Carbon metabolites regulate genes involved in nitrogen acquisition and metabolism, and are known to affect germination and the expression of photosynthetic genes (Coruzzi et al., 2001) and hence growth. Gene regulation by C/N (carbon-nitrogen balance) status has been demonstrated for a number of nitrogen-metabolic genes (Stitt, 1999); Coruzzi et al., 2001). A plant with altered C/N sensing may exhibit improved germination and/or growth under nitrogen-limiting conditions.

Increased tolerance to abiotic stresses, such as water deprivation, salt, freezing and other hyperosmotic stresses, and cold, and heat, may improve germination, early establishment of developing seedlings, and plant development.

In water-limited environments, crop yield is a function of water use, water use efficiency (WUE; defined as aerial biomass yield/water use) and the harvest index (HI; the ratio of yield biomass to the total cumulative biomass at harvest). WUE is a complex trait that involves water and $CO_2$ uptake, transport and exchange at the leaf surface (transpiration). Improved WUE has been proposed as a criterion for yield improvement under drought. Water deficit can also have adverse effects in the form of increased susceptibility to disease and pests, reduced plant growth and reproductive failure. Genes that improve WUE and tolerance to water deficit thus promote plant growth, fertility, and disease resistance. Enhanced tolerance to these stresses would lead to yield increases in conventional varieties and reduce yield variation in hybrid varieties. Altering the timing of flowering can also enhance the ability to a plant to maintain yield under water limited conditions. For example, acceleration of flowering and maturation may allow a plant to set seed earlier in the growing season and thereby avoid severe water limitation which occurs late in the season.

Plant pathogen injury may affect any part of a plant, and include defoliation, chlorosis, stunting, lesions, loss of photosynthesis, distortions, necrosis, and death. All of these symptoms ultimately result in yield loss in commercially valuable species.

Fortunately, a plant's traits, including its biochemical, developmental, or phenotypic characteristics that enhance yield or tolerance to various abiotic or biotic stresses, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties. We have identified polynucleotides encoding transcription factors, including G1760 and closely-related sequences, developed numerous transformed or transgenic plant lines using these polynucleotides, and analyzed the plants for improved traits, such as altered C/N sensing, water or nutrient use efficiency, tolerance to abiotic stresses, such as water deprivation, cold, heat, low nitrogen conditions, and/or resistance to disease. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The invention is directed to transformed seed produced by any of the transformed or transgenic plants of the invention, wherein the transformed seed comprises a transcription factor sequence of the invention. The presently disclosed subject matter also provides methods for producing a transformed plant seed. In some embodiments, the method comprises (a) transforming a plant cell with a nucleic acid construct (for example, an expression vector, an expression cassette, or a DNA preparation) comprising a polynucleotide sequence encoding or targeting a transcription factor polypeptide of the invention, or a fragment or derivative thereof; (b) regenerating a plant from the transformed plant cell; and (c) isolating a transformed seed from the regenerated plant. In some embodiments, the seed may be grown into a plant that has greater tolerance to cold, water deficit, hyperosmotic stress, or low nitrogen conditions than a control plant, for example, a non-transformed plant of the same species, or a non-transformed parental line, or a wild-type plant of the same species. The transformed plant may be a eudicot or dicot plant. The polynucleotide sequence may be derived from a eudicot or dicot plant, such as, for example, soy, rice, maize, *Antirrhinum*, or *Arabidopsis*.

The invention also pertains to an expression vector that comprises a recombinant nucleic acid sequence of the invention, such as any of SEQ ID NO: 1, 3, 5, 7, 9, 11, 13, 15, 17, 19, 21, 23, 25, 27, 29 or 31, or a sequence that is homologous to any of these sequences, or a sequence that hybridizes to any of these sequences under stringent conditions. The recombinant nucleic acid sequence encodes a polypeptide. The polypeptide shares an amino acid identity with any of SEQ ID NO: 2, 4, 6, 8, 10, 12, 14, 16, 18, 20, 22, 24, 26, 28, 30, 32, 33, 34, 35, 36, 37, 38, 39, 40, 41, 42, 43, 44, 45, 46, 47, or 48, wherein the percent amino acid identity is selected from the group consisting of at least about 55%. The recombinant nucleic acid sequence may specifically hybridize to the complement of the sequence set forth in SEQ ID NO: 1, 3, 5, 7, 9, 11, 13, 15, 17, 19, 21, 23, 25, 27, 29, or 31 under stringent conditions comprising two wash steps at least as stringent as 6×SSC at 65° C. of 10-30 minutes for each wash step (greater stringency may be achieved by, for example, two wash steps of 0.5×SSC, 0.1% SDS at 65° C., or 0.2×SSC, 0.1% SDS at 65° C.). When the polypeptide is overexpressed in a plant, the polypeptide regulates transcription and confers at least one regulatory activity resulting in an altered trait in the plant as compared to a control plant. The altered trait may be, for example, increased tolerance to low nitrogen conditions, altered carbon-nitrogen balance sensing, increased tolerance to cold, increased tolerance to water deficit conditions, increased tolerance to sucrose, or increased tolerance to hyperosmotic stress.

The invention also pertains to a transgenic plant, or a transformed seed produced from said transgenic plant, where the transgenic plant (or a plant grown from the transformed seed) comprises the aforementioned and above-described nucleic acid construct, and the transgenic plant has earlier flowering, longer floral organ retention (that is, delayed floral organ abscission), greater tolerance to low nitrogen conditions, altered carbon-nitrogen balance sensing, greater tolerance to cold, greater tolerance to water deficit conditions, greater tolerance to sucrose, or greater tolerance to hyperosmotic stress, as compared to a control plant.

The invention also encompasses a method for increasing the tolerance of a plant to low nitrogen conditions, hyperosmotic stress or cold as compared to a control plant, the method comprising:

(a) providing a nucleic acid construct comprising a recombinant nucleic acid sequence encoding a polypeptide sharing an amino acid identity with any of SEQ ID NO: 2, 4, 6, 8, 10, 12, 14, 16, 18, 20, 22, 24, 26, 28, 30, 32, 33, 34, 35, 36, 37, 38, 39, 40, 41, 42, 43, 44, 45, 46, 47, or 48, wherein when the polypeptide is overexpressed in a plant, the polypeptide regulates transcription and confers at least one regulatory activity resulting in an altered trait in the plant as compared to a control plant;

wherein the percent amino acid identity is selected from the group consisting of at least about 55%; and the altered trait is selected from the group consisting of: increased tolerance to low nitrogen conditions, altered carbon-nitrogen balance sensing, increased tolerance to cold, increased tolerance to water deficit conditions, increased tolerance to sucrose, and increased tolerance to hyperosmotic stress; and (b) transforming a target plant with the nucleic acid construct to produce a transformed plant;

wherein the transformed plant has greater tolerance to low nitrogen conditions, hyperosmotic stress or cold than the control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

The copy of the Sequence Listing, being submitted electronically with this patent application, provided under 37 CFR § 1.821-1.825, is a read-only memory computer-readable file in ASCII text format. The Sequence Listing is named "MBI0090DIV1.ST25.txt", the electronic file of the Sequence Listing was created on Oct. 30, 2007, and is 114,688 bytes in size (112 kilobytes in size as measured in MS-WINDOWS). The Sequence Listing is herein incorporated by reference in its entirety.

FIG. 1 shows a conservative estimate of phylogenetic relationships among the orders of flowering plants (modified from Soltis et al., 1997). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al., 2001.

Figure 2:
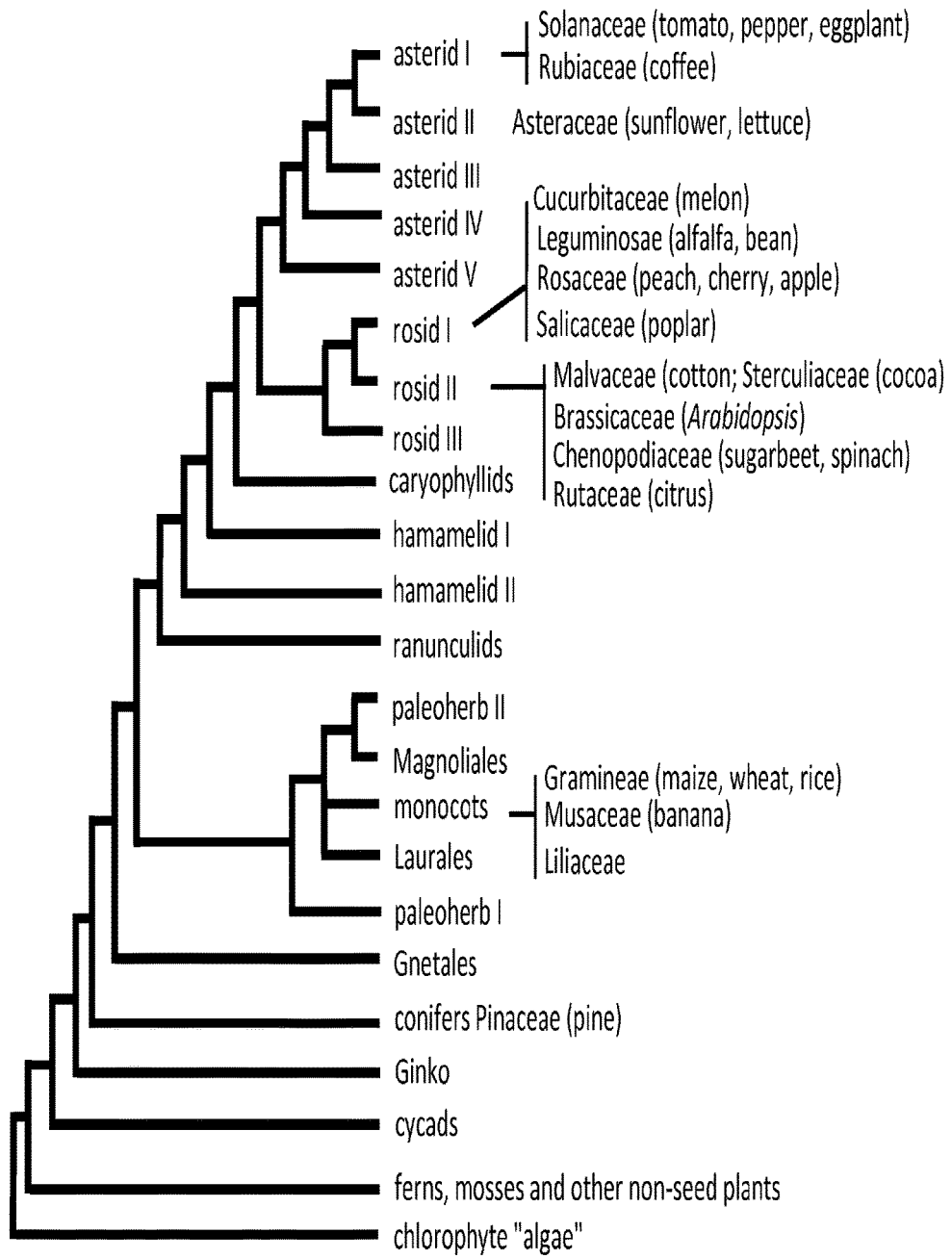

FIG. 2 shows a phylogenic dendogram depicting phylogenetic relationships of higher plant taxa, including clades containing tomato and *Arabidopsis*; adapted from Ku et al., 2000; and Chase et al., 1993.

Figure 3:
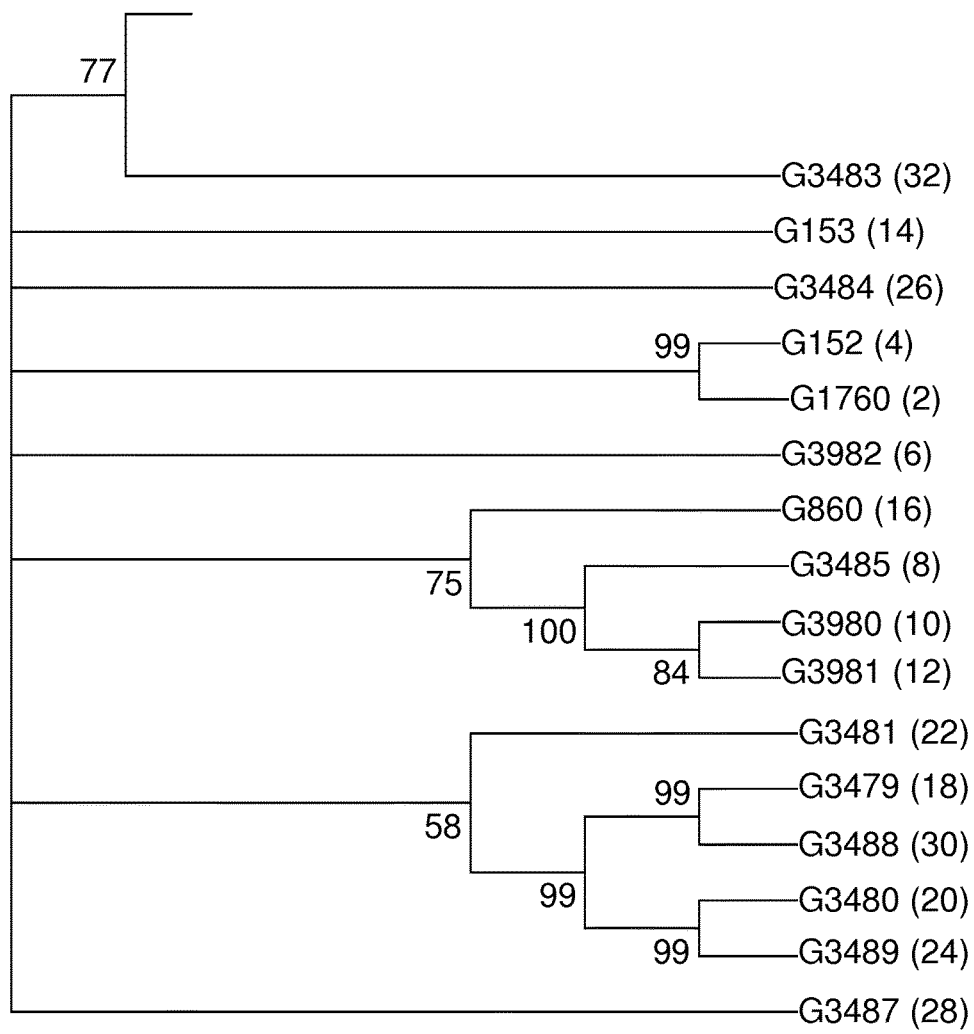

FIG. 3 shows a phylogenetic tree of G1760 and closely-related related full length proteins that was constructed using MEGA3 (www.megasoftware.net) software. ClustalW multiple alignment parameters were as follows:
Gap Opening Penalty: 10.00
Gap Extension Penalty: 0.20
Protein weight matrix: Gonnet series
Residue-specific Penalties: ON
Hydrophobic Penalties: ON
Gap Separation Distance: 4
End Gap Separation: OFF
Use negative matrix: OFF The phylogenetic tree was generated in MEGA3 using the neighbor joining algorithm and a p-distance model. Alignment gaps were handled using a pairwise deletion algorithm. A test of phylogeny was done via bootstrap with 1000 replications and Random Seed set to default. Cut off values of the bootstrap tree were set to 50%.

FIG. 4 is an alignment of the G1760 *Arabidopsis* clade member sequences any soy clade member G3980. The numbers in parentheses represent the SEQ ID NO of the associated sequence. Structural domains (adapted from Immink 2002, Davies 1996, and Huang 1996) are indicated by bars above alignment (MADS DNA binding domain, I nuclear localization domain, K protein interaction domain, and C-terminal activation domain).

FIGS. 5A-5F are a multiple sequence alignment of full length G1760 and closely-related proteins prepared using ClustalX software and the full-length protein sequences. These polypeptides were identified by BLAST and phylogenetic analysis. The conserved MADS domain is found within the box in FIG. 5A. Asterisks generated by Clustal indicate complete identity, colons represent highly similar residues, and dots represent similar residues throughout the alignment. SEQ ID NOs: are found in the parentheses.

DETAILED DESCRIPTION

The present invention relates to polynucleotides and polypeptides for modifying phenotypes of plants, particularly those associated with increased abiotic stress tolerance and increased yield with respect to a control plant (for example, a wild-type plant or a plant transformed with an "empty" expression vector lacking a DNA sequence of the invention). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a nucleic acid construct such as an expression vector or cassette, or otherwise recombined with one or more additional nucleic acids.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 5A-5F may be used to identify conserved domains and relatedness within these domains. An alignment may suitably be determined by means of computer programs known in the art, such as MACVECTOR software, (1999; Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. With respect to polynucleotides encoding presently disclosed polypeptides, a conserved domain is preferably at least nine base pairs (bp) in length. Transcription factor sequences that possess or encode for conserved domains that have a minimum percentage identity and have comparable biological activity to the present polypeptide sequences, thus being members of the same clade of transcription factor polypeptides, are encompassed by the invention. Overexpression in a transformed plant of a polypeptide that comprises, for example, a conserved domain having DNA-binding, activation or nuclear localization activity results in the transformed plant having similar improved traits as other transformed plants overexpressing other members of the same clade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides may be determined.

The conserved domains for many of the polypeptide sequences of the invention are listed in Table 1. Also, the polypeptides of Table 1 have conserved domains specifically indicated by amino acid coordinate start and stop sites. A comparison of the regions of these polypeptides allows one of skill in the art (see, for example, Reeves and Nissen, 1995, to identify domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985, Sambrook et al., 1989, and by Haymes et al., 1985, which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having 55% or greater identity with the conserved domain of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptide. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840, 544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes an conserved domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, FIG. 2, adapted from Ku et al., 2000; and see also Tudge, 2000).

A "control plant" as used in the present invention refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty vector or marker gene, but does not contain the recombinant polynucleotide of the present invention that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Transformation" refers to the transfer of a foreign polynucleotide sequence into the genome of a host organism such as that of a plant or plant cell. Typically, the foreign genetic material has been introduced into the plant by human manipulation, but any method can be used as one of skill in the art recognizes. Examples of methods of plant transformation include *Agrobacterium*-mediated transformation (De Blaere et al., 1987) and biolistic methodology (U.S. Pat. No. 4,945,050 to Klein et al., 1987).

A "transformed plant", which may also be referred to as a "transgenic plant" or "transformant", generally refers to a plant, a plant cell, plant tissue, seed or calli that has been through, or is derived from a plant that has been through, a transformation process in which a nucleic acid construct such as an expression vector, cassette, plasmid, or nucleic acid preparation that contains at least one foreign polynucleotide sequence is introduced into the plant. The nucleic acid construct contains genetic material that is not found in a wild-type plant of the same species, variety or cultivar. The genetic material may include a regulatory element, a transgene (for example, a foreign transcription factor sequence), an insertional mutagenesis event (such as by transposon or T-DNA insertional mutagenesis), an activation tagging sequence, a mutated sequence, a homologous recombination event, a sequence designed to engineer a change at an endogenous locus through a DNA-repair mechanism, or a sequence modified by chimeraplasty. In some embodiments the regulatory and transcription factor sequence may be derived from the host plant, but by their incorporation into a nucleic acid construct (e.g., an expression vector of cassette), represent an arrangement of the polynucleotide sequences not found a wild-type plant of the same species, variety or cultivar.

An "untransformed plant" is a plant that has not been through the transformation process.

A "stably transformed" plant, plant cell or plant tissue has generally been selected and regenerated on a selection media following transformation.

A nucleic acid construct (i.e., n expression vector or cassette) typically comprises a polypeptide-encoding sequence operably linked (i.e., under regulatory control of) to appropriate inducible or constitutive regulatory sequences that allow for the controlled expression of polypeptide. The construct can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as cold tolerance, low nutrient tolerance, hyperosmotic stress tolerance or yield. Any technique can be used to measure the amount of, comparative level of, or difference in any selected chemical compound or macromolecule in the transformed or transgenic plants, however.

"Trait modification" refers to a detectable difference in a characteristic in a plant ectopically expressing, transformed with, or genetically modified using a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a mutation in at least one gene in the plant or cell, where the mutation results in reduced or altered expression or reduced or altered activity of the polypeptide encoded by that gene compared to a control cell. The knockout can be the result of, for example, genomic disruptions, including transposons, tilling, and homologous recombination, antisense constructs, sense constructs, RNA silencing constructs, RNA interference, or targeted engineering of a gene at an endogenous locus by means of a homology dependent DNA repair process. A T-DNA insertion within a gene is an example of a genotypic alteration that may abolish expression of that gene.

"Ectopic expression or altered expression" in reference to a polynucleotide indicates that the pattern of expression in, e.g., a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also under the control of an inducible or tissue specific promoter. Thus, overexpression may occur throughout a plant, in specific tissues or cells of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors typically possess a conserved DNA binding domain. The transcription factors also typically comprise an amino acid subsequence that forms a transcriptional activation or repression domain that regulates expression of one or more abiotic stress tolerance genes in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al., 2003, U.S. Patent Application No. 20030101479). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al., 2000a). The plant transcription factors of the present invention are putative transcription factors.

Generally, transcription factors are involved in the control of gene expression which leads to changes in cellular processes including cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transformed or transgenic plants comprising isolated polynucleotides encoding transcription factors may also modify expression of endogenous genes, polynucleotides, and proteins. Examples include Peng et al., 1997, and Peng et al., 1999. In addition, many others have demonstrated that an *Arabidopsis* transcription factor expressed in an exogenous plant species elicits the same or very similar phenotypic response. See, for example, Fu et al., 2001; Nandi et al., 2000; Coupland, 1995; and Weigel and Nilsson, 1995.

In another example, Mandel et al., 1992b, and Suzuki et al., 2001, teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992a; Suzuki et al., 2001). Other examples include Müller et al., 2001; Kim et al., 2001; Kyozuka and Shimamoto, 2002; Boss and Thomas, 2002; He et al., 2000; and Robson et al., 2001.

In yet another example, Gilmour et al., 1998, teach *Arabidopsis* AP2 transcription factor, CBF1, which, when overexpressed in transgenic plants, increases plant freezing tolerance. Jaglo et al., 2001, further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP (SEQ ID NO:75) and DSAWR (SEQ ID NO:76), which bracket the AP2/EREBP DNA binding domains of the proteins and distinguish them from other members of the AP2/EREBP protein family (Jaglo et al., 2001).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Further, global transcript profiles have been used successfully as diagnostic tools for specific cellular states (e.g., cancerous vs. non-cancerous; Bhattacharjee et al., 2001; and Xu et al., 2001). Consequently, it is evident to one skilled in the art that similarity of transcript profile upon overexpression of different transcription factors would indicate similarity of transcription factor function.

Polypeptides and Polynucleotides of the Invention

The present invention includes putative transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in nucleic acid constructs for the purpose of producing transformed plants. Also provided are methods for improving the yield that may be obtained from a plant by modifying the mass, size or number of plant organs or seed of a plant by controlling a number of cellular processes, and for increasing a plant's resistance to abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased yield or abiotic stress tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in overexpressor plants. The changes in the characteristic(s) or trait(s) of the plants were then observed and found to confer abiotic stress tolerance and/or hence will likely increase yield and or crop quality. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of genes, polynucleotides, and/or proteins of plants or plant cells.

The data presented herein represent the results obtained in experiments with polynucleotides and polypeptides that may be expressed in plants for the purpose of reducing yield losses that arise from biotic and abiotic stress.

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships. After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, 1998).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al., 1994; Higgins et al., 1996). Groups of similar genes can also be identified with pair-wise BLAST analysis (Feng and Doolittle, 1987). For example, a clade of very similar MADS domain transcription factors from *Arabidopsis* all share a common function in flowering time (Ratcliffe et al., 2001), and a group of very similar AP2 domain transcription factors from *Arabidopsis* are involved in tolerance of plants to freezing (Gilmour et al., 1998). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, 2001).

Transcription factor gene sequences are conserved across diverse eukaryotic species lines (Goodrich et al., 1993; Lin et al., 1991; Sadowski et al., 1988). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994); Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616, issued 14 Nov. 2006), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from dicots and monocots can confer greater tolerance to drought-related stress as compared to control plants;

(iii) Myb-related *Arabidopsis* G682 (found in U.S. Pat. No. 7,223,904, issued 29 May 2007) and numerous phylogenetically-related sequences from dicots and monocots can confer greater tolerance to heat, drought-related stress, cold, and salt as compared to control plants;

(iv) WRKY family *Arabidopsis* G1274 (found in U.S. Pat. No. 7,196,245, issued 27 Mar. 2007) and numerous closely-related sequences from dicots and monocots have been shown to confer increased water deprivation tolerance, and (v) AT-hook family soy sequence G3456 (found in US patent publication 20040128712A1) and numerous phylogenetically-related sequences from dicots and monocots, increased biomass compared to control plants when these sequences are overexpressed in plants.

The polypeptides sequences belong to distinct clades of polypeptides that include members from diverse species. In each case, most or all of the clade member sequences derived from both dicots and monocots have been shown to confer increased tolerance to one or more abiotic stresses when the sequences were overexpressed, and hence will likely increase yield and or crop quality. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

At the nucleotide level, the sequences of the invention will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a region of a listed sequence excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

At the polypeptide level, the sequences of the invention will typically share at least about 50%, about 60%, about 70% or about 80% sequence identity, and more preferably about 85%, about 90%, about 95% or about 97% or more sequence identity to one or more of the listed full-length sequences, or to a listed sequence but excluding or outside of the known consensus sequence or consensus DNA-binding site.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp, 1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990; Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, n=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at (www.ncbi.nlm.nih.gov).

Other techniques for alignment are described by Doolittle, 1996. Preferably, an alignment program that permits gaps in the sequence is utilized to align the sequences. The Smith-Waterman is one type of algorithm that permits gaps in sequence alignments (see Shpaer, 1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein, 1990) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhammer et al., 1997), and the like, can be used to manipulate and analyze polynucleotide and polypeptide sequences encoded by polynucleotides. These databases, algorithms and other methods are well known in the art and are described in Ausubel et al., 1997, and in Meyers, 1995.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow, 2002, have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains characteristic of a particular transcription factor family. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Table 1 and the Sequence Listing. In addition to the sequences in Table 1 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase a plant's tolerance to one or more abiotic stresses, one skilled in the art would predict that other similar, phylogenetically related sequences falling within the present clades of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger and Kimmel, 1987, pages 467-469; and Anderson and Young, 1985.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$T_m(°C.)=81.5+16.6(\log [Na+])+0.41(\% G+C)-0.62(\% \text{ formamide})-500/L$ (I)DNA-DNA:

$T_m(°C.)=79.8+18.5(\log [Na+])+0.58(\% G+C)+0.12(\% G+C)^2-0.5(\% \text{ formamide})-820/L$ (II) DNA-RNA:

$T_m(°C.)=79.8+18.5(\log [Na+])+0.58(\% G+C)+0.12(\% G+C)^2-0.35(\% \text{ formamide})-820/L$ (III) RNA-RNA:

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

0.5×, 1.0×, 1.5×, or 2×SSC, 0.1% SDS at 50°, 55°, 60° or 65° C., or 6×SSC at 65° C.;

50% formamide, 4×SSC at 42° C.; or 0.5×SSC, 0.1% SDS at 65° C.;

with, for example, two wash steps of 10-30 minutes each. Useful variations on these conditions will be readily apparent to those skilled in the art. A formula for "SSC, 20×" may be found, for example, in Ausubel et al., 1997, in Appendix A1.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I. Transcription Factor Polynucleotide and Polypeptide Sequences of the Invention Background Information for G1760, the G1760 Clade, and Related Sequences MADS box genes comprise a large multigene family in vascular plants, and the *Arabidopsis* genome contains 104 of these genes. G1760 (AT4G37940, AGL21, SEQ ID NO: 2) and G3980 (SEQ ID NO: 10) fall within the G1760 clade. G1760 is most closely related to G152 (AT2G22630, AGL17G860, SEQ ID NO: 4), G860 (AT3G57230, AGL16, SEQ ID NO: 16), and G153 (AT2G14210, ANR1, SEQ ID NO: 14), all derived from *Arabidopsis*. G3980 is derived from soybeans. Phylogenetic analysis using the MADS box and I domains indicates that both G1760 and G860 (AT3G57230, AGL16, SEQ ID NO: 16) appear equally related to G3980.

The most well known role of plant MADS box genes is in the regulation of flower development. However, these proteins have also been shown to be important for a variety of other functions. In particular, an increasing number of MADS box proteins (such as SOC1/G154 and the MAF/FLC clade) have been found to influence the timing of flowering (Hepworth et al., 2002; Ratcliffe et al., 2003). The wide range of expression patterns of MADS box genes also suggests that their activities are not restricted to the floral realm. For instance, AGL3 is expressed in all aerial parts of the plant and AGL12, AGL14, and AGL17 are expressed only in roots (Riechmann and Meyerowitz, 1997; Alvarez-Buylla et al., 2000; Fernandez et al., 2000). Moreover, MADS box genes are involved not only in the intrinsic plant developmental programs, but also in those induced upon external stimuli. For example, ANR1 (G153), an *Arabidopsis* MADS box gene in the G1760 clade, controls the proliferation of lateral roots in response to nitrate (Zhang and Forde, 2000; Gan et al., 2005; Remans et al., 2006; Filleur et al., 2005). In summary, MADS-box genes have evolved to fulfill diverse roles in angiosperm plants, and as a family, play a part in regulating a very wide range of developmental and physiological processes.

MADS Box Protein Structure

The structure of MADS box proteins is well-studied, and a number of domains have been identified. The MADS domain is involved in DNA binding and dimerization (Riechmann et al., 1996; Huang et al., 1996; Tang and Perry, 2003; Immink et al., 2002), the I domain has been implicated in nuclear localization, the K domain is important for homo- and heterodimerization interactions (Davies et al., 1996; Yang et al., 2003; Lim et al., 2000; Honma and Goto 2001; Battaglia et al., 2006), and the highly divergent C-terminus is characterized as an activation domain (Lim et al., 2000). An alignment of G3980 and the G1760 *Arabidopsis* clade members is shown in FIG. 4, with these domains highlighted.

An alignment comparing full-length protein sequences of a larger number of G1760 clade members is presented in FIGS. 5A-5F. The sequences in FIGS. 5A-5F were identified by BLAST and phylogenetic analysis and thus determined to bear a close evolutionary relationship to the G1760 sequence. The conserved MADS domains are found within the box in FIG. 5A. Asterisks generated by Clustal indicate complete identity, colons represent highly similar residues, and dots represent similar residues throughout the alignment. SEQ ID NOs. are found in the parentheses.

Sequences found in other plant species that are closely-related to G1760 are listed in Table 1, which includes the SEQ ID NO: (Column 1); the species from which the sequence was derived (Column 2); the Gene Identifier ("GID", in Column 3); the percent identity of the polypeptide in Column 1 to the full length G1760 polypeptide, SEQ ID NO: 1, as determined by a BLASTp analysis with a wordlength (W) of 3, an expectation (E) of 10, and the BLOSUM62 scoring matrix Henikoff & Henikoff, 1989 (Column 4); the amino acid coordinates for the conserved MADS domains, beginning at the n-terminus of each of the sequences (Column 5), the SEQ ID NO: of each conserved MADS DNA binding domain (Column 6); the conserved MADS domain sequences of the respective polypeptides (Column 7); and the percentage identity of the conserved domain in Column 6 to the conserved domain of the G1760 sequence, SEQ ID NO: 33 (Column 8). Column 8 also includes the ratio of the number of identical residues over the total number of residues compared in the respective MADS domains (in parentheses).

TABLE 1

Percentage identities and conserved domains of G1760 and closely related sequences

| Col. 1 SEQ ID NO: | Col. 2 Species from which SEQ ID NO: is derived | Col. 3 Gene ID (GID) | Col. 4 Percent ID of protein to G1760 | Col. 5 Conserved MADS DNA binding domain amino acid coordinates | Col. 6 Conserved MADS DNA binding domain SEQ ID NO: | Col. 7 Conserved MADS DNA binding domain | Col. 8 Percent ID of conserved MADS DNA binding domain to G1760 conserved MADS DNA binding domain |
|---|---|---|---|---|---|---|---|
| 2 | Arabidopsis thaliana | G1760 | 100% | 2-57 | 33 | GRGKIVIQ RIDDSTSRQ VTFSKRRK | 100% (56/56) |

TABLE 1-continued

Percentage identities and conserved domains of G1760 and closely related sequences

| Col. 1 SEQ ID NO: | Col. 2 Species from which SEQ ID NO: is derived | Col. 3 Gene ID (GID) | Col. 4 Percent ID of protein to G1760 | Col. 5 Conserved MADS DNA binding domain amino acid coordinates | Col. 6 Conserved MADS DNA binding domain SEQ ID NO: | Col. 7 Conserved MADS DNA binding domain | Col. 8 Percent ID of conserved MADS DNA binding domain to G1760 conserved MADS DNA binding domain |
|---|---|---|---|---|---|---|---|
| | | | | | | GLIKKAKE LAILCDAE VGLIIFSST GKLYDF | |
| 4 | Arabidopsis thaliana | G152 | 75% | 2-57 | 34 | GRGKIVIQ KIDDSTSR QVTFSKRR KGLIKKAK ELAILCDA EVCLIIFSN TDKLYDF | 92.9% (52/56) |
| 6 | Antirrhinum majus (snapdragon) | G3982 | 62% | 2-57 | 35 | GRGKIVIQ RIDKSTSRQ VTFSKRRS GLLKKAKE LAILCDAE VGVVIFSST GKLYEF | 89.3% (50/56) |
| 8 | Glycine max | G3485 | 63% | 2-57 | 36 | GRGKIVIRR IDNSTSRQ VTFSKRRN GLLKKAKE LAILCDAE VGVMIFSS TGKLYDF | 89.3% (50/56) |
| 10 | Glycine max | G3980 | 63% | 2-57 | 37 | GRGKIVIRR IDNSTSRQ VTFSKRRN GLLKKAKE LAILCDAE VGVMIFSS TGKLYDF | 89.3% (50/56) |
| 12 | Glycine max | G3981 | 63% | 2-57 | 38 | GRGKIVIRR IDNSTSRQ VTFSKRRN GLLKKAKE LAILCDAE VGVMIFSS TGKLYDF | 89.3% (50/56) |
| 14 | Arabidopsis thaliana | G153 | 62% | 1-57 | 39 | GRGKIVIRR IDNSTSRQ VTFSKRRS GLLKKAKE LSILCDAEV GVIIFSSTG KLYDY | 87.5% (49/56) |
| 16 | Arabidopsis thaliana | G860 | 60% | 2-57 | 40 | GRGKIAIK RINNSTSRQ VTFSKRRN GLLKKAKE LAILCDAE VGVIIFSST GRLYDF | 85.7% (48/56) |
| 18 | Oryza sativa | G3479 | 62% | 2-57 | 41 | IDNSTSRQ VTFSKRRN GIFKKAKE LAILCDAE | 83.9% (47/56) |

TABLE 1-continued

Percentage identities and conserved domains of G1760 and closely related sequences

| Col. 1 SEQ ID NO: | Col. 2 Species from which SEQ ID NO: is derived | Col. 3 Gene ID (GID) | Col. 4 Percent ID of protein to G1760 | Col. 5 Conserved MADS DNA binding domain amino acid coordinates | Col. 6 Conserved MADS DNA binding domain SEQ ID NO: | Col. 7 Conserved MADS DNA binding domain | Col. 8 Percent ID of conserved MADS DNA binding domain to G1760 conserved MADS DNA binding domain |
|---|---|---|---|---|---|---|---|
| 20 | Oryza sativa | G3480 | 63% | 2-57 | 42 | GRGKIVRR IDNSTSRQ VTFSKRRN GIFKKAKE LAILCDAE VGLVIFSST GRLYEY | 83.9% (47/56) |
| 22 | Oryza sativa | G3481 | 58% | 2-57 | 43 | GRGKIVIRR IDNSTSRQ VTFSKRRN GIFKKAKE LAILCDAE VGLMIFSST GRLYEY | 83.9% (47/56) |
| 24 | Zea mays | G3489 | 66% | 2-57 | 44 | GRGKIVIRR IDNSTSRQ VTFSKRRN GLLKKAKE LSILCDAEV GLVVFSST GRLYEF | 83.9% (47/56) |
| 26 | Glycine max | G3484 | 61% | 2-57 | 45 | GRGKIAIRR IDNSTSRQ VTFSKRRN GLLKKARE LSILCDAEV GLMVFSST GKLYDY | 82.1% (46/56) |
| 28 | Zea mays | G3487 | 55% | 2-57 | 46 | GRGKIEIKR IDNATSRQ VTFSKRRG GLFKKAKE LAILCDAE VGLVVFSS TGRLYHF | 82.1% (46/56) |
| 30 | Zea mays | G3488 | 58% | 2-57 | 47 | GRGKIVIRR IDNSTSRQ VTFSKRRN GIFKKARE LAILCDAE VGLVIFSST GRLYEY | 82.1% (46/56) |
| 32 | Oryza sativa | G3483 | 71% | 2-57 | 48 | GRGKIEIKR IDNATSRQ VTFSKRRS GLFKKARE LSILCDAEV GLLVFSSTS RLYDF | 78.6% (44/56) |

A "MADS domain", such as is found in a polypeptide member of MADS transcription factor family, is an example of a conserved domain that is characteristic of a particular transcription factor family or clade. With respect to polynucleotides encoding presently disclosed polypeptides, a conserved domain is preferably at least nine base pairs (bp) in length. A conserved domain with respect to presently disclosed polypeptides refers to a domain within a polypeptide family that exhibits a higher degree of sequence homology. Thus, the polypeptides of the invention, and their conserved domains that are characteristic of the MADS transcription factor family or clade, share at least about 55%, or at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 78.6%, at least about 79%, at least about 80%, at least about 81%, at least about 82%, at least about 82.1%, at least about 83%, at least about 83.9%, at least about 84%, at least about 85%, at least about 85.7%, at least about 86%, at least about 87%, at least about 87.5%, at least about 88%, at least about 89%, at least about 89.3%, at least about 90%, at least about 91%, at least about 92%, at least about 92.9%, at least about 93%, at least about 94%, at least about 95%, at least about 96%, at least about 97%, at least about 98%, at least about 99%, or about 100% amino acid residue sequence identity to a polypeptide of the invention (e.g., SEQ ID NO: 2n, where n=1 to 16) or a conserved domain of a polypeptide of the invention (e.g., SEQ ID NOs: 33-48). Sequences that possess or encode for conserved domains that meet these criteria of percentage identity, and that have comparable biological activity to the present polypeptide sequences, thus being members of the G1760 clade polypeptides, are encompassed by the invention. The MADS domain (named after four members of the family: MCM1, AGAMOUS, DEFICIENS, and SRF, serum response factor) is a conserved DNA-binding/dimerization region present in a variety of transcription factors from different kingdoms (Riechmann and Meyerowitz, 1997). The MADS domains are required for conferring similar functions in the transcription factors of the invention. Overexpression in a transformed plant of a polypeptide that comprises a MADS family binding/dimerization conserved domain of the invention results in the transformed plant having larger seedling size, altered sugar sensing, increased tolerance to hyperosmotic stress, greater cold tolerance during germination and growth, greater tolerance to water deprivation, greater water use efficiency, altered flowering time, or altered C/N sensing or increased low nitrogen tolerance, as compared to a control plant.

Exemplary fragments of the sequences of the invention include fragments that comprise a conserved domain of a polypeptide of the invention, for example, the 2nd through 57th (2-57) amino acid residues of G1760 (SEQ ID NO: 2), amino acid residues 2-57 of G3980 (SEQ ID NO: 10) or amino acid residues 2-57 of G3480 (SEQ ID NO: 20).

Residues within a highly conserved region of a protein may be so conserved because of their importance to the function of that protein. Alignments of the sequences in the G1760 clade (FIGS. 4 and 5A-5F) indicate a high degree of conservation of the MADS domains, and particular residues, in clade members. In the sequences examined thus far, the MADS domain of G1760 clade members have generally been found to comprise the consensus sequence: G-R-G-K-I-X-I-X-R/K-I-D/N-X-S/A-T-S-R-Q-V-T-F-S-K-R-R-X-G-L/I-X-K-K-A-K/R-E-L-A/S-I-L-C-D-A-E-V-G/C-L/V-X-I/V-F-S-S/N-T-X-K/R-L-Y-X-F/Y (SEQ ID NO: 62), where a slash indicates one of the two residues on either side of the slash may be present, and X can be any amino acid residue (Table 2). The last row of Table 2 shows highly conserved residues (represented by asterisks) within the consensus MADS domain of the G1760 clade. Within the MADS domains of the G1760 clade sequences examined thus far are contained the smaller conserved subsequences: STSRQVTFSKRR (SEQ ID NO: 63) and ILCDAEV (SEQ ID NO: 64).

TABLE 2

Highly conserved residues within MADS domains of the G1760 clade

| Gene ID (GID) | MADS domain SEQ ID NO: | MADS domain |
|---|---|---|
| G1760 | 33 | GRGKIVIQRIDDSTSRQVTFSKRRKGLIKKAKELAILCDAEVGLIIFSSTGKLYDF |
| G3980 | 37 | GRGKIVIRRIDNSTSRQVTFSKRRNGLLKKAKELAILCDAEVGVMIFSSTGKLYDF |
| G152 | 34 | GRGKIVIQKIDDSTSRQVTFSKRRKGLIKKAKELAILCDAEVCLIIFSNTDKLYDF |
| G3982 | 35 | GRGKIVIQRIDKSTSRQVTFSKRRSGLLKKAKELAILCDAEVGVVIFSSTGKLYEF |
| G3485 | 36 | GRGKIVIRRIDNSTSRQVTFSKRRNGLLKKAKELAILCDAEVGVMIFSSTGKLYDF |
| G3981 | 38 | GRGKIVIRRIDNSTSRQVTFSKRRNGLLKKAKELAILCDAEVGVMIFSSTGKLYDF |
| G153 | 39 | GRGKIVIRRIDNSTSRQVTFSKRRSGLLKKAKELSILCDAEVGVIIFSSTGKLYDY |
| G860 | 40 | GRGKIAIKRINNSTSRQVTFSKRRNGLLKKAKELAILCDAEVGVIIFSSTGRLYDF |
| G3479 | 41 | GRGKIVIRRIDNSTSRQVTFSKRRNGIFKKAKELAILCDAEVGLVIFSSTGRLYEY |

TABLE 2-continued

Highly conserved residues within MADS domains of the G1760 clade

| Gene ID (GID) | MADS domain SEQ ID NO: | MADS domain |
|---|---|---|
| G3480 | 42 | GRGKIVIRRIDNSTSRQVTFSKRRNGIFKKAKELAILCDAEVGLMIFSST GRLYEY |
| G3481 | 43 | GRGKIVIRRIDNSTSRQVTFSKRRNGLLKKAKELSILCDAEVGLVVFSST GRLYEF |
| G3489 | 44 | GRGKIVIRRIDNSTSRQVTFSKRRNGIFKKAKELAILCDAEVGLVIFSST GRLYEY |
| G3484 | 45 | GRGKIAIRRIDNSTSRQVTFSKRRNGLLKKARELSILCDAEVGLMVFSST GKLYDY |
| G3487 | 46 | GRGKIEIKRIDNATSRQVTFSKRRGGLFKKAKELAILCDAEVGLVVFSST GRLYHF |
| G3488 | 47 | GRGKIVIRRIDNSTSRQVTFSKRRNGIFKKARELAILCDAEVGLVIFSST GRLYEY |
| G3483 | 48 | GRGKIEIKRIDNATSRQVTFSKRRSGLFKKARELSILCDAEVGLLVFSST SRLYDF |

***** *** *** *** *** ***

Example II. Project Types, Constructs and Cloning Information

A number of constructs were used to modulate the activity of sequences of the invention. An individual project was defined as the analysis of lines for a particular construct (for example, this might include G1760 lines that constitutively overexpressed a sequence of the invention). Generally, a full-length wild-type version of a gene was directly fused to a promoter that drove its expression in transformed or transgenic plants. Such a promoter could be a constitutive promoter such as the CaMV 35S promoter, or the native promoter of that gene. Alternatively, as noted below, a promoter that drives tissue specific or conditional expression could be used in similar studies.

Expression of a given polynucleotide from a particular promoter was achieved by a direct-promoter fusion construct in which that sequence was cloned directly behind the promoter of interest. A direct fusion approach has the advantage of allowing for simple genetic analysis if a given promoter-polynucleotide line is to be crossed into different genetic backgrounds at a later date.

As an alternative to direct promoter fusion, a two-component expression system was used to drive transcription factor expression as noted below. For the two-component system, two separate constructs were used: Promoter::LexA-GAL4TA and opLexA::TF. The first of these (Promoter::LexA-GAL4TA) comprised a desired promoter cloned in front of a LexA DNA binding domain fused to a GAL4 activation domain. The construct vector backbone also carried a kanamycin resistance marker, along with an opLexA::GFP reporter. Transgenic lines were obtained containing this first component, and a line was selected that showed reproducible expression of the reporter gene in the desired pattern through a number of generations. A homozygous population was established for that line, and the population was super-transformed with the second construct (opLexA::TF) carrying the transcription factor sequence of interest cloned behind a LexA operator site. This second construct vector backbone also contained a sulfonamide resistance marker.

Each of the above methods offers a number of pros and cons. A direct fusion approach allows for much simpler genetic analysis if a given promoter-transcription factor line was to be crossed into different genetic backgrounds at a later date. The two-component method, on the other hand, potentially allows for stronger expression to be obtained via an amplification of transcription.

In general, the lead transcription factor from each study group was expressed from a range of different promoters using a two component method. Arabidopsis paralogs were also generally analyzed by the two-component method, but were typically analyzed using the only 35S promoter. However, an alternative promoter was sometimes used for paralogs when there was already a specific indication that a different promoter might afford a more useful approach (such as when use of the 35S promoter was already known to generate deleterious effects). Putative orthologs from other species were usually analyzed by overexpression from a 35S CaMV promoter via a direct promoter-fusion construct.

For analysis of G1760-overexpressing plants, transgenic lines were created with the expression vector P1461 (SEQ ID NO: 49), which contained a G1760 cDNA clone. This construct constituted a 35S::G1760 direct promoter-fusion carrying a kanamycin resistance marker and was introduced into Arabidopsis plants.

A list of other constructs (PIDs) included in this report, indicating the promoter fragment that was used, or may be used, to drive the transgene, along with the cloning vector backbone, is provided in Table 3. Compilations of the sequences of promoter fragments and the expressed transgene sequences within the PIDs are provided in the Sequence Listing.

TABLE 3

Sequences of promoter fragments and the expressed transgene sequences

| Construct | Construct PID | SEQ ID NO: of PID | Promoter | Expression system |
|---|---|---|---|---|
| 35S::G1760 | P1461 | 49 | 35S | Direct promoter-fusion |
| 35S::G152 | P896 | 50 | 35S | Direct promoter-fusion |
| 35S::G3981 | P26747 | 51 | 35S | Direct promoter-fusion |
| 35S::G153 | P15260 | 52 | 35S | Direct promoter-fusion |
| 35S::G860 | P1269 | 53 | 35S | Direct promoter-fusion |
| 35S::G3479 | P26738 | 54 | 35S | Direct promoter-fusion |
| 35S::G3480 | P21388 | 55 | 35S | Direct promoter-fusion |
| 35S::G3481 | P26740 | 56 | 35S | Direct promoter-fusion |
| 35S::G3489 | P26743 | 57 | 35S | Direct promoter-fusion |
| 35S::G3484 | P26744 | 58 | 35S | Direct promoter-fusion |
| 35S::G3487 | P26820 | 59 | 35S | Direct promoter-fusion |
| G1760 (two components: opLexA::G1760 and 35S::m35S::oEnh::LexAGal4) | P6506 and P3371 | 61 and 65 | 35S | Two-component super transformation construct containing cDNA clone of G1760 and promoter::LexA-GAL4TA construct in two-component system |
| SUC2 promoter and G1760 (two components: opLexA::G1760 and prSUC2::m35S::oEnh::LexAGal4(GFP)) | P5290 and P3371 | 65 and 66 | Vascular tissue-specific SUC2 | Two-component super transformation construct containing cDNA clone of G1760 and promoter::LexA-GAL4TA construct in two-component system |
| prAt5g52300::G1760 | Drought inducible promoter prAt5g52300 fused to G1760 | 67 | Drought inducible expression | Direct promoter-fusion |
| prAT5G43840::G1760 | Drought inducible promoter prAT5G43840 fused to G1760 | 68 | Drought inducible expression | Direct promoter-fusion |
| SUC2::G1760 | P28765 | 69 | Vascular tissue-specific SUC2 | Direct promoter-fusion |
| G1760 (two components: opLexA::G1760 and prRSI1::m35S::oEnh::LexAGal4(GFP)) | P3371 and P5310 | 70 | Root-specific RSI1 | Two-component super transformation construct containing cDNA clone of G1760 |
| G1760 (two components: opLexA::G1760 and prARSK1::m35S::oEnh::LexAGal4(GFP)) | P3371 and P5311 | 71 | Root-specific ARSK1 | Two-component super transformation construct containing cDNA clone of G1760 |
| G1760 (prGmF6::G1760) | P28771 | 72 | Abscission zone-specific | Direct promoter-fusion |

TABLE 3-continued

Sequences of promoter fragments and the expressed transgene sequences

| Construct | Construct PID | SEQ ID NO: of PID | Promoter | Expression system |
|---|---|---|---|---|
| G1760 (prCYCD3::G1760) | P28778 | 73 | promoter prGmF6 Dividing tissue-specific promoter prCYCD3 | Direct promoter-fusion |
| G1760 (prCAB1::G1760) | P28752 | 74 | Green tissue-specific promoter prCAB1 | Direct promoter-fusion |

Example III. Transformation Methods

Transformation of *Arabidopsis* was performed by an *Agrobacterium*-mediated protocol based on the method of Bechtold and Pelletier, 1998. Unless otherwise specified, all experimental work was done using the Columbia ecotype.

Plant Preparation.

*Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial Culture Preparation.

*Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1×B5 Vitamins, 5% sucrose, 1 mg/ml benzylaminopurine riboside, 200 µl/L Silwet L77) until an A600 reading of 0.8 was reached.

Transformation and Seed Harvest.

The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This transformed seed was deemed T0 seed, since it was obtained from the T0 generation, and was later plated on selection plates (either kanamycin or sulfonamide). Resistant plants that were identified on such selection plates comprised the T1 generation.

Example IV. Morphology

Morphological analysis was performed to determine whether changes in polypeptide levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by supertransformation), Transformed seeds were selected on MS medium with 0.3% sucrose and 1.5 mg/l sulfonamide. KO lines were usually germinated on plates without a selection. Seeds were cold-treated (stratified) on plates for three days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix, Sun Gro Horticulture, Bellevue, Wash.). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time were apparent, flowering time was re-examined under both 12-hour and 24-hour light to assess whether the phenotype was photoperiod dependent. Under our 24-hour light growth conditions, the typical generation time (seed to seed) was approximately 14 weeks.

Because many aspects of *Arabidopsis* development are dependent on localized environmental conditions, in all cases plants were evaluated in comparison to controls in the same flat. As noted below, controls for transformed lines were wild-type plants or transformed plants harboring an empty transformation vector selected on kanamycin or sulfonamide. Careful examination was made at the following stages: seedling (1 week), rosette (2-3 weeks), flowering (4-7 weeks), and late seed set (8-12 weeks). Seed was also inspected. Seedling morphology was assessed on selection plates. At all other stages, plants were macroscopically evaluated while growing on soil. All significant differences (including alterations in growth rate, size, leaf and flower morphology, coloration, and flowering time) were recorded, but routine measurements were not taken if no differences were apparent.

Note that for a given project (gene-promoter combination, GAL4 fusion lines, RNAi lines etc.), up to ten lines were typically examined in subsequent plate based physiology assays.

Example V. Physiology Experimental Methods

In subsequent Examples, unless otherwise indicted, morphological and physiological traits are disclosed in comparison to wild-type control plants. That is, a transformed plant that is described as large and/or drought tolerant was large and more tolerant to drought with respect to a control plant, the latter including wild-type plants, parental lines and lines transformed with an "empty" vector that does not contain a transcription factor polynucleotide sequence of interest. When a plant is said to have a better performance than controls, it generally was larger, had greater yield, and/or showed less stress symptoms than control plants. The better performing lines may, for example, have produced less anthocyanin, or were larger, greener, or more vigorous in response to a particular stress, as noted below. Better performance generally implies greater size or yield, or tolerance to a particular biotic or abiotic stress, less sensitivity to ABA, or better recovery from a stress (as in the case of a soil-based drought treatment) than controls.

Plate Assays.

Different plate-based physiological assays (shown below), representing a variety of abiotic and water-deprivation-stress related conditions, were used as a pre-screen to identify top performing lines (i.e. lines from transformation with a particular construct), that were generally then tested in subsequent soil based assays. Typically, ten lines were subjected to plate assays, from which the best three lines were selected for subsequent soil based assays. However, in projects where significant stress tolerance was not obtained in plate based assays, lines were not submitted for soil assays.

In addition, some projects were subjected to nutrient limitation studies. A nutrient limitation assay was intended to find genes that allowed more plant growth upon deprivation of nitrogen. Nitrogen is a major nutrient affecting plant growth and development that ultimately impacts yield and stress tolerance. These assays monitored primarily root but also shoot growth on nitrogen deficient media. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process is regulated by light, as well as by C/N metabolic status of the plant. A C/N sensing assay was thus used to look for alterations in the mechanisms plants use to sense internal levels of carbon and nitrogen metabolites which could activate signal transduction cascades that regulate the transcription of nitrogen-assimilatory genes. To determine whether these mechanisms are altered, we exploited the observation that wild-type plants grown on media containing high levels of sucrose (3%) without a nitrogen source accumulate high levels of anthocyanins. This sucrose induced anthocyanin accumulation can be relieved by the addition of either inorganic or organic nitrogen. We used glutamine as a nitrogen source since it also serves as a compound used to transport nitrogen in plants.

Germination Assays.

The following germination assays were conducted with *Arabidopsis* overexpressors of G1760 and closely-related sequences: NaCl (150 mM), mannitol (300 mM), sucrose (9.4%), ABA (0.3 µM), cold (8° C.), polyethylene glycol (10%, with Phytogel as gelling agent), or C/N sensing or low nitrogen medium. In the text below, —N refers to basal media minus nitrogen plus 3% sucrose and −N/+Gln is basal media minus nitrogen plus 3% sucrose and 1 mM glutamine.

All germination assays were performed in aseptic conditions. Growing the plants under controlled temperature and humidity on sterile medium produces uniform plant material that has not been exposed to additional stresses (such as water stress) which could cause variability in the results obtained. All assays were designed to detect plants that were more tolerant or less tolerant to the particular stress condition and were developed with reference to the following publications: Jang et al., 1997, Smeekens, 1998, Liu and Zhu, 1997, Saleki et al., 1993, Wu et al., 1996, Zhu et al., 1998, Alia et al., 1998, Xin and Browse, 1998, Leon-Kloosterziel et al., 1996. Where possible, assay conditions were originally tested in a blind experiment with controls that had phenotypes related to the condition tested.

Prior to plating, seed for all experiments were surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds were re-suspended in 0.1% sterile agarose and stratified at 4° C. for 3-4 days.

All germination assays follow modifications of the same basic protocol. Sterile seeds were sown on the conditional media that has a basal composition of 80% MS+Vitamins. Plates were incubated at 22° C. under 24-hour light (120-130 µE m$^{-2}$ s$^{-1}$) in a growth chamber. Evaluation of germination and seedling vigor was performed five days after planting.

Growth Assays.

The following growth assays were conducted with *Arabidopsis* overexpressors of G1760 and closely-related sequences: severe desiccation (a type of water deprivation assay), growth in cold conditions at 8° C., root development (visual assessment of lateral and primary roots, root hairs and overall growth), and phosphate limitation. For the nitrogen limitation assay, plants were grown in 80% Murashige and Skoog (MS) medium in which the nitrogen source was reduced to 20 mg/L of NH$_4$NO$_3$. Note that 80% MS normally has 1.32 g/L NH$_4$NO$_3$ and 1.52 g/L KNO$_3$. For phosphate limitation assays, seven day old seedlings were germinated on phosphate-free medium in MS medium in which KH$_2$PO$_4$ was replaced by K$_2$SO$_4$.

Unless otherwise stated, all experiments were performed with the *Arabidopsis thaliana* ecotype Columbia (col-0), soybean or maize plants. Assays were usually conducted on non-selected segregating T2 populations (in order to avoid the extra stress of selection). Control plants for assays on lines containing direct promoter-fusion constructs were Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

Procedures

For chilling growth assays, seeds were germinated and grown for seven days on MS+Vitamins+1% sucrose at 22° C. and then transferred to chilling conditions at 8° C. and evaluated after another 10 days and 17 days.

For severe desiccation (plate-based water deficit) assays, seedlings were grown for 14 days on MS+Vitamins+1% Sucrose at 22° C. Plates were opened in the sterile laminar flow hood for 3 hr for hardening and then seedlings were removed from the media and let dry for two hours in the hood. After this time the plants were transferred back to plates and incubated at 22° C. for recovery. The plants were then evaluated after five days.

For the polyethylene glycol (PEG) hyperosmotic stress tolerance screen, plant seeds were gas sterilized with chlorine gas for 2 hrs. The seeds were plated on each plate containing 3% PEG, 1/2×MS salts, 1% phytagel, and 10 µg/ml glufosinate-ammonium (BASTA). Two replicate plates per seed line were planted. The plates were placed at 4° C. for 3 days to stratify seeds. The plates were held vertically for 11 additional days at temperatures of 22° C. (day) and 20° C. (night). The photoperiod was 16 hrs. with an average light intensity of about 120 µmol/m2/s. The racks holding the plates were rotated daily within the shelves of the growth chamber carts. At 11 days, root length measurements are made. At 14 days, seedling status was determined, root length was measured, growth stage was recorded, the visual color was assessed, pooled seedling fresh weight was measured, and a whole plate photograph was taken.

Wilt Screen Assay.

Transformed and wild-type soybean plants were grown in 5" pots in growth chambers. After the seedlings reached the V1 stage (the V1 stage occurs when the plants have one trifoliolate, and the unifoliolate and first trifoliolate leaves are unrolled), water was withheld and the drought treatment thus started. A drought injury phenotype score was recorded, in increasing severity of effect, as 1 to 4, with 1 designated no obvious effect and 4 indicating a dead plant. Drought scoring was initiated as soon as one plant in one growth chamber had a drought score of 1.5. Scoring continued every day until at least 90% of the wild type plants had achieved scores of 3.5 or more. At the end of the experiment the scores for both transgenic and wild type soybean seedlings were statistically analyzed using Risk Score and Survival analysis methods (Glantz, 2001; Hosmer and Lemeshow, 1999).

Water Use Efficiency (WUE).

Long term WUE may be estimated using a method similar to that described by Nienhuis et al. (1994). Seeds of transformants and controls are suspended in 0.1% agarose and stratified for 3 days at 4° C. The agarose/seed suspension is germinated under 12 hour light at 22° C. for 2 days. Germinated seeds are then planted into Petri dishes containing a known amount of soil. Each lid is spray painted black to reduce algae growth on soil and to ensure plant germination from a 3.2 mm diameter hole drilled into the top of the Petri dish lid. Plates are sealed with a layer of parafilm and a layer of 3M venting tape and grown under 12 hr light at 22° C. Rosettes are harvested after 29 days. To keep humidity high, plates are placed in trays covered with plastic wrap. Water use efficiency is calculated by taking the fresh or dry rosette weight and dividing by the weight of water used. The amount of water lost by transpiration through the plant is estimated by subtracting the (plate+soil) final weight from the (plate+soil) initial weight. Data from 20 to 40 samples per line may be averaged together to give a mean and standard deviation.

Another potential indicator of WUE is stomatal conductance, that is, the extent to which stomata were open.

Data Interpretation

At the time of evaluation, plants were given one of the following scores:

(++) Substantially enhanced performance compared to controls. The phenotype was very consistent and growth was significantly above the normal levels of variability observed for that assay.

(+) Enhanced performance compared to controls. The response was consistent but was only moderately above the normal levels of variability observed for that assay.

(wt) No detectable difference from wild-type controls.

(−) Impaired performance compared to controls. The response was consistent but was only moderately above the normal levels of variability observed for that assay.

(−−) Substantially impaired performance compared to controls. The phenotype was consistent and growth was significantly above the normal levels of variability observed for that assay.

(n/d) Experiment failed, data not obtained, or assay not performed.

Example VI. Soil Drought (Clay Pot)

The *Arabidopsis* soil drought assay (water deficit assays performed in clay pots) may be performed using a method based on that described by Haake et al., 2002.

Experimental Procedure.

Seedlings are first germinated on selection plates containing either kanamycin or sulfonamide.

Seeds are sterilized by a 2 minute ethanol treatment followed by 20 minutes in 30% bleach/0.01% Tween and five washes in distilled water. Seeds are sown to MS agar in 0.1% agarose and stratified for three days at 4° C., before transfer to growth cabinets with a temperature of 22° C. After seven days of growth on selection plates, seedlings are transplanted to 3.5 inch diameter clay pots containing 80 g of a 50:50 mix of vermiculite:perlite topped with 80 g of ProMix. Typically, each pot contained 14 seedlings, and plants of the transformed line being tested are in separate pots to the wild-type controls. Pots containing the transgenic line versus control pots are interspersed in the growth room, maintained under 24-hour light conditions (18-23° C., and 90-100 µE m$^{-2}$ s$^{-1}$) and watered for a period of 14 days. Water is then withheld and pots are placed on absorbent paper for a period of 8-10 days to apply a drought treatment. After this period, a visual qualitative "drought score" from 0-6 is assigned to record the extent of visible drought stress symptoms. A score of "6" corresponds to no visible symptoms whereas a score of "0" corresponds to extreme wilting and the leaves having a "crispy" texture. At the end of the drought period, pots are re-watered and scored after 5-6 days; the number of surviving plants in each pot is counted, and the proportion of the total plants in the pot that survived is calculated.

Analysis of Results.

In a given experiment, five or more pots of a transformed line are typically compared with five or more pots of the appropriate control. The mean drought score and mean proportion of plants surviving (survival rate) are calculated for both the transformed line and the wild-type pots. In each case a p-value* is calculated, which indicates the significance of the difference between the two mean values. The p-value may be calculated with a Mann-Whitney rank-sum test.

Example VII. Soil Drought Physiological and Biochemical Measurements

These experiments determine the physiological basis for the drought tolerance conferred by each lead and are typically performed under soil grown conditions. Usually, the experiment is performed under photoperiodic conditions of 10-hr or 12-hr light. Where possible, a given project (gene/promoter combination or protein variant) is represented by three independent lines. Plants are usually at late vegetative/early reproductive stage at the time measurements are taken. Typically we assay three different states: a well-watered state, a mild-drought state and a moderately severe drought state. In each case, we make comparisons to wild-type plants with the same degree of physical stress symptoms (wilting). To achieve this, staggered samplings are often required. Typically, for a given line, ten individual plants are assayed for each state.

The following physiological parameters are routinely measured: relative water content, ABA content, proline content, and photosynthesis rate. In some cases, measurements of chlorophyll levels, starch levels, carotenoid levels, and chlorophyll fluorescence are also made.

Analysis of Results.

In a given experiment, for a particular parameter, we typically compare about 10 samples from a given transformed line with about 10 samples of the appropriate wild-type control at each drought state. The mean values for each physiological parameter are calculated for both the transformed line and the wild-type pots. In each case, a p-value (calculated via a simple t-test) is determined, which indicates the significance of the difference between the two mean values.

A typical procedure is described below; this corresponds to method used for the drought time-course experiment which we perform on wild-type plants during our baseline studies at the outset of the drought program.

Procedure.

Seeds are stratified for three days at 4° C. in 0.1% agarose and sown on Metromix 200 in 2.25 inch pots (square or round). Plants are maintained in individual pots within flats grown under short days (10 hours light, 14 hours dark). Seedlings are watered as needed to maintain healthy plant growth and development. At 7 to 8 weeks after planting, plants are used in drought experiments.

Plants matched for equivalent growth development (rosette size) are removed from plastic flats and placed on absorbent paper. Pots containing plants used as well-watered controls are placed within a weigh boat and the dish placed on the absorbent paper. The purpose of the weigh boat is to retain any water that might leak from well-watered pots and affect pots containing plants undergoing the drought stress treatment.

On each day of sampling, up to 18 plants subjected to drought conditions and 6 well-watered controls (from each transformed line) are picked from a randomly generated pool. Biochemical analysis for photosynthesis, ABA, and proline is performed on the next three youngest, most fully expanded leaves. Relative water content is analyzed using the remaining rosette tissue.

Measurement of Photosynthesis.

Photosynthesis is measured using a LICOR LI-6400 (Li-Cor Biosciences, Lincoln, Nebr.). The LI-6400 uses infrared gas analyzers to measure carbon dioxide to generate a photosynthesis measurement. It is based upon the difference of the $CO_2$ reference (the amount put into the chamber) and the $CO_2$ sample (the amount that leaves the chamber). Since photosynthesis is the process of converting $CO_2$ to carbohydrates, we expect to see a decrease in the amount of $CO_2$ sample. From this difference, a photosynthesis rate can be generated. In some cases, respiration may occur and an increase in $CO_2$ detected. To perform measurements, the LI-6400 is set-up and calibrated as per LI-6400 standard directions. Photosynthesis is measured in the youngest, most fully expanded leaf at 300 and 1000 ppm $CO_2$ using a metal halide light source. This light source provides about 700 µE $m^2 s^{-1}$.

Fluorescence is measured in dark and light adapted leaves using either a LI-6400 (LICOR) with a leaf chamber fluorometer attachment or an OS-1 (Opti-Sciences, Hudson, N.H.) as described in the manufacturer's literature. When the LI-6400 is used, all manipulations are performed under a dark shade cloth. Plants are dark adapted by placing in a box under this shade cloth until used. The OS-30 uses small clips to create dark adapted leaves.

Chlorophyll/Carotenoid Determination.

For some experiments, chlorophyll is estimated in methanolic extracts using the method of Porra et al., 1989. Carotenoids are estimated in the same extract at 450 nm using an A(1%) of 2500. We measure chlorophyll using a Minolta SPAD-502 (Konica Minolta Sensing Americas, Inc., Ramsey, N.J.). When the SPAD-502 is used to measure chlorophyll, both carotenoid and chlorophyll content and amount can also be determined via HPLC. Pigments are extracted from leave tissue by homogenizing leaves in acetone:ethyl acetate (3:2). Water is added, the mixture centrifuged, and the upper phase removed for HPLC analysis. Samples are analyzed using a Zorbax (Agilent Technologies, Palo Alto, Calif.) C18 (non-endcapped) column (250×4.6) with a gradient of acetonitrile:water (85:15) to acetonitrile:methanol (85:15) in 12.5 minutes. After holding at these conditions for two minutes, solvent conditions are changed to methanol:ethyl acetate (68:32) in two minutes. Carotenoids and chlorophylls are quantified using peak areas and response factors calculated using lutein and beta-carotene as standards.

Phenotypic Analysis: Flowering Time.

Plants are grown in soil. Flowering time is determined based on either or both of (i) number to days after planting to the first visible flower bud. (ii) the total number of leaves (rosette or rosette plus cauline) produced by the primary shoot meristem.

Screening for Water Use Efficiency

An aspect of this invention provides transgenic plants with enhanced water use efficiency and/or water deprivation tolerance.

This example describes a high-throughput method for greenhouse selection of transgenic plants to wild type plants (tested as inbreds or hybrids) for water use efficiency. This selection process imposed three drought/re-water cycles on the plants over a total period of 15 days after an initial stress free growth period of 11 days. Each cycle consisted of five days, with no water being applied for the first four days and a water quenching on the fifth day of the cycle. The primary phenotypes analyzed by the selection method were the changes in plant growth rate as determined by height and biomass during a vegetative drought treatment. The hydration status of the shoot tissues following the drought was also measured. The plant heights were measured at three time points. The first was taken just prior to the onset drought when the plant was 11 days old, which was the shoot initial height (SIH). The plant height was also measured halfway throughout the drought/re-water regimen, on day 18 after planting, to give rise to the shoot mid-drought height (SMH). Upon the completion of the final drought cycle on day 26 after planting, the shoot portion of the plant was harvested and measured for a final height, which was the shoot wilt height (SWH) and also measured for shoot wilted biomass (SWM). The shoot was placed in water at 40° C. in the dark. Three days later, the weight of the shoot was determined to provide the shoot turgid weight (STM). After drying in an oven for four days, the weights of the shoots were determined to provide shoot dry biomass (SDM). The shoot average height (SAH) was the mean plant height across the three height measurements. If desired, the procedure described above may be adjusted for +/−~ one day for each step. To correct for slight differences between plants, a size corrected growth value was derived from SIH and SWH. This was the Relative Growth Rate (RGR). Relative Growth Rate (RGR) was calculated for each shoot using the formula [RGR %=(SWH−SIH)/((SWH+SIH)/2)*100]. Relative water content (RWC) is a measurement of how much (%) of the plant was water at harvest. Water Content (RWC) was calculated for each shoot using the formula [RWC %=(SWM−SDM)/(STM−SDM)*100]. For example, fully watered corn plants of this stage of development have around 98% RWC.

Example VIII. Morphological Observations and Physiological Experimental Results

All observations are made with respect to control plants, including wild-type and non-transformed plant lines (i.e., lines that were not overexpressing a G1760 clade member).
G1760 (Seq Id No: 2)

A significant number of *Arabidopsis* plant lines overexpressing G1760 (SEQ ID NO: 2) under the control of the 35S promoter (35S::G1760) were more tolerant to hyperosmotic stress, demonstrated in 9.4% sucrose media or dehydration (a water deficit assay) plate-based assays.

A number of independent G1760 constitutive overexpressors in Arabidopis were also more tolerant to cold (8° C.) and showed a low nitrogen tolerant phenotype in plate-based cold and C/N sensing germination assays, respectively.

When overexpressed in a two-component constitutive system under the control of the CaMV 35S promoter (opLexA::G1760 and 35S::m35S::oEnh::LexAGal4), seedlings of G1760 overexpressing *Arabidopsis* lines were more tolerant to 9.4% sucrose (an indication of altered sugar sensing and/or increased tolerance to hyperosmotic stress) and produced less anthocyanin at 8° C. (indicating improved cold tolerance) than control plants. Seedlings of direct fusion promoter::TF (35S::G1760) and two component overexpressors were also found to be more tolerant to low nitrogen conditions than controls in a C/N sensing assay.

Seedlings from two of ten two-component constitutive overexpressor lines for G1760 in *Arabidopsis* were also observed to be slightly larger than controls following germination, a potential indicator of seedling vigor.

An early flowering phenotype was observed in both *Arabidopsis* and soybean lines overexpressing G1760 under the regulatory control of the CaMV 35S promoter. *Arabidopsis* plants overexpressing G1760 under the regulatory control of the SUC2 promoter, which confers expression in the phloem, also exhibited accelerated flowering. Plants from a single line of 35S::G1760 were also noted, on one particular plant date, to have a delay in the abscission of petals, following pollination.

Relative to control plants, field grown soybean lines which overexpressed G1760 from a 35S CaMV promoter produced an increased number of pods per node, an increased number of nodes per plant, and increased chlorophyll content. Early flowering, relative to control plants, was also observed, but maturity was delayed by several days. Soy plants overexpressing G1760 were generally taller than controls.

Maize plants overexpressing G1760 were also found to be early flowering. The maize G1760 overexpressors were more tolerant to water deficit, as the plants were found to have greater shoot mass and significantly greater vegetative and reproductive success than controls when grown under water deficit conditions in greenhouse and field trials.

*Arabidopsis* G153 (SEQ ID NO: 14)

Similar to G1760, G153 (SEQ ID NO: 14) overexpressing *Arabidopsis* lines (35S::G153) showed a low nitrogen tolerant phenotype in plate-based C/N sensing germination assays compared to control *Arabidopsis* plants.

G153 overexpressing *Arabidopsis* seedlings were also more tolerant to 9.4% sucrose than control plants, indicating that G153 can confer increased hyperosmotic stress tolerance.

G153 overexpressing *Arabidopsis* seedlings were moderately more tolerant to germination in cold conditions (8° C.) than control plants.

An early flowering phenotype was observed in *Arabidopsis* lines overexpressing G153 under the regulatory control of the CaMV 35S promoter
*Arabidopsis* G152 (SEQ ID NO: 4)

G152 (SEQ ID NO: 4) overexpressing *Arabidopsis* seedlings were more tolerant to 9.4% sucrose than control plants, indicating that G152 can confer increased hyperosmotic stress tolerance.

G152-overexpressing *Arabidopsis* lines (35S::G152) were found to be slightly more tolerant to cold (8° C.) conditions than control *Arabidopsis* plants in plate-based cold germination assays.

After five days of growth, some 35S::G152 lines were noted to be slightly larger than control lines, a potential indicator of seedling vigor.
*Arabidopsis* G860 (SEQ ID NO: 16)

G860 (SEQ ID NO: 16) overexpressing *Arabidopsis* seedlings were more tolerant to 9.4% sucrose than control plants, indicating that G860 can confer increased hyperosmotic stress tolerance.

Similar to G1760, G860 overexpressing *Arabidopsis* lines (35S::G860) showed a low nitrogen tolerant phenotype in plate-based C/N sensing germination assays than control *Arabidopsis* plants. 35S::G860 lines were also noted to be more tolerant to cold (8° C.) conditions than control *Arabidopsis* plants in germination assays.

An early flowering/accelerated development phenotype was also observed in a minority (five of twenty) *Arabidopsis* lines overexpressing G860 under the regulatory control of the CaMV 35S promoter.
Soy G3980 (SEQ ID NO: 10)

Morphologically, soybean lines overexpressing soy-derived sequence G3980 (SEQ ID NO: 10) under the regulatory control of the CaMV 35S promoter were similar in many ways to soy plants overexpressing *Arabidopsis* G1760. An early flowering phenotype was observed in 35S::G3980 transgenic lines in both soy plants and *Arabidopsis*. Similar to the traits conferred by the *Arabidopsis* sequence, soy plants overexpressing the soy sequence also had more nodes per plant. These plants also had enhanced floral and pod retention, and demonstrated a delay in maturation relative to controls.

G3980-overexpressing *Arabidopsis* lines (35S::G3980) were found to show less evidence of cold stress than control plants in plate-based cold germination assays carried out at 8° C.

In maize plants, G3980 (SEQ ID NO: 10) was also introduced into maize plants by way of an expression vector under the regulatory control of the rice actin constitutive promoter and shown to improve performance under water deficit conditions. Overexpression of G3980 in corn conferred early flowering and provided enhanced drought tolerance in a number of separate trials in a greenhouse screen, and improved tolerance to water deprivation in both a leaf wilt and ear damage screen performed under drought conditions in the field.

Soybean lines that overexpressed G3980 from a 35S CaMV promoter also exhibited drought tolerance. Thus, like G1760 from *Arabidopsis*, G3980 from soy was shown to improve water deficit tolerance.

The G1760 Clade and Altered Flowering Time

As detailed above, a number of G1760 clade members were shown to confer early flowering and/or development under the control of the 35S promoter in *Arabidopsis* plants. These included G1760 (SEQ ID NO: 2), G153 (SEQ ID NO: 14), G860 (SEQ ID NO: 16), G3479 (SEQ ID NO: 18), and G3484 (SEQ ID NO: 26) and G3980 (SEQ ID NO: 10). 35S::G3484 *Arabidopsis* lines also exhibited a delay in the abscission of floral organs, following pollination, as was noted with G1760. Such a trait comprising enhanced floral organ retention would have potential utility in ornamental species and could prolong the period of bloom or shelf life of cut-flowers. G152, G3981, and G3480 have not yet been shown to confer early flowering in *Arabidopsis* plants.

Thus, a number of potentially valuable traits may be conferred by G1760 and its closely related sequences found in Table 1. Morphological and physiological improvements can be conferred to crop plants such as, for example, soy, cotton, corn, ornamentals, and plants grown as biofuel feedstocks, including increased yield, increased tolerance to low nitrogen conditions, increased tolerance to cold, and/or increased tolerance to hyperosmotic stress, such as drought or other forms of water deprivation.

Example IX. Transformation of Dicots to Produce Increased Yield and/or Abiotic Stress Tolerance Crop species that overexpress polypeptides of the invention may produce plants with increased water deprivation tolerance, cold and/or nutrient tolerance and/or yield in both stressed and non-stressed conditions. Thus, polynucleotide sequences listed in the Sequence Listing recombined into, for example, one of the nucleic acid constructs of the invention, or another suitable expression construct or delivery system, may be introduced into a plant for the purpose of modifying plant traits for the purpose of improving yield and/or quality. The nucleic acid construct may contain a constitutive, tissue-specific or inducible promoter operably linked to the polynucleotide. The nucleic acid construct may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach, 1989; Gelvin et al., 1990; Herrera-Estrella et al., 1983; Bevan, 1984; and Klee, 1985). Methods for analysis of traits are routine in the art and examples are disclosed above.

Numerous protocols for the transformation of eudicots, for example, tomato, cotton and soy plants, have been previously described, and are well known in the art. Gruber et al., 1993, in Glick and Thompson, 1993, describe several expression vectors and culture methods that may be used for cell or tissue transformation and subsequent regeneration. For soybean transformation, methods are described by Miki et al., 1993; and U.S. Pat. No. 5,563,055 to Townsend and Thomas. See also U.S. Pat. Nos. 6,624,344, 6,620,990, and 6,573,437, to Rangan, Anderson et al., U.S. Pat. No. 6,479,287 to Reichert et al., and U.S. Pat. No. 6,483,013 to Reynaerts et al., which all describe cotton transformation.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 to Christou et al.; and U.S. Pat. No. 5,322,783 to Tomes et al).

Alternatively, sonication methods (see, for example, Zhang et al., 1991); direct uptake of DNA into protoplasts using $CaCl_2$ precipitation, polyvinyl alcohol or poly-L-ornithine (see, for example, Hain et al., 1985; Draper et al., 1982); liposome or spheroplast fusion (see, for example, Deshayes et al., 1985; Christou et al., 1987; and electroporation of protoplasts and whole cells and tissues (see, for example, Donn et al., 1990; D'Halluin et al., 1992; and Spencer et al., 1994) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al., 1986, and in Vos, et al., U.S. Pat. No. 6,613,962, the latter method described in brief here. Eight day old cotyledon explants are precultured for 24 hours in Petri dishes containing a feeder layer of suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing a nucleic acid construct comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, Townsend et al., U.S. Pat. No. 5,563,055, described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the nucleic acid construct comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see Townsend et al., U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example X: Transformation of Monocots to Produce Increased Yield or Abiotic Stress Tolerance Cereal plants such as, but not limited to, corn, wheat, rice, sorghum, or barley, or grasses such as switchgrass or *Miscanthus*, may be transformed with the present polynucleotide sequences, including monocot or eudicot-derived sequences such as those presented in the present Tables, cloned into a nucleic acid construct, and expressed constitutively under, for example, the rice actin, tubulin or rab17 promoters, or with tissue-specific or inducible promoters. The expression constructs may be one found in the Sequence Listing, or any other suitable construct may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The nucleic acid construct may be introduced into a variety of cereal plants by means well known in the art including direct DNA transfer or *Agrobacterium tumefaciens*-mediated transformation. The latter approach may be accomplished by a variety of means, including, for example, that of Hiei, U.S. Pat. No. 5,591,616, in which monocotyledon callus is transformed by contacting dedifferentiating tissue with the *Agrobacterium* containing the nucleic acid construct.

The sample tissues are immersed in a suspension of $3 \times 10^{-9}$ cells of *Agrobacterium* containing the nucleic acid construct for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1990, wheat, Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). For transforming corn embryogenic cells derived from immature scutellar tissue using microprojectile bombardment, the A188XB73 genotype is the preferred genotype (Fromm et al., 1990; Gordon-Kamm et al., 1990). After microprojectile bombardment the tissues are selected on phosphinothricin to identify the transgenic embryogenic cells (Gordon-Kamm et al., 1990). Transgenic plants are regenerated by standard corn regeneration techniques (Fromm et al., 1990; Gordon-Kamm et al., 1990).

Example XI: Increased Yield or Abiotic Stress Tolerance in Non-*Arabidopsis* Species It is expected that structurally similar orthologs of the G1760 clade of polypeptide sequences, including those found in the Sequence Listing, can confer increased yield or increased tolerance to a number of abiotic stresses, including water deprivation, osmotic stress, cold, and/or low nitrogen conditions, relative to control plants. As sequences of the invention have been shown to reduce stress symptoms and/or improve abiotic stress tolerance in several diverse plant species, it is also expected that these sequences will increase yield of crop or other commercially important plant species.

Northern blot analysis, RT-PCR or microarray analysis of the regenerated, transformed plants may be used to show expression of a polypeptide or the invention and related genes that are capable of inducing abiotic stress tolerance, and/or larger size.

After a eudicot plant, monocot plant or plant cell has been transformed (and the latter regenerated into a plant) with a G1760 clade member sequence, such as SEQ ID NOs: 1, 3, 5, 7, 9, 11, 13, 15, 17, 19, 21, 23, 25, 27, 29, or 31, or a nucleotide sequence encoding SEQ ID NOs: 2, 4, 6, 8, 10, 12, 14, 16, 18, 20, 22, 24, 26, 28, 30 or 32, or a nucleotide sequence encoding a polypeptide comprising a MADS domain of SEQ ID NOs: 33-48, or a sequence that is phylogenetically-related and closely-related to one of these sequences, may be shown to confer increased tolerance to abiotic stress, or produce greater yield relative to a control plant under the stress conditions, or produce greater yield that the control plant under non-stressed conditions. The transformed monocot plant may also be crossed with itself or a plant from the same line, a non-transformed or wild-type monocot plant, or another transformed monocot plant from a different transgenic line of plants.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing abiotic stress tolerance) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and eudicot plants, and those derived from dicots (e.g., the *Arabidopsis* and soy genes) may be used to transform either group, although it is expected that some of these sequences will function best if the gene is transformed into a plant from the same group as that from which the sequence is derived.

As an example of a first step to determine water deprivation-related tolerance, seeds of these transgenic plants may be subjected to germination assays to measure sucrose sensing, severe desiccation or drought. Examples of methods for sucrose sensing, severe desiccation or drought assays are described above. Plants overexpressing sequences of the invention may be found to be more tolerant to high sucrose by having better germination, longer radicles, and more cotyledon expansion.

Sequences of the invention, that is, members of the G1760 clade, may also be used to generate transgenic plants that are more tolerant to low nitrogen conditions or cold than control plants. As an example of a first step to determine increased cold or low-nitrogen tolerance, seeds of these transgenic plants may be subjected to germination assays to measure low nitrogen tolerance, altered C/N sensing, or cold tolerance. Examples of these methods are described above. Plants overexpressing sequences of the invention may be found to be more tolerant to cold or low nitrogen by having better germination, or superior growth characteristics, as compared to control plants, under these conditions.

Plants that are more tolerant than controls to water deprivation assays, low nitrogen conditions or cold are greener, more vigorous will have better survival rates than controls, or will recover better from these treatments than control plants.

It is expected that the same methods may be applied to identify other useful and valuable sequences of the present polypeptide clades, and the sequences may be derived from a diverse range of species.

REFERENCES CITED

Aldemita and Hodges (1996) *Planta* 199: 612-617
Alia et al. (1998) *Plant J.* 16: 155-161
Altschul (1990) *J. Mol. Biol.* 215: 403-410
Altschul (1993) *J. Mol. Evol.* 36: 290-300
Alvarez-Buylla et al. (2000) *Plant J.* 24:457-466
Anderson and Young (1985) "Quantitative Filter Hybridisation", In: Hames and Higgins, ed., *Nucleic Acid Hybridisation, A Practical Approach*. Oxford, IRL Press, 73-111
Ausubel et al. (1997) Short Protocols in Molecular Biology, John Wiley & Sons, New York, N.Y., unit 7.7
Bairoch et al. (1997) *Nucleic Acids Res.* 25: 217-221
Bates et al. (1973) *Plant Soil* 39: 205-207
Battaglia et al. (2006) Mech. Dev. 123: 267-276
Bechtold and Pelletier (1998) *Methods Mol. Biol.* 82: 259-266
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattacharjee et al. (2001) *Proc. Natl. Acad. Sci. USA* 98: 13790-13795
Borevitz et al. (2000) *Plant Cell* 12: 2383-2393
Boss and Thomas (2002) *Nature,* 416: 847-850
Bruce et al. (2000) *Plant Cell* 12: 65-79
Cassas et al. (1993) *Proc. Natl. Acad. Sci. USA* 90: 11212-11216
Chase et al. (1993) *Ann. Missouri Bot. Gard.* 80: 528-580
Cheikh et al. (2003) U.S. Patent Application No. 20030101479
Christou et al. (1987) *Proc. Natl. Acad. Sci. USA* 84: 3962-3966
Christou (1991) *Bio/Technol.* 9:957-962
Christou et al. U.S. Pat. No. 5,015,580, issued May 14, 1991
Christou et al. (1992) *Plant. J.* 2: 275-281
Coruzzi et al. (2001) *Plant Physiol.* 125: 61-64
Coupland (1995) *Nature* 377: 482-483
Daly et al. (2001) *Plant Physiol.* 127: 1328-1333
Davies et al. (1996) (1998) *Methods Mol. Biol.* 82: 259-266
De Blaere et al. (1987) *Meth. Enzymol.* 143:277)
Deshayes et al. (1985) *EMBO J.,* 4: 2731-2737
D'Halluin et al. (1992) *Plant Cell* 4: 1495-1505
Donn et al. (1990) in *Abstracts of VIIth International Congress on Plant Cell and Tissue Culture IAPTC*, A2-38: 53
Doolittle, ed. (1996) *Methods in Enzymology*, vol. 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Str. Biol.* 6: 361-365
Eisen (1998) *Genome Res.* 8: 163-167
Feng and Doolittle (1987) *J. Mol. Evol.* 25: 351-360
Fernandez et al. (2000) *Plant Cell* 12: 183-198
Filleur et al. (2005) *Biochem. Soc. Trans.* 33: 283-286
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gan et al. (2005) *Planta* 222: 730-742
Glick and Thompson, eds. (1993) *Methods in Plant Molecular Biology and Biotechnology*. CRC Press., Boca Raton, Fla.
Gelvin et al. (1990) *Plant Molecular Biology Manual*, Kluwer Academic Publishers
Glantz (2001) Relative risk and risk score, in Primer of Biostatistics. $5^{th}$ ed., McGraw Hill/Appleton and Lange, publisher.
Gilmour et al. (1998) *Plant J.* 16: 433-442
Gruber et al., in Glick and Thompson (1993) *Methods in Plant Molecular Biology and Biotechnology*. eds., CRC Press, Inc., Boca Raton
Goodrich et al. (1993) *Cell* 75: 519-530
Gordon-Kamm et al. (1990) *Plant Cell* 2: 603-618
Haake et al. (2002) *Plant Physiol.* 130: 639-648
Hain et al. (1985) *Mol. Gen. Genet.* 199: 161-168
Haymes et al. (1985) *Nucleic Acid Hybridization: A Practical Approach*, IRL Press, Washington, D.C.
He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) *Nucleic Acids Res.* 19: 6565-6572
Hepworth et al. (2002). *EMBO J.* 21: 4327-4337
Herrera-Estrella et al. (1983) *Nature* 303: 209
Hiei et al. (1994) *Plant J.* 6:271-282
Hiei, U.S. Pat. No. 5,591,616, issued 7 Jan. 1997
Hiei et al. (1997) *Plant Mol. Biol.* 35:205-218
Higgins and Sharp (1988) *Gene* 73: 237-244
Higgins et al. (1996) *Methods Enzymol.* 266: 383-402

Honma and Goto (2001) *Nature* 409: 525-529
Hosmer and Lemeshow (1999) Applied Survival Analysis: regression Modeling of Time to Event Data. John Wiley & Sons, Inc. Publisher.
Huang et al. (1996) Plant Cell 8: 81-94
Immink et al. (2002) *Proc. Natl. Acad. Sci. U.S.A* 99: 2416-2421
Ishida (1990) *Nature Biotechnol.* 14:745-750
Jaglo et al. (2001) *Plant Physiol.* 127: 910-917
Jang et al. (1997) *Plant Cell* 9: 5-19
Kashima et al. (1985) *Nature* 313: 402-404
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Klein et al. (1987); U.S. Pat. No. 4,945,050
Koornneef et al. (1986) In *Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Leon-Kloosterziel et al. (1996) *Plant Physiol.* 110: 233-240
Lim et al. (2000) Plant Mol. Biol. 44: 513-527
Lin et al. (1991) Nature 353: 569-571
Liu and Zhu (1997) *Proc. Natl. Acad. Sci. USA* 94: 14960-14964
Mandel (1992a) Nature 360: 273-277
Mandel et al. (1992b) *Cell* 71-133-143
Meyers (1995) Molecular Biology and Biotechnology, Wiley VCH, New York, N.Y., p 856-853
Miki et al. (1993) in *Methods in Plant Molecular Biology and Biotechnology*, p. 67-88, Glick and Thompson, eds., CRC Press, Inc., Boca Raton
Mount (2001), in *Bioinformatics: Sequence and Genome Analysis*, Cold Spring Harbor Laboratory Press, Cold Spring Harbor, N.Y., p. 543
Müller et al. (2001) *Plant J.* 28: 169-179
Nandi et al. (2000) *Curr. Biol.* 10: 215-218
Peng et al. (1997) *Genes Development* 11: 3194-3205)
Peng et al. (1999) *Nature* 400: 256-261
Porra et al. (1989) Biochim. Biophys. Acta: 975, 384-394
Pourtau et al., (2004) *Planta* 219: 765-772
Ratcliffe et al. (2001) *Plant Physiol.* 126: 122-132
Ratcliffe, et al. (2003) *Plant Cell* 15: 1159-1169
Reeves and Nissen (1995) *Prog. Cell Cycle Res.* 1: 339-349
Remans et al. (2006) *Proc. Natl. Acad. Sci. U.S.A* 103: 19206-19211
Riechmann et al. (1996) *Proc. Natl. Acad. Sci. U.S.A* 93, 4793-4798
Riechmann and Meyerowitz (1997) *Biol Chem* 378: 1079-1101
Riechmann et al. (2000a) *Science* 290, 2105-2110
Riechmann, J. L., and Ratcliffe, O. J. (2000b) *Curr. Opin. Plant Biol.* 3, 423-434
Rieger et al. (1976) *Glossary of Genetics and Cytogenetics: Classical and Molecular*, 4th ed., Springer Verlag, Berlin
Robson et al. (2001) *Plant J.* 28: 619-631
Sadowski et al. (1988) *Nature* 335: 563-564
Saleki et al. (1993) *Plant Physiol.* 101: 839-845
Sambrook et al. (1989) *Molecular Cloning: A Laboratory Manual*, 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shpaer (1997) Methods Mol. Biol. 70: 173-187
Smeekens (1998) *Curr. Opin. Plant Biol.* 1: 230-234
Smith et al. (1992) *Protein Engineering* 5: 35-51
Sonnhammer et al. (1997) *Proteins* 28: 405-420
Soltis et al. (1997) *Ann. Missouri Bot. Gard.* 84: 1-49
Spencer et al. (1994) *Plant Mol. Biol.* 24: 51-61
Stitt (1999) *Curr. Opin. Plant. Biol.* 2: 178-186
Suzuki et al. (2001) *Plant J.* 28: 409-418
Tang and Perry (2003) J. Biol. Chem. 278: 28154-28159
Thompson et al. (1994) *Nucleic Acids Res.* 22: 4673-4680
Tomes et al., U.S. Pat. No. 5,322,783, issued Jun. 21, 1994
Townsend and Thomas, U.S. Pat. No. 5,563,055, issued Oct. 8, 1996
Tudge (2000) in *The Variety of Life*, Oxford University Press, New York, N.Y. pp. 547-606
Vasil et al. (1992) *Bio/Technol.* 10:667-674
Vasil et al. (1993) *Bio/Technol.* 11:1553-1558
Vasil (1994) *Plant Mol. Biol.* 25: 925-937
Vos, et al. U.S. Pat. No. 6,613,962, issued Sep. 2, 2003
Wahl and Berger (1987) Methods Enzymol. 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology*, Academic Press
Wu et al. (1996) *Plant Cell* 8: 617-627
Xin and Browse (1998) *Proc. Natl. Acad. Sci. USA* 95: 7799-7804
Xu et al. (2001) *Proc. Natl. Acad. Sci. USA* 98: 15089-15094
Yang et al. (2003) *Plant J.* 33: 47-59
Zhang et al. (1991) *Bio/Technology* 9: 996-997
Zhang and Forde (2000) *J. Exp. Bot.* 51: 51-59
Zhu et al. (1998) *Plant Cell* 10: 1181-1191

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A transgenic plant transformed with a recombinant expression vector comprising a nucleic acid encoding a polypeptide having at least 95% amino acid sequence identity over the full-length of the amino acid sequence as set forth in SEQ ID NO: 10, wherein said nucleic acid is operably linked to a non-native promoter, wherein said polypeptide is overexpressed in said transformed plant, and wherein the transformed plant that overexpresses said polypeptide exhibits greater tolerance to hyperosmotic stress, greater tolerance to cold, greater tolerance to low nitrogen conditions, or early flowering relative to a control plant of the same plant species not comprising said recombinant expression vector.

2. The transgenic plant of claim 1, wherein said nucleic acid encodes the full-length polypeptide of SEQ ID NO:10.

3. The transgenic plant of claim 1, wherein expression of the polypeptide is regulated by a constitutive, inducible, or tissue-specific promoter.

4. The transgenic plant of claim 1, wherein the hyperosmotic stress comprises drought or 9.4% sucrose.

5. The transgenic plant of claim 1, wherein the transformed plant is a dicot.

6. The transgenic plant of claim 1, wherein the transformed plant is a legume.

7. A seed of the transgenic plant of claim 1, wherein said seed comprises the recombinant expression vector.

8. A method of producing a plant comprising the steps of:
 a) transforming plants with a recombinant expression vector comprising a nucleic acid encoding a polypeptide having at least 95% amino acid sequence identity over the full-length of the amino acid sequence as set forth in SEQ ID NO: 10, wherein said nucleic acid is operably linked to a non-native promoter, wherein said polypeptide is overexpressed in said transformed plants; and
 b) selecting a transformed plant from step a) which exhibits greater tolerance to hyperosmotic stress, greater tolerance to cold, greater tolerance to low nitrogen conditions, or early flowering relative to a control plant of the same plant species not comprising said recombinant expression vector.

9. The method of claim 8, wherein said nucleic acid encodes the full-length polypeptide of SEQ ID NO: 10.

10. The method of claim 8, wherein expression of the polypeptide is regulated by a constitutive, inducible, or tissue-specific promoter.

11. The method of claim 8, wherein the hyperosmotic stress comprises drought or 9.4% sucrose.

12. The method of claim 8, wherein the transformed plant is a dicot.

13. The method of claim 8, wherein the transformed plant is a legume.

* * * * *

SEQUENCE LISTING

```
<160> NUMBER OF SEQ ID NOS: 75

<210> SEQ ID NO 1
<211> LENGTH: 1038
<212> TYPE: DNA
<213> ORGANISM: Arabidopsis thaliana
<220> FEATURE:
<223> OTHER INFORMATION: G1760
```

<400> SEQUENCE: 1

```
ccctaaaaaa gagaagaacc agaggagatt caattagagg ataaaattga tgggaagagg      60
gaagattgtg atccaaagga tcgatgattc aacgagtaga caagtcactt tctccaaacg     120
aagaaagggc cttatcaaga aagccaaaga gctagctatt ctctgtgatg ccaggtcgg      180
tctcatcatc ttctctagca ccggaaagct ctatgacttt gcaagctcca gcatgaagtc     240
ggttattgat agatacaaca agagcaagat cgagcaacaa caactattga accccgcatc     300
agaagtcaag ttttggcaga gagaagctgc tgttctaaga caagaactgc atgctttgca     360
agaaaatcat cggcaaatga tgggagaaca gctaaatggt ttaagtgtta acgagctaaa     420
cagtcttgag aatcaaattg agataagttt gcgtggaatt cgtatgagaa aggaacaact     480
gttgactcaa gaaatccaag aactaagcca aagaggaat cttattcatc aggaaaacct      540
cgatttatct aggaaagtac aacggattca tcaagaaaat gtggagctct acaagaaggc     600
ttatatggca aacacaaacg ggtttacaca ccgtgaagta gctgttgcgg atgatgaatc     660
acacactcag attcggctgc aactaagcca gcctgaacat tccgattatg acactccacc     720
aagagcaaac gaataacaga gagattgaag ttggaagata ccatgatgtt gaagaacact     780
ccaaaggcct tggtttgaat aaggttcttg aactggaaac ctctatacac caagccacgt     840
acgataagca gcatggttct tctaacatag tcatattttc aatcctaaat ataattaaag     900
catatataat taaaatccgg tgttgttata ctcatcttga gtattaatat tgtacttgtt     960
tataaccata gattcgtcaa ttaatagaga aaaatcatat gaattattat ccaaaaaaaa    1020
aaaaaaaaaa aaaaaaaa                                                  1038
```

<210> SEQ ID NO 2
<211> LENGTH: 228
<212> TYPE: PRT
<213> ORGANISM: Arabidopsis thaliana
<220> FEATURE:
<223> OTHER INFORMATION: G1760 polypeptide

<400> SEQUENCE: 2

```
Met Gly Arg Gly Lys Ile Val Ile Gln Arg Ile Asp Asp Ser Thr Ser
1               5                   10                  15

Arg Gln Val Thr Phe Ser Lys Arg Arg Lys Gly Leu Ile Lys Lys Ala
            20                  25                  30

Lys Glu Leu Ala Ile Leu Cys Asp Ala Glu Val Gly Leu Ile Ile Phe
        35                  40                  45

Ser Ser Thr Gly Lys Leu Tyr Asp Phe Ala Ser Ser Ser Met Lys Ser
    50                  55                  60

Val Ile Asp Arg Tyr Asn Lys Ser Lys Ile Glu Gln Gln Gln Leu Leu
65                  70                  75                  80

Asn Pro Ala Ser Glu Val Lys Phe Trp Gln Arg Glu Ala Ala Val Leu
                85                  90                  95

Arg Gln Glu Leu His Ala Leu Gln Glu Asn His Arg Gln Met Met Gly
            100                 105                 110

Glu Gln Leu Asn Gly Leu Ser Val Asn Glu Leu Asn Ser Leu Glu Asn
        115                 120                 125

Gln Ile Glu Ile Ser Leu Arg Gly Ile Arg Met Arg Lys Glu Gln Leu
    130                 135                 140

Leu Thr Gln Glu Ile Gln Glu Leu Ser Gln Lys Arg Asn Leu Ile His
145                 150                 155                 160
```

```
Gln Glu Asn Leu Asp Leu Ser Arg Lys Val Gln Arg Ile His Gln Glu
            165                 170                 175

Asn Val Glu Leu Tyr Lys Lys Ala Tyr Met Ala Asn Thr Asn Gly Phe
        180                 185                 190

Thr His Arg Glu Val Ala Val Ala Asp Asp Glu Ser His Thr Gln Ile
    195                 200                 205

Arg Leu Gln Leu Ser Gln Pro Glu His Ser Asp Tyr Asp Thr Pro Pro
210                 215                 220

Arg Ala Asn Glu
225

<210> SEQ ID NO 3
<211> LENGTH: 959
<212> TYPE: DNA
<213> ORGANISM: Arabidopsis thaliana
<220> FEATURE:
<223> OTHER INFORMATION: G152

<400> SEQUENCE: 3
cctagaacgc accaagatct aaaggaagat caaaataggg tttaaattaa tggggagagg      60
gaagattgtg atccagaaga tcgatgattc cacgagtaga caagtcactt tctccaaaag    120
aagaaagggt ctcatcaaga aagctaaaga acttgctatt ctctgcgacg ccgaggtctg    180
tctcatcatt ttctccaaca ctgacaagct ctatgacttt gccagctcca gtgtgaaatc    240
tactattgaa cgattcaata cggctaagat ggaggagcaa gaactaatga accctgcatc    300
agaagttaag ttttggcaga gagaggctga aactctaagg caagaattgc actcattgca    360
agaaaattat cggcaactaa cgggagtgga attaaatggt ttgagcgtta aggagttaca    420
aaacatagag agtcaacttg aaatgagttt acgtggaatt cgtatgaaaa gggaacaaat    480
tttgaccaat gaaattaaag agctaaccag aaagaggaat cttgttcatc atgaaaacct    540
cgaattgtcg agaaaagtac aaaggattca tcaagaaaat gtcgaactat acaagaaggc    600
ttatggaacg tcgaacacaa atggattggg acatcatgag ctagtagatg cagtttatga    660
atcccatgca caggttaggc tgcagctaag ccagcctgag cagtcccatt ataagacatc    720
ttcaaacagc taagatcata taagagatat ataacaaatt gttcgttctt gattatctca    780
aaacccttc aaatatatat acgtgcatat tatatgaa gactcgtttg actatgtcaa     840
tatatatgtt tcatgcagg agtaagtgtg agtgtaatca tgtcggagag caaaccaaag    900
gtttgatttg tacgatatat acttatatat ggtctcaagt gaaagcaatg gaacagctt    959

<210> SEQ ID NO 4
<211> LENGTH: 227
<212> TYPE: PRT
<213> ORGANISM: Arabidopsis thaliana
<220> FEATURE:
<223> OTHER INFORMATION: G152 polypeptide

<400> SEQUENCE: 4

Met Gly Arg Gly Lys Ile Val Ile Gln Lys Ile Asp Asp Ser Thr Ser
1               5                   10                  15

Arg Gln Val Thr Phe Ser Lys Arg Arg Lys Gly Leu Ile Lys Lys Ala
            20                  25                  30

Lys Glu Leu Ala Ile Leu Cys Asp Ala Glu Val Cys Leu Ile Ile Phe
        35                  40                  45

Ser Asn Thr Asp Lys Leu Tyr Asp Phe Ala Ser Ser Ser Val Lys Ser
    50                  55                  60
```

Thr Ile Glu Arg Phe Asn Thr Ala Lys Met Glu Gln Glu Leu Met
 65                  70                  75                  80

Asn Pro Ala Ser Glu Val Lys Phe Trp Gln Arg Glu Ala Glu Thr Leu
                 85                  90                  95

Arg Gln Glu Leu His Ser Leu Gln Glu Asn Tyr Arg Gln Leu Thr Gly
             100                 105                 110

Val Glu Leu Asn Gly Leu Ser Val Lys Glu Leu Gln Asn Ile Glu Ser
         115                 120                 125

Gln Leu Glu Met Ser Leu Arg Gly Ile Arg Met Lys Arg Glu Gln Ile
130                 135                 140

Leu Thr Asn Glu Ile Lys Glu Leu Thr Arg Lys Arg Asn Leu Val His
145                 150                 155                 160

His Glu Asn Leu Glu Leu Ser Arg Lys Val Gln Arg Ile His Gln Glu
                165                 170                 175

Asn Val Glu Leu Tyr Lys Lys Ala Tyr Gly Thr Ser Asn Thr Asn Gly
            180                 185                 190

Leu Gly His His Glu Leu Val Asp Ala Val Tyr Glu Ser His Ala Gln
        195                 200                 205

Val Arg Leu Gln Leu Ser Gln Pro Glu Gln Ser His Tyr Lys Thr Ser
210                 215                 220

Ser Asn Ser
225

<210> SEQ ID NO 5
<211> LENGTH: 936
<212> TYPE: DNA
<213> ORGANISM: Antirrhinum majus
<220> FEATURE:
<223> OTHER INFORMATION: G3982

<400> SEQUENCE: 5

```
atttcatttg aagagatggg aagggggaag attgtgatcc aaagaatcga caaatcgacg    60
agtaggcaag tgactttttc gaaaaggagg agtggacttt tgaagaaggc caaagagctt   120
gctattcttt gtgatgcaga agttggagtt gttatatttt ccagcactgg gaagctctac   180
gaattttcaa gcaccagcat gaaatcaatt attgaacgac acactaaaac caaagaggac   240
catcatcagc tgcttaatca tggctcggag gtcaagtttt ggcaaaggga ggctgcgact   300
ttaaggcaac aattacagga tttgcaagaa accatcggag agttgatggg agaagagcta   360
caagggttga atgttgaaga tctacacaga ttggagaacc aactagagat gagtttgcga   420
ggcgtgcgca tgaaaaaggt acagatgtta accgatgagg ttcatgaact taggagaaag   480
ggacatctca tccatcaaga gaacaatgag ctctatgaga aggtaaaaact ccttcaacaa   540
gaaaacaagg aattgtgtaa aaaggcttac ggcacaaggg atgtaagtgc agcaaatgga   600
actgccttgg ttccatttgg tttcgcaatt ggtagggaac aattcgagcc aatccagctt   660
catttaagcc agcctgaacc agaaaatatt gaaacatcaa gagcctcagg atcaaagtaa   720
attattttg gactacctta caaaactaca tgtgcttgtg tatgtatcat ccagcactag   780
gcaattaagt aacttgtatt ttgaatgcac gcctagacat taatatttcc aaattgtcac   840
aatattcgac agagctttca tttggcgata cctgcaagaa aattcactgt actcaattta   900
agagttcata taatgctatg tgtaattgtt tttagc                             936
```

<210> SEQ ID NO 6
<211> LENGTH: 234
<212> TYPE: PRT

<213> ORGANISM: Antirrhinum majus
<220> FEATURE:
<223> OTHER INFORMATION: G3982 polypeptide

<400> SEQUENCE: 6

```
Met Gly Arg Gly Lys Ile Val Ile Gln Arg Ile Asp Lys Ser Thr Ser
1               5                   10                  15
Arg Gln Val Thr Phe Ser Lys Arg Arg Ser Gly Leu Leu Lys Lys Ala
            20                  25                  30
Lys Glu Leu Ala Ile Leu Cys Asp Ala Glu Val Gly Val Ile Phe
        35                  40                  45
Ser Ser Thr Gly Lys Leu Tyr Glu Phe Ser Ser Thr Ser Met Lys Ser
    50                  55                  60
Ile Ile Glu Arg His Thr Lys Thr Lys Glu Asp His His Gln Leu Leu
65                  70                  75                  80
Asn His Gly Ser Glu Val Lys Phe Trp Gln Arg Glu Ala Ala Thr Leu
                85                  90                  95
Arg Gln Gln Leu Gln Asp Leu Gln Glu Asn His Arg Lys Leu Met Gly
            100                 105                 110
Glu Glu Leu Gln Gly Leu Asn Val Glu Asp Leu His Arg Leu Glu Asn
        115                 120                 125
Gln Leu Glu Met Ser Leu Arg Gly Val Arg Met Lys Lys Val Gln Met
    130                 135                 140
Leu Thr Asp Glu Val His Glu Leu Arg Arg Lys Gly His Leu Ile His
145                 150                 155                 160
Gln Glu Asn Asn Glu Leu Tyr Glu Lys Val Lys Leu Leu Gln Gln Glu
                165                 170                 175
Asn Lys Glu Leu Cys Lys Lys Ala Tyr Gly Thr Arg Asp Val Ser Ala
            180                 185                 190
Ala Asn Gly Thr Ala Leu Val Pro Phe Gly Phe Ala Ile Gly Arg Glu
        195                 200                 205
Gln Phe Glu Pro Ile Gln Leu His Leu Ser Gln Pro Glu Pro Glu Asn
    210                 215                 220
Ile Glu Thr Ser Arg Ala Ser Gly Ser Lys
225                 230
```

<210> SEQ ID NO 7
<211> LENGTH: 1019
<212> TYPE: DNA
<213> ORGANISM: Glycine max
<220> FEATURE:
<223> OTHER INFORMATION: G3485

<400> SEQUENCE: 7

```
attcggctcg aagggcgctt tgtctgttat aatcaacgcg ctcctcacga gtgaatttct    60
ggttcggaag gatctgattg ttagggtttg gtatgggagg aggtaagatc gtgataagga   120
ggatcgacaa ttccacgagc aggcaagtga cgttctcgaa gcgaaggaac ggtttgctga   180
agaaggcgaa ggagcttgcg atcttgtgcg atgctgaagt cggagttatg atcttctcca   240
gcaccggaaa actctacgat ttcgccagct ccagcatgaa atcagtaatg gaccgataca   300
gcaaatcaaa agaagaacct tgtcaacttg ggagttcagc tctgaaatt aaattttggc    360
aaagggaggc agcaatgtta aggcaacaat tacacaattt gcaagaaagt caccgcagga   420
aaatgatggg ggaagaactg tcaggcttga cagtcaaaga attaccaaat ttggagaacc   480
aattagaaat tagccttcat ggtgtccgaa tgaaaaagga tcaacttta atgggtgaaa    540
```

```
tacaagagct aaatcgaaag ggaaacctca tacaccaaga aaatgtggaa ctgtataaga    600
aggtctatgg aacacaagat gataacgaaa caaacagaga ttctgttctc acaaatggtc    660
taggcatagg agaggatttg caagtgcctg tgaatctcca gctaagccag ccaagcacca    720
gcaacaacac tacaaggcac cttcaggaac tacaaaaatg ggcagattgc aattgcattg    780
atccatatac aggatgcgtg tgtttcacaa ttgctatcaa gaaaaatgga ctcagattta    840
aacctcgatg tcttcgtata aatgttgtgg catatagacc acagacaaat tggcttaaag    900 atttttaattt gaaattatca gaaaagaaa aggcaaccct agcatgtatg taagaaacaa    960
tgaaagcatc ttatgagaaa ccaagactca aatcaaggaa gaaattcttc cacccgccc   1019
```

<210> SEQ ID NO 8
<211> LENGTH: 286
<212> TYPE: PRT
<213> ORGANISM: Glycine max
<220> FEATURE:
<223> OTHER INFORMATION: G3485 polypeptide

<400> SEQUENCE: 8

```
Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Val Met Ile Phe
        35                  40                  45

Ser Ser Thr Gly Lys Leu Tyr Asp Phe Ala Ser Ser Ser Met Lys Ser
    50                  55                  60

Val Met Asp Arg Tyr Ser Lys Ser Lys Glu Glu Pro Cys Gln Leu Gly
65                  70                  75                  80

Ser Ser Ala Ser Glu Ile Lys Phe Trp Gln Arg Glu Ala Ala Met Leu
                85                  90                  95

Arg Gln Gln Leu His Asn Leu Gln Glu Ser His Arg Arg Lys Met Met
            100                 105                 110

Gly Glu Glu Leu Ser Gly Leu Thr Val Lys Glu Leu Pro Asn Leu Glu
        115                 120                 125

Asn Gln Leu Glu Ile Ser Leu His Gly Val Arg Met Lys Lys Asp Gln
    130                 135                 140

Leu Leu Met Gly Glu Ile Gln Glu Leu Asn Arg Lys Gly Asn Leu Ile
145                 150                 155                 160

His Gln Glu Asn Val Glu Leu Tyr Lys Lys Val Tyr Gly Thr Gln Asp
                165                 170                 175

Asp Asn Glu Thr Asn Arg Asp Ser Val Leu Thr Asn Gly Leu Gly Ile
            180                 185                 190

Gly Glu Asp Leu Gln Val Pro Val Asn Leu Gln Leu Ser Gln Pro Ser
        195                 200                 205

Thr Ser Asn Asn Thr Thr Arg His Leu Gln Glu Leu Gln Lys Trp Ala
    210                 215                 220

Asp Cys Asn Cys Ile Asp Pro Tyr Thr Gly Cys Val Cys Phe Thr Ile
225                 230                 235                 240

Ala Ile Lys Lys Asn Gly Leu Arg Phe Lys Pro Arg Cys Leu Arg Ile
                245                 250                 255

Asn Val Val Ala Tyr Arg Pro Gln Thr Asn Trp Leu Lys Asp Phe Asn
            260                 265                 270

Leu Lys Leu Ser Glu Lys Glu Lys Ala Thr Leu Ala Cys Met
        275                 280                 285
```

```
<210> SEQ ID NO 9
<211> LENGTH: 687
<212> TYPE: DNA
<213> ORGANISM: Glycine max
<220> FEATURE:
<223> OTHER INFORMATION: G3980

<400> SEQUENCE: 9
atggggagag gtaagatcgt gataaggagg atcgacaatt ccacgagcag gcaagtgacg      60
ttctcgaagc gaaggaacgg tttgctgaag aaggcgaagg agcttgcgat cttgtgcgat     120
gctgaagtcg gagttatgat cttctccagc accggaaaac tctacgattt cgccagctcc     180
agcatgaaat cagtaatgga ccgatacagc aaatcaaaag aagaaccttg tcaacttggg     240
agttcagcct ctgaaattaa gttttggcaa agggaggcag caatgttaag gcaacaatta     300
cacaatttgc aagaaagtca ccgcaggaaa atgatggggg aagaactgtc aggcttgaca     360
gtcaaagaat acaaaatttt ggagaaccaa ttagaaatta gccttcatgg tgtccgaatg     420
aaaaaggatc aacttttaat gggtgaaata caagagctaa atcgaaaggg aaacctcata     480
caccaagaaa atgtggaact gtataagaag gtctatggaa cacaagatga taacgaaaca     540
aacagagatt ctgttctgac aaatggtcta ggcataggag aggatttgca agtgcctgtg     600
aatctccagc taagccagcc acagcaacag caacaacact acaaggcatc ttcaggaact     660
acaaaattgg gattgcaatt gcattga                                        687

<210> SEQ ID NO 10
<211> LENGTH: 228
<212> TYPE: PRT
<213> ORGANISM: Glycine max
<220> FEATURE:
<223> OTHER INFORMATION: G3980 polypeptide

<400> SEQUENCE: 10

Met Gly Arg Gly Lys Ile Val Ile Arg Arg Ile Asp Asn Ser Thr Ser
1               5                  10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Val Met Ile Phe
        35                  40                  45

Ser Ser Thr Gly Lys Leu Tyr Asp Phe Ala Ser Ser Ser Met Lys Ser
    50                  55                  60

Val Met Asp Arg Tyr Ser Lys Ser Lys Glu Glu Pro Cys Gln Leu Gly
65                  70                  75                  80

Ser Ser Ala Ser Glu Ile Lys Phe Trp Gln Arg Glu Ala Ala Met Leu
                85                  90                  95

Arg Gln Gln Leu His Asn Leu Gln Glu Ser His Arg Arg Lys Met Met
            100                 105                 110

Gly Glu Glu Leu Ser Gly Leu Thr Val Lys Leu Gln Asn Leu Glu
        115                 120                 125

Asn Gln Leu Glu Ile Ser Leu His Gly Val Arg Met Lys Lys Asp Gln
    130                 135                 140

Leu Leu Met Gly Glu Ile Gln Glu Leu Asn Arg Lys Gly Asn Leu Ile
145                 150                 155                 160

His Gln Glu Asn Val Glu Leu Tyr Lys Lys Val Tyr Gly Thr Gln Asp
                165                 170                 175

Asp Asn Glu Thr Asn Arg Asp Ser Val Leu Thr Asn Gly Leu Gly Ile
```

```
                    180                 185                 190
Gly Glu Asp Leu Gln Val Pro Val Asn Leu Gln Leu Ser Gln Pro Gln
            195                 200                 205

Gln Gln Gln Gln His Tyr Lys Ala Ser Ser Gly Thr Thr Lys Leu Gly
        210                 215                 220

Leu Gln Leu His
225

<210> SEQ ID NO 11
<211> LENGTH: 678
<212> TYPE: DNA
<213> ORGANISM: Glycine max
<220> FEATURE:
<223> OTHER INFORMATION: G3981

<400> SEQUENCE: 11
atggggagag gtaagatcgt gataaggagg atcgacaatt ccacgagcag gcaagtgacg    60
ttctcgaagc gaaggaacgg tttgctgaag aaggcgaagg agcttgcgat cttgtgcgat   120
gctgaagtcg gagttatgat cttctccagc accggaaaac tctacgattt cgccagctcc   180
agcatgaaat cagtaatgga ccgatacagc aaatcaaaag aagaaccttg tcaacttggg   240
agttcagcct ctgaaattaa gttttggcaa agggaggcag caatgttaag gcaacaatta   300
cacaatttgc aagaaagtca ccggaaaatg atggggaag aactgtcagg cttgacagtc   360
aaagaattac aaaatttgga gaaccaatta gaaattagcc ttcgaggtgt ccgaatgaaa   420
aaggatcaac ttttaatgga tgaaatacaa gagttaaatc ggaagggaaa cctcatacac   480
caagaaaatg tggaactgta tcagaaggtc tatggaacaa aagatgataa caaaacaaac   540
agagattctg ttctcacaaa tggtctaggc ataggagagg attggcaagt gcctgtgaat   600
ctccagctaa gccagccaca gcaacaacac tacaaggaac cttcaggaac acaaaaattg   660
ggattgcaat tgcattag                                                  678

<210> SEQ ID NO 12
<211> LENGTH: 225
<212> TYPE: PRT
<213> ORGANISM: Glycine max
<220> FEATURE:
<223> OTHER INFORMATION: G3981 polypeptide

<400> SEQUENCE: 12

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Val Met Ile Phe
        35                  40                  45

Ser Ser Thr Gly Lys Leu Tyr Asp Phe Ala Ser Ser Ser Met Lys Ser
    50                  55                  60

Val Met Asp Arg Tyr Ser Lys Ser Lys Glu Glu Pro Cys Gln Leu Gly
65                  70                  75                  80

Ser Ser Ala Ser Glu Ile Lys Phe Trp Gln Arg Glu Ala Ala Met Leu
                85                  90                  95

Arg Gln Gln Leu His Asn Leu Gln Glu Ser His Arg Lys Met Met Gly
            100                 105                 110

Glu Glu Leu Ser Gly Leu Thr Val Lys Glu Leu Gln Asn Leu Glu Asn
        115                 120                 125
```

```
Gln Leu Glu Ile Ser Leu Arg Gly Val Arg Met Lys Lys Asp Gln Leu
        130                 135                 140

Leu Met Asp Glu Ile Gln Glu Leu Asn Arg Lys Gly Asn Leu Ile His
145                 150                 155                 160

Gln Glu Asn Val Glu Leu Tyr Gln Lys Val Tyr Gly Thr Lys Asp Asp
                165                 170                 175

Asn Lys Thr Asn Arg Asp Ser Val Leu Thr Asn Gly Leu Gly Ile Gly
            180                 185                 190

Glu Asp Leu Gln Val Pro Val Asn Leu Gln Leu Ser Gln Pro Gln Gln
        195                 200                 205

Gln His Tyr Lys Glu Pro Ser Gly Thr Thr Lys Leu Gly Leu Gln Leu
    210                 215                 220

His
225

<210> SEQ ID NO 13
<211> LENGTH: 1098
<212> TYPE: DNA
<213> ORGANISM: Arabidopsis thaliana
<220> FEATURE:
<223> OTHER INFORMATION: G153

<400> SEQUENCE: 13
aaaaaaaaga agcttctcct cttcctctgc cttcttcttt ccatttattg caaaccctga      60
tcaattggtt ttggtgttag tcttttgggg agagagatgg ggagagggaa gatagttata     120
cgaaggatcg ataactctac aagtagacaa gtgactttct ccaagagaag gagtggtttg     180
cttaagaaag ctaaagagtt atcgatcctt tgtgatgcag aagttggtgt tatcatattc     240
tctagcaccg gaaagctcta cgactacgca agcaattcaa gtatgaaaac aatcattgag     300
cggtacaaca gagtaaaaga ggagcagcat caacttctga atcatgcctc agagataaag     360
ttttggcaaa gagaggttgc aagtttgcag cagcagctcc aatatctaca gaatgccac      420 aggaaactag tgggagagga ctttctggaa tgaatgcta cgacctaca aaaccttgaa      480 gaccagctag taacaagtct aaaaggtgtt cgtctcaaaa aggatcaact tatgacaaat     540
gaaatcagag aacttaatcg taaggacaa atcatccaaa aagagaatca cgagctacaa     600 atattgtag atataatgcg taaggaaaat attaaattgc aaaagaaggt tcatggaaga     660
acaaatgcga ttgaaggcaa ttcaagtgta gatccaataa gcaatggaac acaacatat     720 gcaccaccgc aacttcaact catacaacta caaccagctc ctagagaaaa atcaatcaga     780
ctagggctac aactttccta gcaaaacatg tgggacatcg aacaatatac gaaaagagtt     840
tgtatgtcat cttcagtaac aaccaagctg gatcatttca ttcttggtta tgtaattctg     900
tttactactt tggagtttaa tatgttatat gacaagtttc tctttgtcaa gttacttgtg     960
tatgtacatc ataaaataat gatgtgatgt gagtgccgaa catactagac atcattttac    1020
cgtgtgtttt tttcgggtac attaaatgta caaaatccag tctaattggc attttttatac    1080 aaaaaaaaaa aaaaaaaa                                                  1098

<210> SEQ ID NO 14
<211> LENGTH: 234
<212> TYPE: PRT
<213> ORGANISM: Arabidopsis thaliana
<220> FEATURE:
<223> OTHER INFORMATION: G153 polypeptide

<400> SEQUENCE: 14
```

```
Met Gly Arg Gly Lys Ile Val Ile Arg Ile Asp Asn Ser Thr Ser
1               5                   10                  15

Arg Gln Val Thr Phe Ser Lys Arg Arg Ser Gly Leu Leu Lys Lys Ala
            20                  25                  30

Lys Glu Leu Ser Ile Leu Cys Asp Ala Glu Val Gly Val Ile Ile Phe
        35                  40                  45

Ser Ser Thr Gly Lys Leu Tyr Asp Tyr Ala Ser Asn Ser Ser Met Lys
    50                  55                  60

Thr Ile Ile Glu Arg Tyr Asn Arg Val Lys Glu Gln His Gln Leu
65                  70                  75                  80

Leu Asn His Ala Ser Glu Ile Lys Phe Trp Gln Arg Glu Val Ala Ser
                85                  90                  95

Leu Gln Gln Gln Leu Gln Tyr Leu Gln Glu Cys His Arg Lys Leu Val
            100                 105                 110

Gly Glu Glu Leu Ser Gly Met Asn Ala Asn Asp Leu Gln Asn Leu Glu
        115                 120                 125

Asp Gln Leu Val Thr Ser Leu Lys Gly Val Arg Leu Lys Lys Asp Gln
    130                 135                 140

Leu Met Thr Asn Glu Ile Arg Glu Leu Asn Arg Lys Gly Gln Ile Ile
145                 150                 155                 160

Gln Lys Glu Asn His Glu Leu Gln Asn Ile Val Asp Ile Met Arg Lys
                165                 170                 175

Glu Asn Ile Lys Leu Gln Lys Lys Val His Gly Arg Thr Asn Ala Ile
            180                 185                 190

Glu Gly Asn Ser Ser Val Asp Pro Ile Ser Asn Gly Thr Thr Thr Tyr
        195                 200                 205

Ala Pro Pro Gln Leu Gln Leu Ile Gln Leu Gln Pro Ala Pro Arg Glu
    210                 215                 220

Lys Ser Ile Arg Leu Gly Leu Gln Leu Ser
225                 230

<210> SEQ ID NO 15
<211> LENGTH: 1210
<212> TYPE: DNA
<213> ORGANISM: Arabidopsis thaliana
<220> FEATURE:
<221> NAME/KEY: misc_feature
<222> LOCATION: (1194)..(1196)
<223> OTHER INFORMATION: n is a, c, g, or t
<220> FEATURE:
<223> OTHER INFORMATION: G860

<400> SEQUENCE: 15
acaaaaccac atctctgaac tgaaccaatt tctcttctcc cccttccggt tatcggatta      60
ccagatctcg tttcccgcga tctagtttat tctttgaaaa agtgatagaa gcagaaatgg     120 gaagggcaa gatcgcgatt aagaggatca ataactctac gagccgtcag gttacgttct      180
cgaagcgaag gaatggattg ttgaagaaag ctaaggagct tgcgattctc tgcgatgctg     240
aggttggtgt catcatcttc tccagcaccg gtaggctcta cgatttctcc agctccagca     300
tgaaatcggt catagagaga tacagcgatg ccaaaggaga aaccagttca gaaaatgatc     360
ccgcttcaga aattcagttc tggcaaaagg aggctgcgat tctaaagcgt cagctacata     420
acttgcaaga aaaccaccgg caaatgatgg gggaggagct ctctggacta agtgtagaag     480
ctttacagaa tttggaaaat cagcttgaat tgagccttcg tggcgttcga atgaaaaagg     540
atcaaatgtt aatcgaagaa atacaagtac ttaaccgaga ggggaatctc gttcaccaag     600
```

```
agaatttaga cctccacaag aaagtaaacc taatgcacca acagaacatg aactacatg    660 aaaaggtttc agaggtcgag ggtgtgaaaa tcgcaaacaa gaattctctt ctcacaaatg    720
gtctagacat gagagatacc tcgaacgaac atgtccatct tcagctcagc caaccgcagc    780
atgatcatga gacgcattca aaagctatcc aactcaacta ttttccttc attgcataat     840 ataattcggt gtgccaacac acttatgttg acctcgtcgg aatcatatca caattcactg    900
tgtcagcttg cctctgcata agcgaaaata aaaacataaa catgatcagt ttgcattcca    960
tatctatcaa acaccagctt tgtaactttt aaaactttt ctccgtgcaa agacctttgg    1020
tttggcgctt aagcatgtag tttgatgatc aaaggaaatg ggtgttttag cataaagttg   1080
tcacccttcc gttgcatttt agcttcccat ccaaatcaat ttgtaaaatg tgagttagtt   1140
tgcagcatga aagctgatta aatatcagtc ccgttatcac aagaggtaaa aaannnaaaa   1200
aaaaaaaaaa                                                          1210
```

<210> SEQ ID NO 16
<211> LENGTH: 240
<212> TYPE: PRT
<213> ORGANISM: Arabidopsis thaliana
<220> FEATURE:
<223> OTHER INFORMATION: G860 polypeptide

<400> SEQUENCE: 16

```
Met Gly Arg Gly Lys Ile Ala Ile Lys Arg Ile Asn Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Val Ile Ile Phe
        35                  40                  45

Ser Ser Thr Gly Arg Leu Tyr Asp Phe Ser Ser Ser Met Lys Ser
    50                  55                  60

Val Ile Glu Arg Tyr Ser Asp Ala Lys Gly Glu Thr Ser Ser Glu Asn
65                  70                  75                  80

Asp Pro Ala Ser Glu Ile Gln Phe Trp Gln Lys Glu Ala Ala Ile Leu
                85                  90                  95

Lys Arg Gln Leu His Asn Leu Gln Glu Asn His Arg Gln Met Met Gly
            100                 105                 110

Glu Glu Leu Ser Gly Leu Ser Val Glu Ala Leu Gln Asn Leu Glu Asn
        115                 120                 125

Gln Leu Glu Leu Ser Leu Arg Gly Val Arg Met Lys Lys Asp Gln Met
    130                 135                 140

Leu Ile Glu Glu Ile Gln Val Leu Asn Arg Glu Gly Asn Leu Val His
145                 150                 155                 160

Gln Glu Asn Leu Asp Leu His Lys Lys Val Asn Leu Met His Gln Gln
                165                 170                 175

Asn Met Glu Leu His Glu Lys Val Ser Glu Val Glu Gly Val Lys Ile
            180                 185                 190

Ala Asn Lys Asn Ser Leu Leu Thr Asn Gly Leu Asp Met Arg Asp Thr
        195                 200                 205

Ser Asn Glu His Val His Leu Gln Leu Ser Gln Pro Gln His Asp His
    210                 215                 220

Glu Thr His Ser Lys Ala Ile Gln Leu Asn Tyr Phe Ser Phe Ile Ala
225                 230                 235                 240
```

<210> SEQ ID NO 17

<211> LENGTH: 736
<212> TYPE: DNA
<213> ORGANISM: Oryza sativa
<220> FEATURE:
<223> OTHER INFORMATION: G3479

<400> SEQUENCE: 17

```
aatccagctg agatcgatcg atcgatcgat ggggaggggc aagatagtga tccggcggat      60
cgacaactcg acgagccggc aggtgacgtt ctcgaagcgg cgcaacggga tcttcaagaa     120
ggccaaggag ctggccatcc tgtgcgacgc cgaggtcggc ctcgtcatct tctccagcac     180
cggccgcctc tacgagtatg ccagcaccag catgaagtca gtgattgatc gatatgggcg     240
agctaaggag gagcagcagc acgtcgcaaa ccccaactcg gagctgaagt tctggcaaag     300
ggaggcagca agcttgagac aacaactgca cagcttgcaa gaaaatcatc ggcagttgat     360
ggggcaagat ctttctggat tgggtgtcaa ggaactgcaa actctagaaa atcagctaga     420
aatgagcata cgctgcatcc ggacaaaaaa ggaccagctc atgattgatg aaatccacga     480
actgaatcga aagggaagtc tcatccacca agaaaacatg gaactgtaca gaaaggtcaa     540
cctgattcgc caagaaaatg ctgagctgta caagaagctc tatgagacag ggcagaaaaa     600
tgaagcgaat cgagattcaa caactccata aactttgcg gttatcgagg aagccaacac      660
tcctgctcgt cttgaactca atcccccaag ccaacaaaat gatgctgagc aaaccacacc     720
tcctaaacta gggtaa                                                     736
```

<210> SEQ ID NO 18
<211> LENGTH: 235
<212> TYPE: PRT
<213> ORGANISM: Oryza sativa
<220> FEATURE:
<223> OTHER INFORMATION: G3479 polypeptide

<400> SEQUENCE: 18

```
Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
            20                  25                  30

Lys Glu Leu Ala Ile Leu Cys Asp Ala Glu Val Gly Leu Val Ile Phe
        35                  40                  45

Ser Ser Thr Gly Arg Leu Tyr Glu Tyr Ala Ser Thr Ser Met Lys Ser
    50                  55                  60

Val Ile Asp Arg Tyr Gly Arg Ala Lys Glu Glu Gln Gln His Val Ala
65                  70                  75                  80

Asn Pro Asn Ser Glu Leu Lys Phe Trp Gln Arg Glu Ala Ala Ser Leu
                85                  90                  95

Arg Gln Gln Leu His Ser Leu Gln Glu Asn His Arg Gln Leu Met Gly
            100                 105                 110

Gln Asp Leu Ser Gly Leu Gly Val Lys Glu Leu Gln Thr Leu Glu Asn
        115                 120                 125

Gln Leu Glu Met Ser Ile Arg Cys Ile Arg Thr Lys Lys Asp Gln Leu
    130                 135                 140

Met Ile Asp Glu Ile His Glu Leu Asn Arg Lys Gly Ser Leu Ile His
145                 150                 155                 160

Gln Glu Asn Met Glu Leu Tyr Arg Lys Val Asn Leu Ile Arg Gln Glu
                165                 170                 175

Asn Ala Glu Leu Tyr Lys Lys Leu Tyr Glu Thr Gly Ala Glu Asn Glu
            180                 185                 190
```

Ala Asn Arg Asp Ser Thr Thr Pro Tyr Asn Phe Ala Val Ile Glu Glu
            195                 200                 205

Ala Asn Thr Pro Ala Arg Leu Glu Leu Asn Pro Pro Ser Gln Gln Asn
        210                 215                 220

Asp Ala Glu Gln Thr Thr Pro Pro Lys Leu Gly
225                 230                 235

<210> SEQ ID NO 19
<211> LENGTH: 723
<212> TYPE: DNA
<213> ORGANISM: Oryza sativa
<220> FEATURE:
<223> OTHER INFORMATION: G3480

<400> SEQUENCE: 19

```
atggggaggg ggaagattgt gatccgccgg atcgacaact cgacgagccg gcaggtgacg      60
ttctcgaagc ggaggaacgg gatcttcaag aaggccaagg agctggccat cctctgcgac     120
gccgaggtcg gcctcatgat cttctccagc accggccgcc tctacgagta ctccagcacc     180
agcatgaagt cagttataga tcggtatggc aagtccaagg atgagcagca agccgtcgca     240
aatcccaact cggagcttaa gttttggcaa agggaggcag caagcttgag acaacaactg     300
cacaacttgc aagaaaatca tcggcagttg atgggcgaag atctatctgg gctgaatgtt     360
aaggaattgc aatctctaga gaatcagctg gaaataagtc tacgtagtgt ccgtacaaag     420
aaggaccacg tcttgattga tgaaattcat gaactgaatc ggaagggaag tctagttcac     480
caagaaaaca tggaattata caagaagatc agtttaattc gtcaagaaaa tgctgagtta     540
tataagaaga tctacgagac tgaaggacca agtgaagtca atcgggattc accaactcct     600
tacaattttg cagtaattga aaaaacaaat gttcctgtgc aacttggact cagcacacta     660
ccacaacata gtgacgccga acaatcaact gctcctaagc tagggttaca gttgaatcca     720
tga                                                                   723
```

<210> SEQ ID NO 20
<211> LENGTH: 240
<212> TYPE: PRT
<213> ORGANISM: Oryza sativa
<220> FEATURE:
<223> OTHER INFORMATION: G3480 polypeptide

<400> SEQUENCE: 20

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
            20                  25                  30

Lys Glu Leu Ala Ile Leu Cys Asp Ala Glu Val Gly Leu Met Ile Phe
        35                  40                  45

Ser Ser Thr Gly Arg Leu Tyr Glu Tyr Ser Ser Thr Ser Met Lys Ser
    50                  55                  60

Val Ile Asp Arg Tyr Gly Lys Ser Lys Asp Glu Gln Gln Ala Val Ala
65                  70                  75                  80

Asn Pro Asn Ser Glu Leu Lys Phe Trp Gln Arg Glu Ala Ala Ser Leu
                85                  90                  95

Arg Gln Gln Leu His Asn Leu Gln Glu Asn His Arg Gln Leu Met Gly
            100                 105                 110

Glu Asp Leu Ser Gly Leu Asn Val Lys Glu Leu Gln Ser Leu Glu Asn
        115                 120                 125

```
Gln Leu Glu Ile Ser Leu Arg Ser Val Arg Thr Lys Lys Asp His Val
    130                 135                 140

Leu Ile Asp Glu Ile His Glu Leu Asn Arg Lys Gly Ser Leu Val His
145                 150                 155                 160

Gln Glu Asn Met Glu Leu Tyr Lys Lys Ile Ser Leu Ile Arg Gln Glu
                165                 170                 175

Asn Ala Glu Leu Tyr Lys Lys Ile Tyr Glu Thr Glu Gly Pro Ser Glu
            180                 185                 190

Val Asn Arg Asp Ser Pro Thr Pro Tyr Asn Phe Ala Val Ile Glu Lys
        195                 200                 205

Thr Asn Val Pro Val Gln Leu Gly Leu Ser Thr Leu Pro Gln His Ser
    210                 215                 220

Asp Ala Glu Gln Ser Thr Ala Pro Lys Leu Gly Leu Gln Leu Asn Pro
225                 230                 235                 240
```

<210> SEQ ID NO 21
<211> LENGTH: 782
<212> TYPE: DNA
<213> ORGANISM: Oryza sativa
<220> FEATURE:
<223> OTHER INFORMATION: G3481

<400> SEQUENCE: 21

```
gtcttagatc tgggagagag cgaggagatg ggggaggggga agatagtgat aaggaggata     60
gacaactcga cgagcaggca ggtgacgttc tcgaagcgtc ggaacgggct tctgaagaag    120
gcgaaggagc tatccatcct ctgcgatgcg gaggtcggcc ttgtcgtctt ctccagcacc    180
ggcaggctct atgagttctc cagcaccaac atgaaaactg tgatagaccg gtataccaac    240
gcaaaggagg agctacttgg cgggaatgca acttcagaaa ttaagatttg cagagggag     300
gcagcaagct tgaggcagca actgcacaac ttgcaagaaa gccacaagca actgatgggt    360
gaggagcttt ctggcctagg tgttagagac ctacaaggtt tagagaatag gcttgaaata    420
agtctacgta atatcagaat gagaaaggac aatctttga aaagtgaaat cgaggagtta     480
catgtgaagg gaagcctaat tcaccaggaa acatcgaac tttctagaag cctaaatgtc     540
atgtcgcaac aaaaattgga actgtataac aagcttcagg cctgtgaaca gagaggtgcc    600
acagatgcaa atgaaagttc cagcactcca tacagctttc gtatcataca aaatgctaat    660
atgcctccta gtcttgaatt gagccaatca cagcaaagag aaggggagtg cagcaaaaca    720
gctgctccag aactgggact tcatctgcct taagactatg ccgtacaagc tggacgataa    780
gt                                                                   782
```

<210> SEQ ID NO 22
<211> LENGTH: 241
<212> TYPE: PRT
<213> ORGANISM: Oryza sativa
<220> FEATURE:
<223> OTHER INFORMATION: G3481 polypeptide

<400> SEQUENCE: 22

```
Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ser Ile Leu Cys Asp Ala Glu Val Gly Leu Val Val Phe
        35                  40                  45
```

```
Ser Ser Thr Gly Arg Leu Tyr Glu Phe Ser Ser Thr Asn Met Lys Thr
    50                  55                  60

Val Ile Asp Arg Tyr Thr Asn Ala Lys Glu Glu Leu Leu Gly Gly Asn
 65                  70                  75                  80

Ala Thr Ser Glu Ile Lys Ile Trp Gln Arg Glu Ala Ala Ser Leu Arg
                 85                  90                  95

Gln Gln Leu His Asn Leu Gln Glu Ser His Lys Gln Leu Met Gly Glu
            100                 105                 110

Glu Leu Ser Gly Leu Gly Val Arg Asp Leu Gln Gly Leu Glu Asn Arg
        115                 120                 125

Leu Glu Ile Ser Leu Arg Asn Ile Arg Met Arg Lys Asp Asn Leu Leu
130                 135                 140

Lys Ser Glu Ile Glu Glu Leu His Val Lys Gly Ser Leu Ile His Gln
145                 150                 155                 160

Glu Asn Ile Glu Leu Ser Arg Ser Leu Asn Val Met Ser Gln Gln Lys
                165                 170                 175

Leu Glu Leu Tyr Asn Lys Leu Gln Ala Cys Glu Gln Arg Gly Ala Thr
            180                 185                 190

Asp Ala Asn Glu Ser Ser Thr Pro Tyr Ser Phe Arg Ile Ile Gln
        195                 200                 205

Asn Ala Asn Met Pro Pro Ser Leu Glu Leu Ser Gln Ser Gln Gln Arg
210                 215                 220

Glu Gly Glu Cys Ser Lys Thr Ala Ala Pro Glu Leu Gly Leu His Leu
225                 230                 235                 240

Pro
```

<210> SEQ ID NO 23
<211> LENGTH: 784
<212> TYPE: DNA
<213> ORGANISM: Zea mays
<220> FEATURE:
<223> OTHER INFORMATION: G3489

<400> SEQUENCE: 23

```
aagaagagag ctagctatag gccggagatc gatggggagg ggaaagatcg tgatccgcag    60
gatcgataac tccacgagcc ggcaggtgac cttctccaag cgccggaacg ggatcttcaa   120
gaaggccaag gagctcgcca tcctctgcga tgcggaggtc ggcctcgtca tcttctccag   180
caccggccgc tcctacgagt actctagcac cagcatgaaa tcagttatag atcggtacgg   240
caaggccaag gaagagcagc aagtcgtcgc aaatcccaac tcggagctta agttttggca   300
aagggaggca gcaagcttga acaacaact gcacaacttg caagaaaatt atcggcagtt   360
gacgggagat gatctttctg ggctgaatgt caaagaactg cagtccctgg agaatcaatt   420
ggaaacaagc ctgcgtggtg tccgcgcaaa gaaggaccat ctcttgatag atgagattca   480
cgatttgaat cgaaaggcaa gtttatttca ccaagaaaat acagacttgt acaataagat   540
caacctgatt cgccaagaaa atgatgagtt acataaaaag atatatgaga ctgaaggacc   600
aagtggagtt aatcgggagt caccgactcc attcaacttt gcagtagtag aaaccagaga   660
tgttcctgtg caacttgaac tcagcacact gccacagcaa aataacattg agccatctac   720
tgctcctaag ctaggattgc aattaattcc atgaagaaga gtaaaactgc cgtcttatga   780
tgct                                                                784
```

<210> SEQ ID NO 24
<211> LENGTH: 240

```
<212> TYPE: PRT
<213> ORGANISM: Zea mays
<220> FEATURE:
<223> OTHER INFORMATION: G3489 polypeptide

<400> SEQUENCE: 24
```

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
            20                  25                  30

Lys Glu Leu Ala Ile Leu Cys Asp Ala Glu Val Gly Leu Val Ile Phe
        35                  40                  45

Ser Ser Thr Gly Arg Leu Tyr Glu Tyr Ser Ser Thr Ser Met Lys Ser
    50                  55                  60

Val Ile Asp Arg Tyr Gly Lys Ala Lys Glu Glu Gln Gln Val Val Ala
65                  70                  75                  80

Asn Pro Asn Ser Glu Leu Lys Phe Trp Gln Arg Glu Ala Ala Ser Leu
                85                  90                  95

Arg Gln Gln Leu His Asn Leu Gln Glu Asn Tyr Arg Gln Leu Thr Gly
            100                 105                 110

Asp Asp Leu Ser Gly Leu Asn Val Lys Glu Leu Gln Ser Leu Glu Asn
        115                 120                 125

Gln Leu Glu Thr Ser Leu Arg Gly Val Arg Ala Lys Lys Asp His Leu
    130                 135                 140

Leu Ile Asp Glu Ile His Asp Leu Asn Arg Lys Ala Ser Leu Phe His
145                 150                 155                 160

Gln Glu Asn Thr Asp Leu Tyr Asn Lys Ile Asn Leu Ile Arg Gln Glu
                165                 170                 175

Asn Asp Glu Leu His Lys Lys Ile Tyr Glu Thr Glu Gly Pro Ser Gly
            180                 185                 190

Val Asn Arg Glu Ser Pro Thr Pro Phe Asn Phe Ala Val Val Glu Thr
        195                 200                 205

Arg Asp Val Pro Val Gln Leu Glu Leu Ser Thr Leu Pro Gln Gln Asn
    210                 215                 220

Asn Ile Glu Pro Ser Thr Ala Pro Lys Leu Gly Leu Gln Leu Ile Pro
225                 230                 235                 240

```
<210> SEQ ID NO 25
<211> LENGTH: 745
<212> TYPE: DNA
<213> ORGANISM: Glycine max
<220> FEATURE:
<223> OTHER INFORMATION: G3484

<400> SEQUENCE: 25
```

| | | | | | |
|---|---|---|---|---|---|
| tttgaccaaa | gatggggaga | ggtaagattg | cgattcgaag | gatcgacaac | tccactagcc | 60 |
| ggcaagtgac | tttctcaaag | agaagaaatg | gattgctgaa | gaaagctaga | gaattatcaa | 120 |
| ttctttgtga | tgctgaagtt | ggattgatgg | tgttctccag | cactgggaag | ctttatgact | 180 |
| atgcaagcac | aagcatgaaa | gcggttattg | aacgctacaa | caagctaaaa | gaggaaaccc | 240 |
| atcacctcat | gaatccggct | tcagaagaga | agttttggca | gacagaagca | gcaagcttga | 300 |
| ggcagcagct | tcagtacttg | caagaatgcc | acaggcaatt | aatggggaa | gaacttacgg | 360 |
| gtttgggtat | taagaactta | caaaatctgg | aaaccaact | ggagatgagt | ttaagggtg | 420 |
| tccgcatgaa | aaaggatcaa | attttaacta | atgagattaa | agaactacgc | caaaagggaa | 480 |
| atatcattca | tcaagaaaat | gttgaactct | atcaaaagat | ggagcagatc | caaaaagaaa | 540 |

```
atgcagagct acaaaagaag gtttatgaag caaggagtac aaatgaagaa aatgtggcat      600
ccaatccttc ttacaacgtc agaaatggat atgattcact tgcatctatc agtctccagc      660
taagtcagcc acagtctcaa tacaaataca gtgaaccatc aaccaaagca atgaaactcg      720
gattgcagct gcattagcaa aaact                                            745
```

```
<210> SEQ ID NO 26
<211> LENGTH: 241
<212> TYPE: PRT
<213> ORGANISM: Glycine max
<220> FEATURE:
<223> OTHER INFORMATION: G3484 polypeptide

<400> SEQUENCE: 26
```

Met Gly Arg Gly Lys Ile Ala Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Arg Glu Leu Ser Ile Leu Cys Asp Ala Glu Val Gly Leu Met Val Phe
        35                  40                  45

Ser Ser Thr Gly Lys Leu Tyr Asp Tyr Ala Ser Thr Ser Met Lys Ala
    50                  55                  60

Val Ile Glu Arg Tyr Asn Lys Leu Lys Glu Glu Thr His His Leu Met
65                  70                  75                  80

Asn Pro Ala Ser Glu Glu Lys Phe Trp Gln Thr Glu Ala Ala Ser Leu
                85                  90                  95

Arg Gln Gln Leu Gln Tyr Leu Gln Glu Cys His Arg Gln Leu Met Gly
            100                 105                 110

Glu Glu Leu Thr Gly Leu Gly Ile Lys Glu Leu Gln Asn Leu Glu Asn
        115                 120                 125

Gln Leu Glu Met Ser Leu Lys Gly Val Arg Met Lys Lys Asp Gln Ile
    130                 135                 140

Leu Thr Asn Glu Ile Lys Glu Leu Arg Gln Lys Gly Asn Ile Ile His
145                 150                 155                 160

Gln Glu Asn Val Glu Leu Tyr Gln Lys Met Glu Gln Ile Gln Lys Glu
                165                 170                 175

Asn Ala Glu Leu Gln Lys Lys Val Tyr Glu Ala Arg Ser Thr Asn Glu
            180                 185                 190

Glu Asn Val Ala Ser Asn Pro Ser Tyr Asn Val Arg Asn Gly Tyr Asp
        195                 200                 205

Ser Leu Ala Ser Ile Ser Leu Gln Leu Ser Gln Pro Gln Ser Gln Tyr
    210                 215                 220

Lys Tyr Ser Glu Pro Ser Thr Lys Ala Met Lys Leu Gly Leu Gln Leu
225                 230                 235                 240

His

```
<210> SEQ ID NO 27
<211> LENGTH: 691
<212> TYPE: DNA
<213> ORGANISM: Zea mays
<220> FEATURE:
<223> OTHER INFORMATION: G3487

<400> SEQUENCE: 27
ggagatgggg agagggaaga tagagatcaa gaggatcgac aacgcgacga gccggcaggt      60
aacgttctcc aagcgccggg gcgggctgtt caagaaggcc aaggagctcg ccatcctttg     120
```

```
cgatgccgag gtcggcctcg tcgtcttctc cagcaccggc cgcctgtatc acttcgctag      180
caccagcatg gaatctgtga ttgaaagata cgaggaaaga gaggggcacc atcagactat      240
gagcgcaagt gctgaggcca agctttggca agggaggca ggaagcttga ggcagcaact       300
gcataacttg caagagcacc atcggaagtt gttgggtcag cagctctctg gcctggacgt      360
gagagatttg cagaatttag agaatcagct ggagacaagc ctaagaaata ttcgtctaaa      420
gatggaccaa cttatttttt atcagattca agaattaaac aggaagggat acctcatgca      480
ccaggaaaac atagaactac acaacaaagt caaccttctt catcaagaga acattaaatt      540
acgtagaaag gcgtatggac aaggagtaaa tgagcatcca acaagtacta cagttagaca      600
cagtattctg aatacagaga atgaagatgt tcggatcaat cttgagctga gtgtgcaaag      660
ggacaaatca gaaacaccaa gtgtagggtg a                                    691
```

<210> SEQ ID NO 28
<211> LENGTH: 228
<212> TYPE: PRT
<213> ORGANISM: Zea mays
<220> FEATURE:
<223> OTHER INFORMATION: G3487 polypeptide

<400> SEQUENCE: 28

```
Met Gly Arg Gly Lys Ile Glu Ile Lys Arg Ile Asp Asn Ala Thr Ser
1               5                   10                  15

Arg Gln Val Thr Phe Ser Lys Arg Arg Gly Gly Leu Phe Lys Lys Ala
                20                  25                  30

Lys Glu Leu Ala Ile Leu Cys Asp Ala Glu Val Gly Leu Val Val Phe
            35                  40                  45

Ser Ser Thr Gly Arg Leu Tyr His Phe Ala Ser Thr Ser Met Glu Ser
        50                  55                  60

Val Ile Glu Arg Tyr Glu Gln Arg Gly His His Gln Thr Met Ser
65                  70                  75                  80

Ala Ser Ala Glu Ala Lys Leu Trp Gln Arg Glu Ala Gly Ser Leu Arg
                85                  90                  95

Gln Gln Leu His Asn Leu Gln Glu His His Arg Lys Leu Leu Gly Gln
            100                 105                 110

Gln Leu Ser Gly Leu Asp Val Arg Asp Leu Gln Asn Leu Glu Asn Gln
        115                 120                 125

Leu Glu Thr Ser Leu Arg Asn Ile Arg Leu Lys Met Asp Gln Leu Ile
    130                 135                 140

Phe Tyr Gln Ile Gln Glu Leu Asn Arg Lys Gly Tyr Leu Met His Gln
145                 150                 155                 160

Glu Asn Ile Glu Leu His Asn Lys Val Asn Leu Leu His Gln Glu Asn
                165                 170                 175

Ile Lys Leu Arg Arg Lys Ala Tyr Gly Gln Gly Val Asn Glu His Pro
            180                 185                 190

Thr Ser Thr Thr Val Arg His Ser Ile Leu Asn Thr Glu Asn Glu Asp
        195                 200                 205

Val Arg Ile Asn Leu Glu Leu Ser Val Gln Arg Asp Lys Ser Glu Thr
    210                 215                 220

Pro Ser Val Gly
225
```

<210> SEQ ID NO 29
<211> LENGTH: 1209

<212> TYPE: DNA
<213> ORGANISM: Zea mays
<220> FEATURE:
<223> OTHER INFORMATION: G3488

<400> SEQUENCE: 29

```
gaattcccgg gtcgacccac gcgtccgccc acgcgtccgg tcgtcctctt ctctcgcctc      60
caataattcg taaccattct ccttccaggc cgggctcctg ctggccggag ttcccatctc     120
cctctttcct tctcggttac tatccgtgag tgtgcctgcc ccgtgtgtg cgcgtgcaag      180
atcgaccggg cgcagcttca cgatggggcg cggcaagata gtgatccgcc ggatcgacaa     240
ctccacgagc cggcaggtga cgttctccaa gcggcgaaac gggatcttca agaaggcaag     300
ggagctcgcc atactctgcg acgcagaggt cgggttggtc atcttctcca gcaccggtcg     360
tctctatgaa tacgccagca caagcataaa gtcagtgatt gatcgatatg gtcgagcaaa     420
ggaggaggag catgtagcag accccaacac agagcttaag ttctggcaaa gggaggcagc     480
aagcttgaga caacaactgc acaacttgca agaaaatcat cggaggcagt tgatgggaca     540
aaatctttct ggactaggtg tcaagggact tcaaaatcta gaaaatcagc tagagatgag     600
catttgttgc atccggacaa aaaggacca actcttggtt gacgaaattc acgaactgaa      660
tcgaaaggga agtctcatcc aacaagacaa catgggatta cacagaaagg tcaacctaat     720
tcgtcaagaa aatgccgaat tatataagaa gctctatgag aaagaagcag aaggtgaagt     780
caaccgagat tcaacaactc cgtacaactt tgtagttgca gagggtgcca acgttcctat     840
ccatcttgag cttaatattc cactgcaaga aaatggtgtt gagcaacctg tggctcctaa     900
attagggttg caattaaatc aatgaagaca tgcaggacat tgcctttgtt ctcattgtcc     960
ttgaagtctg caactcaaag cagcctaaaa tgataggttg taacaggcct aaaaacattg    1020
caagacaaat aaagtatgca tgccagagac agtggcaatg gtagtgcaaa tctatctcaa    1080
ataacttgtg ttatattgaa taatccagca aatggtttgt ttttacacg ttatgcaagt     1140
ttgtttgacc aaaatggtat gtaacatgta caaatttcca agtgaactta ttgaaaaaat    1200
tctataaaa                                                            1209
```

<210> SEQ ID NO 30
<211> LENGTH: 240
<212> TYPE: PRT
<213> ORGANISM: Zea mays
<220> FEATURE:
<223> OTHER INFORMATION: G3488 polypeptide

<400> SEQUENCE: 30

```
Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
            20                  25                  30

Arg Glu Leu Ala Ile Leu Cys Asp Ala Glu Val Gly Leu Val Ile Phe
        35                  40                  45

Ser Ser Thr Gly Arg Leu Tyr Glu Tyr Ala Ser Thr Ser Ile Lys Ser
    50                  55                  60

Val Ile Asp Arg Tyr Gly Arg Ala Lys Glu Glu His Val Ala Asp
65                  70                  75                  80

Pro Asn Thr Glu Leu Lys Phe Trp Gln Arg Glu Ala Ala Ser Leu Arg
            85                  90                  95

Gln Gln Leu His Asn Leu Gln Glu Asn His Arg Arg Gln Leu Met Gly
        100                 105                 110
```

Gln Asn Leu Ser Gly Leu Gly Val Lys Gly Leu Gln Asn Leu Glu Asn
            115                 120                 125

Gln Leu Glu Met Ser Ile Cys Cys Ile Arg Thr Lys Lys Asp Gln Leu
        130                 135                 140

Leu Val Asp Glu Ile His Glu Leu Asn Arg Lys Gly Ser Leu Ile Gln
145                 150                 155                 160

Gln Asp Asn Met Gly Leu His Arg Lys Val Asn Leu Ile Arg Gln Glu
                165                 170                 175

Asn Ala Glu Leu Tyr Lys Lys Leu Tyr Glu Lys Glu Ala Glu Gly Glu
            180                 185                 190

Val Asn Arg Asp Ser Thr Thr Pro Tyr Asn Phe Val Val Ala Glu Gly
        195                 200                 205

Ala Asn Val Pro Ile His Leu Glu Leu Asn Ile Pro Leu Gln Glu Asn
210                 215                 220

Gly Val Glu Gln Pro Val Ala Pro Lys Leu Gly Leu Gln Leu Asn Gln
225                 230                 235                 240

<210> SEQ ID NO 31
<211> LENGTH: 354
<212> TYPE: DNA
<213> ORGANISM: Oryza sativa
<220> FEATURE:
<223> OTHER INFORMATION: G3483

<400> SEQUENCE: 31
atggggagag ggaagataga gataaagagg atcgacaacg cgacgagccg acaggtgaca      60
ttctcgaagc ggcggagcgg gctgttcaag aaggcgaggg agctctccat cctctgcgat     120
gccgaggtcg gcctcctcgt cttctccagc accagccgtc tctatgactt tgccagctcc     180
agcatgaaat ccataattga gagatacaat gagacgaaag aagatcccca tcaaaccatg     240
aacgcaagtt ctgaggcaaa ggaatatatg tcctcagact tgtttaaagt ggttaaagta     300
gggatatctg ttgattctag gtatctgtac tgtataatat ccaccaggc atag           354

<210> SEQ ID NO 32
<211> LENGTH: 117
<212> TYPE: PRT
<213> ORGANISM: Oryza sativa
<220> FEATURE:
<223> OTHER INFORMATION: G3483 polypeptide

<400> SEQUENCE: 32

Met Gly Arg Gly Lys Ile Glu Ile Lys Arg Ile Asp Asn Ala Thr Ser
1               5                   10                  15

Arg Gln Val Thr Phe Ser Lys Arg Arg Ser Gly Leu Phe Lys Lys Ala
            20                  25                  30

Arg Glu Leu Ser Ile Leu Cys Asp Ala Glu Val Gly Leu Leu Val Phe
        35                  40                  45

Ser Ser Thr Ser Arg Leu Tyr Asp Phe Ala Ser Ser Met Lys Ser
    50                  55                  60

Ile Ile Glu Arg Tyr Asn Glu Thr Lys Glu Asp Pro His Gln Thr Met
65                  70                  75                  80

Asn Ala Ser Ser Glu Ala Lys Glu Tyr Met Ser Ser Asp Leu Phe Lys
                85                  90                  95

Val Val Lys Val Gly Ile Ser Val Asp Ser Arg Tyr Leu Tyr Cys Ile
            100                 105                 110

Ile Phe His Gln Ala

```
<210> SEQ ID NO 33
<211> LENGTH: 56
<212> TYPE: PRT
<213> ORGANISM: Arabidopsis thaliana
<220> FEATURE:
<223> OTHER INFORMATION: G1760 conserved MADS DNA binding domain

<400> SEQUENCE: 33

Gly Arg Gly Lys Ile Val Ile Gln Arg Ile Asp Asp Ser Thr Ser Arg
1               5                   10                  15

Gln Val Thr Phe Ser Lys Arg Arg Lys Gly Leu Ile Lys Lys Ala Lys
            20                  25                  30

Glu Leu Ala Ile Leu Cys Asp Ala Glu Val Gly Leu Ile Ile Phe Ser
        35                  40                  45

Ser Thr Gly Lys Leu Tyr Asp Phe
    50                  55

<210> SEQ ID NO 34
<211> LENGTH: 56
<212> TYPE: PRT
<213> ORGANISM: Arabidopsis thaliana
<220> FEATURE:
<223> OTHER INFORMATION: G152 conserved MADS DNA binding domain

<400> SEQUENCE: 34

Gly Arg Gly Lys Ile Val Ile Gln Lys Ile Asp Asp Ser Thr Ser Arg
1               5                   10                  15

Gln Val Thr Phe Ser Lys Arg Arg Lys Gly Leu Ile Lys Lys Ala Lys
            20                  25                  30

Glu Leu Ala Ile Leu Cys Asp Ala Glu Val Cys Leu Ile Ile Phe Ser
        35                  40                  45

Asn Thr Asp Lys Leu Tyr Asp Phe
    50                  55

<210> SEQ ID NO 35
<211> LENGTH: 56
<212> TYPE: PRT
<213> ORGANISM: Antirrhinum majus
<220> FEATURE:
<223> OTHER INFORMATION: G3982 conserved MADS DNA binding domain

<400> SEQUENCE: 35

Gly Arg Gly Lys Ile Val Ile Gln Arg Ile Asp Lys Ser Thr Ser Arg
1               5                   10                  15

Gln Val Thr Phe Ser Lys Arg Arg Ser Gly Leu Leu Lys Lys Ala Lys
            20                  25                  30

Glu Leu Ala Ile Leu Cys Asp Ala Glu Val Gly Val Val Ile Phe Ser
        35                  40                  45

Ser Thr Gly Lys Leu Tyr Glu Phe
    50                  55

<210> SEQ ID NO 36
<211> LENGTH: 56
<212> TYPE: PRT
<213> ORGANISM: Glycine max
<220> FEATURE:
<223> OTHER INFORMATION: G3485 conserved MADS DNA binding domain

<400> SEQUENCE: 36

Gly Arg Gly Lys Ile Val Ile Arg Arg Ile Asp Asn Ser Thr Ser Arg
```

```
            1               5                  10                 15
Gln Val Thr Phe Ser Lys Arg Arg Asn Gly Leu Leu Lys Lys Ala Lys
                 20                  25                 30
Glu Leu Ala Ile Leu Cys Asp Ala Glu Val Gly Val Met Ile Phe Ser
             35                  40                 45
Ser Thr Gly Lys Leu Tyr Asp Phe
         50                  55

<210> SEQ ID NO 37
<211> LENGTH: 56
<212> TYPE: PRT
<213> ORGANISM: Glycine max
<220> FEATURE:
<223> OTHER INFORMATION: G3980 conserved MADS DNA binding domain

<400> SEQUENCE: 37

Gly Arg Gly Lys Ile Val Ile Arg Arg Ile Asp Asn Ser Thr Ser Arg
1               5                   10                  15
Gln Val Thr Phe Ser Lys Arg Arg Asn Gly Leu Leu Lys Lys Ala Lys
                 20                  25                 30
Glu Leu Ala Ile Leu Cys Asp Ala Glu Val Gly Val Met Ile Phe Ser
             35                  40                 45
Ser Thr Gly Lys Leu Tyr Asp Phe
         50                  55

<210> SEQ ID NO 38
<211> LENGTH: 56
<212> TYPE: PRT
<213> ORGANISM: Glycine max
<220> FEATURE:
<223> OTHER INFORMATION: G3981 conserved MADS DNA binding domain

<400> SEQUENCE: 38

Gly Arg Gly Lys Ile Val Ile Arg Arg Ile Asp Asn Ser Thr Ser Arg
1               5                   10                  15
Gln Val Thr Phe Ser Lys Arg Arg Asn Gly Leu Leu Lys Lys Ala Lys
                 20                  25                 30
Glu Leu Ala Ile Leu Cys Asp Ala Glu Val Gly Val Met Ile Phe Ser
             35                  40                 45
Ser Thr Gly Lys Leu Tyr Asp Phe
         50                  55

<210> SEQ ID NO 39
<211> LENGTH: 57
<212> TYPE: PRT
<213> ORGANISM: Arabidopsis thaliana
<220> FEATURE:
<223> OTHER INFORMATION: G153 conserved MADS DNA binding domain

<400> SEQUENCE: 39

Met Gly Arg Gly Lys Ile Val Ile Arg Arg Ile Asp Asn Ser Thr Ser
1               5                   10                  15
Arg Gln Val Thr Phe Ser Lys Arg Arg Ser Gly Leu Leu Lys Lys Ala
                 20                  25                 30
Lys Glu Leu Ser Ile Leu Cys Asp Ala Glu Val Gly Val Ile Ile Phe
             35                  40                 45
Ser Ser Thr Gly Lys Leu Tyr Asp Tyr
         50                  55

<210> SEQ ID NO 40
```

```
<211> LENGTH: 56
<212> TYPE: PRT
<213> ORGANISM: Arabidopsis thaliana
<220> FEATURE:
<223> OTHER INFORMATION: G860 conserved MADS DNA binding domain

<400> SEQUENCE: 40

Gly Arg Gly Lys Ile Ala Ile Lys Arg Ile Asn Asn Ser Thr Ser Arg
1               5                   10                  15

Gln Val Thr Phe Ser Lys Arg Arg Asn Gly Leu Leu Lys Lys Ala Lys
            20                  25                  30

Glu Leu Ala Ile Leu Cys Asp Ala Glu Val Gly Val Ile Ile Phe Ser
        35                  40                  45

Ser Thr Gly Arg Leu Tyr Asp Phe
    50                  55

<210> SEQ ID NO 41
<211> LENGTH: 56
<212> TYPE: PRT
<213> ORGANISM: Oryza sativa
<220> FEATURE:
<223> OTHER INFORMATION: G3479 conserved MADS DNA binding domain

<400> SEQUENCE: 41

Gly Arg Gly Lys Ile Val Ile Arg Arg Ile Asp Asn Ser Thr Ser Arg
1               5                   10                  15

Gln Val Thr Phe Ser Lys Arg Arg Asn Gly Ile Phe Lys Lys Ala Lys
            20                  25                  30

Glu Leu Ala Ile Leu Cys Asp Ala Glu Val Gly Leu Val Ile Phe Ser
        35                  40                  45

Ser Thr Gly Arg Leu Tyr Glu Tyr
    50                  55

<210> SEQ ID NO 42
<211> LENGTH: 56
<212> TYPE: PRT
<213> ORGANISM: Oryza sativa
<220> FEATURE:
<223> OTHER INFORMATION: G3480 conserved MADS DNA binding domain

<400> SEQUENCE: 42

Gly Arg Gly Lys Ile Val Ile Arg Arg Ile Asp Asn Ser Thr Ser Arg
1               5                   10                  15

Gln Val Thr Phe Ser Lys Arg Arg Asn Gly Ile Phe Lys Lys Ala Lys
            20                  25                  30

Glu Leu Ala Ile Leu Cys Asp Ala Glu Val Gly Leu Met Ile Phe Ser
        35                  40                  45

Ser Thr Gly Arg Leu Tyr Glu Tyr
    50                  55

<210> SEQ ID NO 43
<211> LENGTH: 56
<212> TYPE: PRT
<213> ORGANISM: Oryza sativa
<220> FEATURE:
<223> OTHER INFORMATION: G3481 conserved MADS DNA binding domain

<400> SEQUENCE: 43

Gly Arg Gly Lys Ile Val Ile Arg Arg Ile Asp Asn Ser Thr Ser Arg
1               5                   10                  15

Gln Val Thr Phe Ser Lys Arg Arg Asn Gly Leu Leu Lys Lys Ala Lys
            20                  25                  30
```

```
Glu Leu Ser Ile Leu Cys Asp Ala Glu Val Gly Leu Val Val Phe Ser
        35                  40                  45

Ser Thr Gly Arg Leu Tyr Glu Phe
    50                  55

<210> SEQ ID NO 44
<211> LENGTH: 56
<212> TYPE: PRT
<213> ORGANISM: Zea mays
<220> FEATURE:
<223> OTHER INFORMATION: G3489 conserved MADS DNA binding domain

<400> SEQUENCE: 44

Gly Arg Gly Lys Ile Val Ile Arg Arg Ile Asp Asn Ser Thr Ser Arg
1               5                   10                  15

Gln Val Thr Phe Ser Lys Arg Arg Asn Gly Ile Phe Lys Lys Ala Lys
            20                  25                  30

Glu Leu Ala Ile Leu Cys Asp Ala Glu Val Gly Leu Val Ile Phe Ser
        35                  40                  45

Ser Thr Gly Arg Leu Tyr Glu Tyr
    50                  55

<210> SEQ ID NO 45
<211> LENGTH: 56
<212> TYPE: PRT
<213> ORGANISM: Glycine max
<220> FEATURE:
<223> OTHER INFORMATION: G3484 conserved MADS DNA binding domain

<400> SEQUENCE: 45

Gly Arg Gly Lys Ile Ala Ile Arg Arg Ile Asp Asn Ser Thr Ser Arg
1               5                   10                  15

Gln Val Thr Phe Ser Lys Arg Arg Asn Gly Leu Leu Lys Lys Ala Arg
            20                  25                  30

Glu Leu Ser Ile Leu Cys Asp Ala Glu Val Gly Leu Met Val Phe Ser
        35                  40                  45

Ser Thr Gly Lys Leu Tyr Asp Tyr
    50                  55

<210> SEQ ID NO 46
<211> LENGTH: 56
<212> TYPE: PRT
<213> ORGANISM: Zea mays
<220> FEATURE:
<223> OTHER INFORMATION: G3487 conserved MADS DNA binding domain

<400> SEQUENCE: 46

Gly Arg Gly Lys Ile Glu Ile Lys Arg Ile Asp Asn Ala Thr Ser Arg
1               5                   10                  15

Gln Val Thr Phe Ser Lys Arg Arg Gly Gly Leu Phe Lys Lys Ala Lys
            20                  25                  30

Glu Leu Ala Ile Leu Cys Asp Ala Glu Val Gly Leu Val Val Phe Ser
        35                  40                  45

Ser Thr Gly Arg Leu Tyr His Phe
    50                  55

<210> SEQ ID NO 47
<211> LENGTH: 56
<212> TYPE: PRT
<213> ORGANISM: Zea mays
<220> FEATURE:
```

<223> OTHER INFORMATION: G3488 conserved MADS DNA binding domain

<400> SEQUENCE: 47

Gly Arg Gly Lys Ile Val Ile Arg Arg Ile Asp Asn Ser Thr Ser Arg
1               5                   10                  15

Gln Val Thr Phe Ser Lys Arg Arg Asn Gly Ile Phe Lys Lys Ala Arg
            20                  25                  30

Glu Leu Ala Ile Leu Cys Asp Ala Glu Val Gly Leu Val Ile Phe Ser
        35                  40                  45

Ser Thr Gly Arg Leu Tyr Glu Tyr
    50                  55

<210> SEQ ID NO 48
<211> LENGTH: 56
<212> TYPE: PRT
<213> ORGANISM: Oryza sativa
<220> FEATURE:
<223> OTHER INFORMATION: G3483 conserved MADS DNA binding domain

<400> SEQUENCE: 48

Gly Arg Gly Lys Ile Glu Ile Lys Arg Ile Asp Asn Ala Thr Ser Arg
1               5                   10                  15

Gln Val Thr Phe Ser Lys Arg Arg Ser Gly Leu Phe Lys Lys Ala Arg
            20                  25                  30

Glu Leu Ser Ile Leu Cys Asp Ala Glu Val Gly Leu Leu Val Phe Ser
        35                  40                  45

Ser Thr Ser Arg Leu Tyr Asp Phe
    50                  55

<210> SEQ ID NO 49
<211> LENGTH: 1586
<212> TYPE: DNA
<213> ORGANISM: artificial sequence
<220> FEATURE:
<223> OTHER INFORMATION: expression construct P1461 (35S::G1760)

<400> SEQUENCE: 49
gcggattcca ttgcccagct atctgtcact ttattgtgaa gatagtgaaa agaaggtgg      60 ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccacccca cgaggagcat    420 cgtggaaaaa gaagacgttc caaccacgtc ttcaaagcaa gtggattgat gtgatatctc    480
cactgacgta agggatgacg cacaatccca ctatccttcg caagacccct cctctatata    540
aggaagttca tttcatttgg agaggacacg ctgaccctaa aaagagaag aaccagagga    600 gattcaatta gaggataaaa ttgatgggaa gagggaagat tgtgatccaa aggatcgatg    660
attcaacgag tagacaagtc actttctcca acgaagaaa gggccttatc aagaaagcca    720
aagagctagc tattctctgt gatgccgagg tcggtctcat catcttctct agcaccggaa    780
agctctatga ctttgcaagc tccagcatga agtcggttat tgatagatac aacaagagca    840
agatcgagca caacaacta ttgaaccccg catcagaagt caagttttgg cagagagaag    900
ctgctgttct aagacaagaa ctgcatgctt tgcaagaaaa tcatcggcaa atgatgggag    960

```
aacagctaaa tggtttaagt gttaacgagc taaacagtct tgagaatcaa attgagataa    1020
gtttgcgtgg aattcgtatg agaaaggaac aactgttgac tcaagaaatc caagaactaa    1080
gccaaaagag gaatcttatt catcaggaaa acctcgattt atctaggaaa gtacaacgga    1140
ttcatcaaga aaatgtggag ctctacaaga aggcttatat ggcaaacaca acgggttta     1200 cacaccgtga agtagctgtt gcggatgatg aatcacacac tcagattcgg ctgcaactaa    1260
gccagcctga acattccgat tatgacactc caccaagagc aaacgaataa cagagagatt    1320
gaagttggaa gataccatga tgttgaagaa cactccaaag gccttggttt gaataaggtt    1380
cttgaactgg aaacctctat acaccaagcc acgtacgata agcagcatgg ttcttctaac    1440
atagtcatat tttcaatcct aaatataatt aaagcatata taattaaaat ccggtgttgt    1500
tatactcatc ttgagtatta atattgtact tgtttataac catagattcg tcaattaata    1560
gagaaaaatc atatgaatta ttatcc                                         1586

<210> SEQ ID NO 50
<211> LENGTH: 1533
<212> TYPE: DNA
<213> ORGANISM: artificial sequence
<220> FEATURE:
<223> OTHER INFORMATION: expression construct P896 (35S::G152)

<400> SEQUENCE: 50
gcggattcca ttgcccagct atctgtcact ttattgtgaa gatagtgaaa aagaaggtgg      60
ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccaccca cgaggagcat    420
cgtggaaaaa gaagacgttc caaccacgtc ttcaaagcaa gtggattgat gtgatatctc    480
cactgacgta agggatgacg cacaatccca ctatccttcg caagacccttcctctatata    540 aggaagttca tttcatttgg agaggacacg ctgacctaga acgcaccaag atctaaagga    600
agatcaaaat agggtttaaa ttaatgggga gagggaagat tgtgatccag aagatcgatg    660
attccacgag tagacaagtc actttctcca aaagaagaaa gggtctcatc aagaaagcta    720
aagaacttgc tattctctgc gacgccgagg tctgtctcat cattttctcc aacactgaca    780
agctctatga ctttgccagc tccagtgtga atctactat tgaacgattc aatacggcta    840
agatggagga gcaagaacta atgaaccctg catcagaagt taagttttgg cagagagagg    900
ctgaaactct aaggcaagaa ttgcactcat tgcaagaaaa ttatcggcaa ctaacgggag    960
tggaattaaa tggtttgagc gttaaggagt tacaaaacat agagagtcaa cttgaaatga    1020
gtttacgtgg aattcgtatg aaaagggaac aaattttgac caatgaaatt aaagagctaa    1080
ccagaaagag gaatcttgtt catcatgaaa acctcgaatt gtcgagaaaa gtacaaagga    1140
ttcatcaaga aaatgtcgaa ctatacaaga aggcttatgg aacgtcgaac acaaatggat    1200
tgggacatca tgagctagta gatgcagttt atgaatccca tgcacaggtt aggctgcagc    1260
taagccagcc tgagcagtcc cattataaga catcttcaaa cagctaagat catataagag    1320
atatataaca aattgttcgt tcttgattat ctcaaaaccc tttcaaatat atacgtgc      1380
```

-continued

| | |
|---|---|
| atattatata tgaagactcg tttgactatg tcaatatata tgttttcatg caggagtaag | 1440 |
| tgtgagtgta atcatgtcgg agagcaaacc aaaggtttga tttgtacgat atatacttat | 1500 |
| atatggtctc aagtgaaagc aatggaacag ctt | 1533 |

<210> SEQ ID NO 51
<211> LENGTH: 1230
<212> TYPE: DNA
<213> ORGANISM: artificial sequence
<220> FEATURE:
<223> OTHER INFORMATION: expression construct P26747 (35S::G3981)

<400> SEQUENCE: 51

| | |
|---|---|
| gcggattcca ttgcccagct atctgtcact ttattgtgaa gatagtgaaa agaaggtgg | 60 |
| ctcctacaaa tgccatcatt gcgataaagg aaaggccatc gttgaagatg cctctgccga | 120 |
| cagtggtccc aaagatggac ccccacccac gaggagcatc gtggaaaaag aagacgttcc | 180 |
| aaccacgtct tcaaagcaag tggattgatg tgatggtccg attgagactt ttcaacaaag | 240 |
| ggtaatatcc ggaaacctcc tcggattcca ttgcccagct atctgtcact ttattgtgaa | 300 |
| gatagtggaa aaggaaggtg gctcctacaa atgccatcat tgcgataaag gaaaggccat | 360 |
| cgttgaagat gcctctgccg acagtggtcc caaagatgga ccccacccca cgaggagcat | 420 |
| cgtggaaaaa gaagacgttc caaccacgtc ttcaaagcaa gtggattgat gtgatatctc | 480 |
| cactgacgta agggatgacg cacaatccca ctatccttcg caagacccct cctctatata | 540 |
| aggaagttca tttcatttgg agaggacacg ctgagcgaag gagcttgcga tcttgtgcga | 600 |
| tgctgaagtc ggagttatga tcttctccag caccggaaaa ctctacgatt ttgccagctc | 660 |
| cggcatgaaa tcagtaattg accgatacaa caatcaaaa gaagaaccttt gtcaacttgg | 720 |
| gagttcagct tcagaaatta gttttggca aagggaggca gcaatgttaa ggcaacaatt | 780 |
| acacaatttg caagaaagtc accggaaaat gatggggaa gaactgtcag gcttgacagt | 840 |
| caaagaatta caaatttgg agaaccaatt agaaattagc cttcgaggtg tccgaatgaa | 900 |
| aaggatcaa cttttaatgg atgaaataca agagttaaat cggaagggaa acctcataca | 960 |
| ccaagaaaat gtggaactgt atcagaaggt aaacctaatc tgtcaagaaa acatggaatt | 1020 |
| gaaaagaag gtctatggaa caaaagatga taacaaaaca aacagagatt ctgttctcac | 1080 |
| aaatggtcta ggcataggag aggatttgca agtgcctgtg aatctccagc taagccagcc | 1140 |
| acagcaacaa cactacaagg aaccttcagg aactacaaaa ttgggattgc aattgcattg | 1200 |
| atccatttac aggacgtgtg tttctcaatt | 1230 |

<210> SEQ ID NO 52
<211> LENGTH: 1352
<212> TYPE: DNA
<213> ORGANISM: artificial sequence
<220> FEATURE:
<223> OTHER INFORMATION: expression construct P15260 (35S::G153)

<400> SEQUENCE: 52

| | |
|---|---|
| gcggattcca ttgcccagct atctgtcact ttattgtgaa gatagtgaaa agaaggtgg | 60 |
| ctcctacaaa tgccatcatt gcgataaagg aaaggccatc gttgaagatg cctctgccga | 120 |
| cagtggtccc aaagatggac ccccacccac gaggagcatc gtggaaaaag aagacgttcc | 180 |
| aaccacgtct tcaaagcaag tggattgatg tgatggtccg attgagactt ttcaacaaag | 240 |
| ggtaatatcc ggaaacctcc tcggattcca ttgcccagct atctgtcact ttattgtgaa | 300 |
| gatagtggaa aaggaaggtg gctcctacaa atgccatcat tgcgataaag gaaaggccat | 360 |

```
cgttgaagat gcctctgccg acagtggtcc caaagatgga ccccacccca cgaggagcat      420
cgtggaaaaa gaagacgttc caaccacgtc ttcaaagcaa gtggattgat gtgatatctc      480
cactgacgta agggatgacg cacaatccca ctatccttcg caagacccct cctctatata      540
aggaagttca tttcatttgg agaggacacg ctgatcgctc aattggtttt ggtgttagtc      600
ttttggggag agagatgggg agagggaaga tagttatacg aaggatcgat aactctacaa      660
gtagacaagt gactttctcc aagagaagga gtggtttgct taagaaagct aaagagttat      720
cgatcctttg tgatgcagaa gttggtgtta tcatattctc tagcaccgga aagctctacg      780
actacgcaag caattcaagt atgaaaacaa tcattgagcg gtacaacaga gtaaaagagg      840
agcagcatca acttctgaat catgcctcag agataaagtt ttggcaaaga gaggttgcaa      900
gtttgcagca gcagctccaa tatctacaag aatgccacag gaaactagtg ggagaggaac      960
tttctggaat gaatgctaac gacctacaaa accttgaaga ccagctagta acaagtctaa     1020
aaggtgttcg tctcaaaaag gatcaactta tgacaaatga aatcagagaa cttaatcgta     1080
agggacaaat catccaaaaa gagaatcacg agctacaaaa tattgtagat ataatgcgta     1140
aggaaaatat taaattgcaa aagaaggttc atggaagaac aaatgcgatt gaaggcaatt     1200
caagtgtaga tccaataagc aatggaacca caacatatgc accaccgcaa cttcaactca     1260
tacaactaca accagctcct agagaaaaat caatcagact agggctacaa ctttcctagc     1320
aaaacatgtg ggacatcgaa caatatgcgg cc                                   1352
```

<210> SEQ ID NO 53
<211> LENGTH: 1654
<212> TYPE: DNA
<213> ORGANISM: artificial sequence
<220> FEATURE:
<223> OTHER INFORMATION: expression construct P1269 (35S::G860)

<400> SEQUENCE: 53

```
gcggattcca ttgcccagct atctgtcact ttattgtgaa gatagtgaaa agaaggtgg       60 ctcctacaaa tgccatcatt gcgataaagg aaaggccatc gttgaagatg cctctgccga     120
cagtggtccc aaagatggac ccccaccac gaggagcatc gtggaaaaag aagacgttcc     180
aaccacgtct tcaaagcaag tggattgatg tgatggtccg attgagactt ttcaacaaag     240
ggtaatatcc ggaaacctcc tcggattcca ttgcccagct atctgtcact ttattgtgaa     300
gatagtggaa aagaaggtg gctcctacaa atgccatcat tgcgataaag gaaaggccat     360
cgttgaagat gcctctgccg acagtggtcc caaagatgga ccccacccca cgaggagcat     420
cgtggaaaaa gaagacgttc caaccacgtc ttcaaagcaa gtggattgat gtgatatctc     480
cactgacgta agggatgacg cacaatccca ctatccttcg caagacccct cctctatata     540
aggaagttca tttcatttgg agaggacacg ctgaacaaaa ccacatctct gaactgaacc     600
aatttctctt ctcccccttc cggttatcgg attaccagat ctcgtttccc gcgatctagt     660
ttattctttg aaaaagtgat agaagcagaa atgggaaggg gcaagatcgc gattaagagg     720
atcaataact ctacgagccg tcaggttacg ttctcgaagc gaaggaatgg attgttgaag     780
aaagctaagg agcttgcgat tctctgcgat gctgaggttg tgtcatcat cttctccagc     840 accggtaggc tctacgattt ctccagctcc agcatgaaat cggtcataga gagatacagc     900
gatgccaaag gagaaaccag ttcagaaaat gatcccgctt cagaaattca gttctggcaa     960
aaggaggctg cgattctaaa gcgtcagcta cataacttgc aagaaaacca ccggcaaatg    1020
```

| | |
|---|---:|
| atgggggagg agctctctgg actaagtgta gaagctttac agaatttgga aaatcagctt | 1080 |
| gaattgagcc ttcgtggcgt tcgaatgaaa aggatcaaa tgttaatcga agaaatacaa | 1140 |
| gtacttaacc gagagggaa tctcgttcac caagagaatt tagacctcca caagaaagta | 1200 |
| aacctaatgc accaacagaa catggaacta catgaaaagg tttcagaggt cgagggtgtg | 1260 |
| aaaatcgcaa acaagaattc tcttctcaca aatggtctag acatgagaga tacctcgaac | 1320 |
| gaacatgtcc atcttcagct cagccaaccg cagcatgatc atgagacgca ttcaaaagct | 1380 |
| atccaactca actattttc cttcattgca taatataatt cggtgtgcca acacacttat | 1440 |
| gttgacctcg tcggaatcat atcacaattc actgtgtcag cttgcctctg cataagcgaa | 1500 |
| aataaaaaca taaacatgat cagtttgcat tccatatcta tcaaacacca gctttgtaac | 1560 |
| ttttaaaact ttttctccgt gcaaagacct tggtttggc gcttaagcat gtagtttgat | 1620 |
| gatcaaagga aatgggtgtt ttagcataaa gttg | 1654 |

<210> SEQ ID NO 54
<211> LENGTH: 1310
<212> TYPE: DNA
<213> ORGANISM: artificial sequence
<220> FEATURE:
<223> OTHER INFORMATION: expression construct P26738 (35S::G3479)

<400> SEQUENCE: 54

| | |
|---|---:|
| gcggattcca ttgcccagct atctgtcact ttattgtgaa gatagtgaaa aagaaggtgg | 60 |
| ctcctacaaa tgccatcatt gcgataaagg aaaggccatc gttgaagatg cctctgccga | 120 |
| cagtggtccc aaagatggac ccccacccac gaggagcatc gtggaaaaag aagacgttcc | 180 |
| aaccacgtct tcaaagcaag tggattgatg tgatggtccg attgagactt tcaacaaag | 240 |
| ggtaatatcc ggaaacctcc tcggattcca ttgcccagct atctgtcact ttattgtgaa | 300 |
| gatagtggaa aaggaaggtg gctcctacaa atgccatcat tgcgataaag gaaaggccat | 360 |
| cgttgaagat gcctctgccg acagtggtcc caaagatgga cccccaccca cgaggagcat | 420 |
| cgtggaaaaa gaagacgttc caaccacgtc ttcaaagcaa gtggattgat gtgatatctc | 480 |
| cactgacgta agggatgacg cacaatccca ctatccttcg caagacccct cctctatata | 540 |
| aggaagttca tttcatttgg agaggacacg ctgaaatcca gctgagatcg atcgatcgat | 600 |
| cgatggggag gggcaagata gtgatccggc ggatcgacaa ctcgacgagc cggcaggtga | 660 |
| cgttctcgaa gcggcgcaac gggatcttca agaaggccaa ggagctggcc atcctgtgcg | 720 |
| acgccgaggt cggcctcgtc atcttctcca gcaccggccg cctctacgag tatgccagca | 780 |
| ccagcatgaa gtcagtgatt gatcgatatg ggcgagctaa ggaggagcag cagcacgtcg | 840 |
| caaaccccaa ctcggagctg aagttctggc aaagggaggc agcaagcttg agacaacaac | 900 |
| tgcacagctt gcaagaaaat catcggcagt tgatgggca agatctttct ggattgggtg | 960 |
| tcaaggaact gcaaactcta gaaaatcagc tagaaatgag catacgctgc atccggacaa | 1020 |
| aaaaggacca gctcatgatt gatgaaatcc acgaactgaa tcgaaaggga agtctcatcc | 1080 |
| accaagaaaa catggaactg tacagaaagg tcaacctgat tcgccaagaa aatgctgagc | 1140 |
| tgtacaagaa gctctatgag acagggggcag aaaatgaagc gaatcgagat tcaacaactc | 1200 |
| catacaactt tgcggttatc gaggaagcca acactcctgc tcgtcttgaa ctcaatcccc | 1260 |
| caagccaaca aaatgatgct gagcaaacca cacctcctaa actagggtaa | 1310 |

<210> SEQ ID NO 55
<211> LENGTH: 953

```
<212> TYPE: DNA
<213> ORGANISM: artificial sequence
<220> FEATURE:
<223> OTHER INFORMATION: expression construct P21388 (35S::G3480)

<400> SEQUENCE: 55
gcggattcca ttgcccagct atctgtcact ttattgtgaa gatagtgaaa aagaaggtgg      60
ctcctacaaa tgccatcatt gcgataaagg aaaggccatc gttgaagatg cctctgccga     120
cagtggtccc aaagatggac ccccacccac gaggagcatc gtggaaaaag aagacgttcc     180
aaccacgtct tcaaagcaag tggattgatg tgatggtccg attgagactt tcaacaaag      240
ggtaatatcc ggaaacctcc tcggattcca ttgcccagct atctgtcact ttattgtgaa     300
gatagtggaa aaggaaggtg gctcctacaa atgccatcat tgcgataaag gaaaggccat     360
cgttgaagat gcctctgccg acagtggtcc caaagatgga cccccaccca cgaggagcat     420
cgtggaaaaa gaagacgttc caaccacgtc ttcaaagcaa gtggattgat gtgatatctc     480
cactgacgta agggatgacg cacaatccca ctatccttcg caagacccct cctctatata     540
aggaagttca tttcatttgg agaggacacg ctgaatgggg aggggaaga ttgtgatccg      600
ccggatcgac aactcgacga gccggcaggt gacgttctcg aagcgagga acggatctt       660
caagaaggcc aaggagctgg ccatcctctg cgacgccgag gtcggcctca tgatcttctc     720
cagcaccggc cgcctctacg agtactccag caccagcatg aagtcagtta tagatcggta     780
tggcaagtcc aaggatgagc agcaagccgt cgcaaatccc aactcggagc ttaagttttg     840
gcaaagggag gcagcaagct tgagacaaca actgcacaac ttgcaagaaa atcatcggca     900
gttgatgggc gaagatctat ctgggctgaa tgttaaggaa ttgcaatctc tag            953

<210> SEQ ID NO 56
<211> LENGTH: 1356
<212> TYPE: DNA
<213> ORGANISM: artificial sequence
<220> FEATURE:
<223> OTHER INFORMATION: expression construct P26740 (35S::G3481)

<400> SEQUENCE: 56
gcggattcca ttgcccagct atctgtcact ttattgtgaa gatagtgaaa aagaaggtgg      60
ctcctacaaa tgccatcatt gcgataaagg aaaggccatc gttgaagatg cctctgccga     120
cagtggtccc aaagatggac ccccacccac gaggagcatc gtggaaaaag aagacgttcc     180
aaccacgtct tcaaagcaag tggattgatg tgatggtccg attgagactt tcaacaaag      240
ggtaatatcc ggaaacctcc tcggattcca ttgcccagct atctgtcact ttattgtgaa     300
gatagtggaa aaggaaggtg gctcctacaa atgccatcat tgcgataaag gaaaggccat     360
cgttgaagat gcctctgccg acagtggtcc caaagatgga cccccaccca cgaggagcat     420
cgtggaaaaa gaagacgttc caaccacgtc ttcaaagcaa gtggattgat gtgatatctc     480
cactgacgta agggatgacg cacaatccca ctatccttcg caagacccct cctctatata     540
aggaagttca tttcatttgg agaggacacg ctgagtctta gatctgggag agagcgagga     600
gatggggagg gggaagatag tgataaggag gatagacaac tcgacgagca ggcaggtgac     660
gttctcgaag cgtcggaacg ggcttctgaa gaaggcgaag gagctatcca tcctctgcga     720
tgcggaggtc ggccttgtcg tcttctccag caccggcagg ctctatgagt tctccagcac     780
caacatgaaa actgtgatag accggtatac caacgcaaag gaggagctac ttggcgggaa     840
tgcaacttca gaaattaaga tttggcagag ggaggcagca agcttgaggc agcaactgca     900
```

| | |
|---|---|
| caacttgcaa gaaagccaca agcaactgat gggtgaggag ctttctggcc taggtgttag | 960 |
| agacctacaa ggtttagaga ataggcttga aataagtcta cgtaatatca gaatgagaaa | 1020 |
| ggacaatctt ttgaaaagtg aaatcgagga gttacatgtg aagggaagcc taattcacca | 1080 |
| ggaaaacatc gaactttcta gaagcctaaa tgtcatgtcg caacaaaaat tggaactgta | 1140 |
| taacaagctt caggcctgtg aacagagagg tgccacagat gcaaatgaaa gttccagcac | 1200 |
| tccatacagc tttcgtatca tacaaaatgc taatatgcct cctagtcttg aattgagcca | 1260 |
| atcacagcaa agagaagggg agtgcagcaa aacagctgct ccagaactgg gacttcatct | 1320 |
| gccttaagac tatgccgtac aagctggacg ataagt | 1356 |

<210> SEQ ID NO 57
<211> LENGTH: 1358
<212> TYPE: DNA
<213> ORGANISM: artificial sequence
<220> FEATURE:
<223> OTHER INFORMATION: expression construct P26743 (35S::G3489)

<400> SEQUENCE: 57

| | |
|---|---|
| gcggattcca ttgcccagct atctgtcact ttattgtgaa gatagtgaaa agaaggtgg | 60 |
| ctcctacaaa tgccatcatt gcgataaagg aaaggccatc gttgaagatg cctctgccga | 120 |
| cagtggtccc aaagatggac ccccacccac gaggagcatc gtggaaaaag aagacgttcc | 180 |
| aaccacgtct tcaaagcaag tggattgatg tgatggtccg attgagactt ttcaacaaag | 240 |
| ggtaatatcc ggaaacctcc tcggattcca ttgcccagct atctgtcact ttattgtgaa | 300 |
| gatagtggaa aagaaggtg gctcctacaa atgccatcat tgcgataaag gaaaggccat | 360 |
| cgttgaagat gcctctgccg acagtggtcc caaagatgga cccccaccca cgaggagcat | 420 |
| cgtggaaaaa gaagacgttc caaccacgtc ttcaaagcaa gtggattgat gtgatatctc | 480 |
| cactgacgta agggatgacg cacaatccca ctatccttcg caagacccct cctctatata | 540 |
| aggaagttca tttcatttgg agaggacacg ctgaaagaag agagctagct ataggccgga | 600 |
| gatcgatggg gaggggaaag atcgtgatcc gcaggatcga taactccacg agccggcagg | 660 |
| tgaccttctc caagcgccgg aacgggatct tcaagaaggc caaggagctc gccatcctct | 720 |
| gcgatgcgga ggtcggcctc gtcatcttct ccagcaccgg ccgcctctac gagtactcta | 780 |
| gcaccagcat gaaatcagtt atagatcggt acggcaaggc caaggaagag cagcaagtcg | 840 |
| tcgcaaatcc caactcggag cttaagtttt ggcaaaggga ggcagcaagc ttgagacaac | 900 |
| aactgcacaa cttgcaagaa aattatcggc agttgacggg agatgatctt tctgggctga | 960 |
| atgtcaaaga actgcagtcc ctggagaatc aattggaaac aagcctgcgt ggtgtccgcg | 1020 |
| caaagaagga ccatctcttg atagatgaga ttcacgattt gaatcgaaag gcaagtttat | 1080 |
| ttcaccaaga aaatacagac ttgtacaata agatcaacct gattcgccaa gaaaatgatg | 1140 |
| agttacataa aaagatatat gagactgaag gaccaagtgg agttaatcgg gagtcaccga | 1200 |
| ctccattcaa ctttgcagta gtagaaacca gagatgttcc tgtgcaactt gaactcagca | 1260 |
| cactgccaca gcaaaataac attgagccat ctactgctcc taagctagga ttgcaattaa | 1320 |
| ttccatgaag aagagtaaaa ctgccgtctt atgatgct | 1358 |

<210> SEQ ID NO 58
<211> LENGTH: 1319
<212> TYPE: DNA
<213> ORGANISM: artificial sequence
<220> FEATURE:
<223> OTHER INFORMATION: expression construct P26744 (35S::G3484)

<400> SEQUENCE: 58

```
gcggattcca ttgcccagct atctgtcact ttattgtgaa gatagtgaaa aagaaggtgg     60
ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccaccca cgaggagcat    420
cgtggaaaaa gaagacgttc caaccacgtc ttcaaagcaa gtggattgat gtgatatctc    480
cactgacgta agggatgacg cacaatccca ctatccttcg caagaccctt cctctatata    540
aggaagttca tttcatttgg agaggacacg ctgatttgac caaagatggg gagaggtaag    600
attgcgattc gaaggatcga caactccact agccggcaag tgactttctc aaagagaaga    660
aatggattgc tgaagaaagc tagagaatta tcaattcttt gtgatgctga agttggattg    720
atggtgttct ccagcactgg gaagctttat gactatgcaa gcacaagcat gaaagcggtt    780
attgaacgct acaacaagct aaaagaggaa acccatcacc tcatgaatcc ggcttcagaa    840
gagaagtttt ggcagacaga agcagcaagc ttgaggcagc agcttcagta cttgcaagaa    900
tgccacaggc aattaatggg ggaagaactt acgggtttgg gtattaaaga actacaaaat    960
ctggaaaacc aactggagat gagtttaaag ggtgtccgca tgaaaaagga tcaaatttta   1020
actaatgaga ttaaagaact acgccaaaag ggaaatatca ttcatcaaga aaatgttgaa   1080
ctctatcaaa agatggagca gatccaaaaa gaaaatgcag agctacaaaa gaaggtttat   1140
gaagcaagga gtacaaatga agaaaatgtg gcatccaatc cttcttacaa cgtcagaaat   1200
ggatatgatt cacttgcatc tatcagtctc cagctaagtc agccacagtc tcaatacaaa   1260
tacagtgaac catcaaccaa agcaatgaaa ctcggattgc agctgcatta gcaaaaact    1319
```

<210> SEQ ID NO 59
<211> LENGTH: 1265
<212> TYPE: DNA
<213> ORGANISM: artificial sequence
<220> FEATURE:
<223> OTHER INFORMATION: expression construct P26820 (35S::G3487)

<400> SEQUENCE: 59

```
gcggattcca ttgcccagct atctgtcact ttattgtgaa gatagtgaaa aagaaggtgg     60
ctcctacaaa tgccatcatt gcgataaagg aaaggccatc gttgaagatg cctctgccga    120
cagtggtccc aaagatggac ccccacccac gaggagcatc gtggaaaaag aagacgttcc    180
aaccacgtct tcaaagcaag tggattgatg tgatggtccg attgagactt ttcaacaaag    240
ggtaatatcc ggaaacctcc tcggattcca ttgcccagct atctgtcact ttattgtgaa    300
gatagtggaa aaggaaggtg gctcctacaa atgccatcat tgcgataaag gaaaggccat    360
cgttgaagat gcctctgccg acagtggtcc caaagatgga cccccaccca cgaggagcat    420
cgtggaaaaa gaagacgttc caaccacgtc ttcaaagcaa gtggattgat gtgatatctc    480
cactgacgta agggatgacg cacaatccca ctatccttcg caagaccctt cctctatata    540
aggaagttca tttcatttgg agaggacacg ctgaggagat ggggagaggg aagatagaga    600
tcaagaggat cgacaacgcg acgagccggc aggtaacgtt ctccaagcgc cggggcgggc    660
```

| | |
|---|---:|
| tgttcaagaa ggccaaggag ctcgccatcc tttgcgatgc cgaggtcggc ctcgtcgtct | 720 |
| tctccagcac cggccgcctg tatcacttcg ctagcaccag catggaatct gtgattgaaa | 780 |
| gatacgagga aagagagggg caccatcaga ctatgagcgc aagtgctgag gccaagcttt | 840 |
| ggcaaaggga ggcaggaagc ttgaggcagc aactgcataa cttgcaagag caccatcgga | 900 |
| agttgttggg tcagcagctc tctggcctgg acgtgagaga tttgcagaat ttagagaatc | 960 |
| agctggagac aagcctaaga aatattcgtc taaagatgga ccaacttatt ttttatcaga | 1020 |
| ttcaagaatt aaacaggaag ggatacctca tgcaccagga aaacatagaa ctacacaaca | 1080 |
| aagtcaacct tcttcatcaa gagaacatta aattacgtag aaaggcgtat ggacaaggag | 1140 |
| taaatgagca tccaacaagt actacagtta gacacagtat tctgaataca gagaatgaag | 1200 |
| atgttcggat caatcttgag ctgagtgtgc aaagggacaa atcagaaaca ccaagtgtag | 1260 |
| ggtga | 1265 |

<210> SEQ ID NO 60
<211> LENGTH: 1012
<212> TYPE: DNA
<213> ORGANISM: artificial sequence
<220> FEATURE:
<223> OTHER INFORMATION: expression construct P3371 (opLexA::G1760)

<400> SEQUENCE: 60

| | |
|---|---:|
| ccctaaaaaa gagaagaacc agaggagatt caattagagg ataaaattga tgggaagagg | 60 |
| gaagattgtg atccaaagga tcgatgattc aacgagtaga caagtcactt tctccaaacg | 120 |
| aagaaagggc cttatcaaga aagccaaaga gctagctatt ctctgtgatg ccgaggtcgg | 180 |
| tctcatcatc ttctctagca ccggaaagct ctatgacttt gcaagctcca gcatgaagtc | 240 |
| ggttattgat agatacaaca agagcaagat cgagcaacaa caactattga accccgcatc | 300 |
| agaagtcaag ttttggcaga gagaagctgc tgttctaaga caagaactgc atgctttgca | 360 |
| agaaaatcat cggcaaatga tgggagaaca gctaaatggt ttaagtgtta acgagctaaa | 420 |
| cagtcttgag aatcaaattg agataagttt gcgtggaatt cgtatgagaa aggaacaact | 480 |
| gttgactcaa gaaatccaag aactaagcca aagaggaat cttattcatc aggaaaacct | 540 |
| cgatttatct aggaaagtac aacggattca tcaagaaaat gtggagctct acaagaaggc | 600 |
| ttatatggca aacacaaacg ggtttacaca ccgtgaagta gctgttgcgg atgatgaatc | 660 |
| acacactcag attcggctgc aactaagcca gcctgaacat tccgattatg cactccacc | 720 |
| aagagcaaac gaataacaga gagattgaag ttggaagata ccatgatgtt gaagaacact | 780 |
| ccaaaggcct tggtttgaat aaggttcttg aactggaaac ctctatacac caagccacgt | 840 |
| acgataagca gcatggttct tctaacatag tcatattttc aatcctaaat ataattaaag | 900 |
| catatataat taaaatccgg tgttgttata ctcatcttga gtattaatat tgtacttgtt | 960 |
| tataaccata gattcgtcaa ttaatagaga aaaatcatat gaattattat cc | 1012 |

<210> SEQ ID NO 61
<211> LENGTH: 4276
<212> TYPE: DNA
<213> ORGANISM: artificial sequence
<220> FEATURE:
<223> OTHER INFORMATION: expression construct P6506

<400> SEQUENCE: 61

| | |
|---|---:|
| catgcctgca ggtccccaga ttagcctttt caatttcaga aagaatgcta acccacagat | 60 |
| ggttagagag gcttacgcag caggtctcat caagacgatc tacccgagca ataatctcca | 120 |

```
ggaaatcaaa taccttccca agaaggttaa agatgcagtc aaaagattca ggactaactg    180
catcaagaac acagagaaag atatatttct caagatcaga agtactattc cagtatggac    240
gattcaaggc ttgcttcaca aaccaaggca agtaatagag attggagtct ctaaaaaggt    300
agttcccact gaatcaaagg ccatggagtc aaagattcaa atagaggacc taacagaact    360
cgccgtaaag actggcgaac agttcataca gagtctctta cgactcaatg acaagaagaa    420
aatcttcgtc aacatggtgg agcacgacac acttgtctac tccaaaaata tcaaagatac    480
agtctcagaa gaccaaaggg caattgagac ttttcaacaa agggtaatat ccggaaacct    540
cctcggattc cattgcccag ctatctgtca ctttattgtg aagatagtgg aaaaggaagg    600
tggctcctac aaatgccatc attgcgataa aggaaaggcc atcgttgaag atgcctctgc    660
cgacagtggt cccaaagatg acccccacc cacgaggagc atcgtggaaa agaagacgt     720
tccaaccacg tcttcaaagc aagtggattg atgtgatatc tccactgacg taagggatga    780
cgcacaatcc cactatcctt cggcggccgc aagacccttc ctctatataa ggaagttcat    840
ttcatttgga gaggacacgc tcgagtataa gagctcattt ttacaacaat taccaacaac    900
aacaaacaac aaacaacatt acaattacat ttacaattac catggaagcg ttaacggcca    960
ggcaacaaga ggtgtttgat ctcatccgtg atcacatcag ccagacaggt atgccgccga   1020
cgcgtgcgga aatcgcgcag cgtttggggt tccgttcccc aaacgcggct gaagaacatc   1080
tgaaggcgct ggcacgcaaa ggcgttattg aaattgtttc cggcgcatca cgcgggattc   1140
gtctgttgca ggaagaggaa gaagggttgc cgctggtagg tcgtgtggct gccggtgaac   1200
cacttctggc gcaacagcat attgaaggtc attatcaggt cgatccttcc ttattcaagc   1260
cgaatgctga tttcctgctg cgcgtcagcg ggatgtcgat gaaagatatc ggcattatgg   1320
atggtgactt gctggcagtg cataaaactc aggatgtacg taacggtcag gtcgttgtcg   1380
cacgtattga tgacgaagtt accgttaagc gcctgaaaaa acagggcaat aaagtcgaac   1440
tgttgccaga aaatagcgag tttaaaccaa ttgtcgtaga tcttcgtcag cagagcttca   1500
ccattgaagg gctggcggtt ggggttattg caacggcga ctggctggaa ttccccaatt   1560
ttaatcaaag tgggaatatt gctgatagct cattgtcctt cactttcact aacagtagca   1620
acggtccgaa cctcataaca actcaaacaa attctcaagc gctttcacaa ccaattgcct   1680
cctctaacgt tcatgataac ttcatgaata atgaaatcac ggctagtaaa attgatgatg   1740
gtaataattc aaaaccactg tcacctggtt ggacggacca aactgcgtat aacgcgtttg   1800
gaatcactac agggatgttt aataccacta caatggatga tgtatataac tatctattcg   1860
atgatgaaga taccccacca aacccaaaaa agagtagct agagctttcg ttcgtatcat   1920
cggtttcgac aacgttcgtc aagttcaatg catcagtttc attgcgcaca caccagaatc   1980
ctactgagtt tgagtattat ggcattggga aaactgtttt tcttgtacca tttgttgtgc   2040
ttgtaattta ctgtgttttt tattcggttt tcgctatcga actgtgaaat ggaaatggat   2100
ggagaagagt taatgaatga tatggtcctt ttgttcattc tcaaattaat attatttgtt   2160
ttttctctta tttgttgtgt gttgaatttg aaattataag agatatgcaa acattttgtt   2220
ttgagtaaaa atgtgtcaaa tcgtggcctc taatgaccga agttaaatg aggagtaaaa    2280
cacttgtagt tgtaccatta tgcttattca ctaggcaaca aatatatttt cagacctaga   2340
aaagctgcaa atgttactga atacaagtat gtcctcttgt gttttagaca tttatgaact   2400
ttcctttatg taatttttcca gaatccttgt cagattctaa tcattgcttt ataattatag   2460
```

```
ttatactcat ggatttgtag ttgagtatga aatatttttt taatgcattt tatgacttgc    2520
caattgattg acaacatgca tcaatctaga acatatccat atctaatctt acctcgactg    2580
ctgtatataa aaccagtggt tatatgtcca gtactgctgt atataaaacc agtggttata    2640
tgtacagtac gtcgatcgat cgacgactgc tgtatataaa accagtggtt atatgtacag    2700
tactgctgta tataaaacca gtggttatat gtacagtacg tcgaggggat gatcaagacc    2760
cttcctctat ataaggaagt tcatttcatt tggagaggac acgctcgagt ataagagctc    2820 attttttacaa caattaccaa caacaacaaa caacaaacaa cattacaatt acatttacaa    2880
ttaccatggt gagcaagggc gaggagctgt tcaccgggt ggtgcccatc ctggtcgagc     2940
tggacggcga cgtaaacggc cacaagttca gcgtgtccgg cgagggcgag ggcgatgcca    3000
cctacggcaa gctgaccctg aagttcatct gcaccaccgg caagctgccc gtgccctggc    3060
ccaccctcgt gaccaccctg acctacggcg tgcagtgctt cagccgctac cccgaccaca    3120
tgaagcagca cgacttcttc aagtccgcca tgcccgaagg ctacgtccag gagcgcacca    3180
tcttcttcaa ggacgacggc aactacaaga cccgcgccga ggtgaagttc gagggcgaca    3240
ccctggtgaa ccgcatcgag ctgaagggca tcgacttcaa ggaggacggc aacatcctgg    3300
ggcacaagct ggagtacaac tacaacagcc acaacgtcta tatcatggcc gacaagcaga    3360
agaacggcat caaggtgaac ttcaagatcc gccacaacat cgaggacggc agcgtgcagc    3420
tcgccgacca ctaccagcag aacaccccca tcggcgacgg ccccgtgctg ctgcccgaca    3480
accactacct gagcacccag tccgccctga gcaaagaccc caacgagaag cgcgatcaca    3540
tggtcctgct ggagttcgtg accgccgccg ggatcactct cggcatggac gagctgtaca    3600
agtccggagg gatcctctag ctagagcttt cgttcgtatc atcggtttcg acaacgttcg    3660
tcaagttcaa tgcatcagtt tcattgcgca cacaccagaa tcctactgag tttgagtatt    3720
atggcattgg gaaaactgtt tttcttgtac catttgttgt gcttgtaatt tactgtgttt    3780
tttattcggt tttcgctatc gaactgtgaa atggaaatgg atgagaaga gttaatgaat    3840 gatatggtcc ttttgttcat tctcaaatta atattatttg ttttttctct tatttgttgt    3900
gtgttgaatt tgaaattata agagatatgc aaacattttg ttttgagtaa aaatgtgtca    3960
aatcgtggcc tctaatgacc gaagttaata tgaggagtaa aacacttgta gttgtaccat    4020
tatgcttatt cactaggcaa caaatatatt tcagaccta gaaaagctgc aaatgttact    4080
gaatacaagt atgtcctctt gtgttttaga catttatgaa cttcctttta tgtaattttc    4140
cagaatcctt gtcagattct aatcattgct ttataattat agttatactc atggatttgt    4200
agttgagtat gaaaatattt tttaatgcat tttatgactt gccaattgat tgacaacatg    4260
catcaatcga cctgca                                                   4276
```

<210> SEQ ID NO 62
<211> LENGTH: 56
<212> TYPE: PRT
<213> ORGANISM: artificial sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid -continued

```
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (43)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<223> OTHER INFORMATION: G1760 clade member consensus sequence

<400> SEQUENCE: 62

Gly Arg Gly Lys Ile Xaa Ile Xaa Xaa Ile Xaa Xaa Xaa Thr Ser Arg
1               5                   10                  15

Gln Val Thr Phe Ser Lys Arg Arg Xaa Gly Xaa Xaa Lys Lys Ala Xaa
            20                  25                  30

Glu Leu Xaa Ile Leu Cys Asp Ala Glu Val Xaa Xaa Xaa Xaa Phe Ser
        35                  40                  45

Xaa Thr Xaa Xaa Leu Tyr Xaa Xaa
    50                  55

<210> SEQ ID NO 63
<211> LENGTH: 12
<212> TYPE: PRT
<213> ORGANISM: artificial sequence
<220> FEATURE:
<223> OTHER INFORMATION: G1760 clade conserved subsequence

<400> SEQUENCE: 63

Ser Thr Ser Arg Gln Val Thr Phe Ser Lys Arg Arg
1               5                   10

<210> SEQ ID NO 64
<211> LENGTH: 7
<212> TYPE: PRT
<213> ORGANISM: artificial sequence
<220> FEATURE:
<223> OTHER INFORMATION: G1760 clade conserved subsequence

<400> SEQUENCE: 64

Ile Leu Cys Asp Ala Glu Val
1               5

<210> SEQ ID NO 65
<211> LENGTH: 1012
<212> TYPE: DNA
```

<213> ORGANISM: artificial sequence
<220> FEATURE:
<223> OTHER INFORMATION: P3371 (opLexA::G1760)

<400> SEQUENCE: 65

```
ccctaaaaaa gagaagaacc agaggagatt caattagagg ataaaattga tgggaagagg      60
gaagattgtg atccaaagga tcgatgattc aacgagtaga caagtcactt tctccaaacg     120
aagaaagggc cttatcaaga aagccaaaga gctagctatt ctctgtgatg ccgaggtcgg     180
tctcatcatc ttctctagca ccggaaagct ctatgacttt gcaagctcca gcatgaagtc     240
ggttattgat agatacaaca agagcaagat cgagcaacaa caactattga accccgcatc     300
agaagtcaag ttttggcaga gagaagctgc tgttctaaga caagaactgc atgctttgca     360
agaaaatcat cggcaaatga tgggagaaca gctaaatggt ttaagtgtta acgagctaaa     420
cagtcttgag aatcaaattg agataagttt gcgtggaatt cgtatgagaa aggaacaact     480
gttgactcaa gaaatccaag aactaagcca aagaggaat cttattcatc aggaaaacct     540
cgatttatct aggaaagtac aacggattca tcaagaaaat gtggagctct acaagaaggc     600
ttatatggca aacacaaacg ggtttacaca ccgtgaagta gctgttgcgg atgatgaatc     660
acacactcag attcggctgc aactaagcca gcctgaacat tccgattatg acactccacc     720
aagagcaaac gaataacaga gagattgaag ttggaagata ccatgatgtt gaagaacact     780
ccaaaggcct tggtttgaat aaggttcttg aactggaaac ctctatacac caagccacgt     840
acgataagca gcatggttct tctaacatag tcatattttc aatcctaaat ataattaaag     900
catatataat taaaatccgg tgttgttata ctcatcttga gtattaatat tgtacttgtt     960
tataaccata gattcgtcaa ttaatagaga aaaatcatat gaattattat cc            1012
```

<210> SEQ ID NO 66
<211> LENGTH: 2244
<212> TYPE: DNA
<213> ORGANISM: artificial sequence
<220> FEATURE:
<223> OTHER INFORMATION: P5290 (prSUC2::m35S::oEnh::LexAGal4(GFP))

<400> SEQUENCE: 66

```
aactaggggt gcataatgat ggaacaaagc acaaatcttt taacgcaaac taactacaac      60
cttcttttgg ggtccccatc cccgacccta atgttttgga attaataaaa ctacaatcac     120
ttaccaaaaa ataaaagttc aaggccacta taatttctca tatgaaccta catttataaa     180
taaaatctgg tttcatatta atttcacaca ccaagttact ttctattatt aactgttata     240
atggaccatg aaatcatttg catatgaact gcaatgatac ataatccact tgttttgtg      300
ggagacattt accagatttc ggtaaattgg tattccccct tttatgtgat tggtcattga     360
tcattgttag tggccagaca tttgaactcc cgttttttg tctataagaa ttcggaaaca     420
tatagtatcc tttgaaaacg gagaaacaaa taacaatgtg gacaaactag atataatttc     480
aacacaagac tatgggaatg atttacccca ctaattataa tccgatcaca aggtttcaac     540
gaactagttt tccagatatc aaccaaattt actttggaat taaactaact aaaactaat      600
tggttgttcg taaatggtgc ttttttttt tgcggatgat agtaaagggt ttatgtatt       660
ttatattatt agttatctgt tttcagtgtt atgttgtctc atccataaag tttatatgtt     720
ttttctttgc tctataactt atatatatat atgagtttac agttatattt atacatttca     780
gatacttgat cggcattttt tttggtaaaa aatatatgca tgaaaactc aagtgttct       840
tttttaagga attttaaat ggtgattata tgaatataat catatgtata tccgtatata     900
```

```
tatgtagcca gatagttaat tatttggggg atatttgaat tattaatgtt ataatattct     960
ttcttttgac tcgtctggtt aaattaaaga acaaaaaaaa cacatacttt tactgtttta    1020
aaaggttaaa ttaacataat ttattgatta caagtgtcaa gtccatgaca ttgcatgtag    1080
gttcgagact tcagagataa cggaagagat cgataattgt gatcgtaaca tccagatatg    1140 tatgttaat  tttcatttag atgtggatca gagaagataa gtcaaactgt cttcataatt    1200
taagacaacc tcttttaata ttttcccaaa acatgtttta tgtaactact ttgcttatgt    1260
gattgcctga ggatactatt attctctgtc tttattctct tcacaccaca tttaaatagt    1320
ttaagagcat agaaattaat tattttcaaa aggtgattta tatgcatgca aaatagcaca    1380
ccatttatgt ttatattttc aaattattta atacatttca atatttcata agtgtgattt    1440 ttttttttt  tgtcaatttc ataagtgtga tttgtcattt gtattaaaca attgtatcgc    1500
gcagtacaaa taaacagtgg gagaggtgaa aatgcagtta taaaactgtc caataattta    1560
ctaacacatt taaatatcta aaaagagtgt ttcaaaaaaa attcttttga aataagaaaa    1620
gtgatagata ttttacgct  ttcgtctgaa aataaaacaa taatagttta ttagaaaaat    1680
gttatcaccg aaaattattc tagtgccact cgctcggatc gaaattcgaa agttatattc    1740
tttctcttta cctaatataa aaatcacaag aaaaatcaat ccgaatatat ctatcaacat    1800
agtatatgcc cttacatatt gtttctgact tttctctatc cgaatttctc gcttcatggt    1860 tttttttaa  catattctca tttaattttc attactatta tataactaaa agatggaaat    1920
aaaataaagt gtctttgaga atcgaacgtc catatcagta agatagtttg tgtgaaggta    1980
aaatctaaaa gatttaagtt ccaaaaacag aaaataatat attacgctaa aaagaagaa     2040 aataattaaa tacaaaacag aaaaaaataa tatacgacag acacgtgtca cgaagatacc    2100
ctacgctata gacacagctc tgttttctct tttctatgcc tcaaggctct cttaacttca    2160
ctgtctcctc ttcggataat cctatccttc tcttcctata aatacctctc cactcttcct    2220
cttcctccac cactacaacc acca                                           2244
```

<210> SEQ ID NO 67
<211> LENGTH: 1643
<212> TYPE: DNA
<213> ORGANISM: artificial sequence
<220> FEATURE:
<223> OTHER INFORMATION: prAt5g52300 contains promoter fragment from
      prAt5g52300, found in Genbank acc. no. AB019226, GI:3869065)

<400> SEQUENCE: 67

```
tgatgatgat gatgaagaag agaacgaatt ttgaaattgg cggttttgaa ttttaagaa      60 attaaaaaat atccccgtc  gatttcaaga gggagatgga gataccaaag caactctcgc    120
cacttgtcgt cttttaattt taattgagta cgttatgccg tttaaatgt  tcaaaacagc    180 acacagttga tagctgaatt gattttttct tttgccgttt tgttatattt aaacaacaca    240
cagtgcattt gccaaataac tacatgatgg gccaataaac gtggaccgac taaaactaaa    300
taatagaaga tacatcgata ggcttctcta aagatcggat aaaagataat gtcgcatagc    360
cacgtagaga gcaactggct gagacgtggc aggacgaaac ggacgcatcg tacgtgtcag    420
aatcctacag aagtaaagag acagaagcca gagagaggtg gttcggccat atgtcatcgt    480
tctctctata aactttatgg aactttgttc tgattttctc agagacacga aaagaaagaa    540
aacaacacta gaacaaagag ggtttgattg attcacttga aaaagagaaa acacagcttt    600
ggaaacccta aaaagagaa  gaaccagagg agattcaatt agaggataaa attgatggga    660
```

```
agagggaaga ttgtgatcca aaggatcgat gattcaacga gtagacaagt cactttctcc      720
aaacgaagaa agggccttat caagaaagcc aagagctag ctattctctg tgatgccgag       780
gtcggtctca tcatcttctc tagcaccgga aagctctatg actttgcaag ctccagcatg     840
aagtcggtta ttgatagata caacaagagc aagatcgagc aacaacaact attgaacccc     900
gcatcagaag tcaagttttg gcagagagaa gctgctgttc taagacaaga actgcatgct    960
ttgcaagaaa atcatcggca atgatgggga gaacagctaa atggtttaag tgttaacgag    1020
ctaaacagtc ttgagaatca aattgagata agtttgcgtg gaattcgtat gagaaaggaa    1080
caactgttga ctcaagaaat ccaagaacta agccaaaaga ggaatcttat tcatcaggaa    1140
aacctcgatt tatctaggaa agtacaacgg attcatcaag aaaatgtgga gctctacaag    1200
aaggcttata tggcaaacac aaacgggttt acacaccgtg aagtagctgt tgcggatgat    1260
gaatcacaca ctcagattcg gctgcaacta agccagcctg aacattccga ttatgacact    1320
ccaccaagag caaacgaata acagagagat tgaagttgga agataccatg atgttgaaga    1380
acactccaaa ggccttggtt tgaataaggt tcttgaactg gaaacctcta tacaccaagc    1440
cacgtacgat aagcagcatg gttcttctaa catagtcata ttttcaatcc taaatataat    1500
taaagcatat ataattaaaa tccggtgttg ttatactcat cttgagtatt aatattgtac    1560
ttgtttataa ccatagattc gtcaattaat agagaaaaat catatgaatt attatccaaa    1620
aaaaaaaaaa aaaaaaaaa aaa                                              1643

<210> SEQ ID NO 68
<211> LENGTH: 1814
<212> TYPE: DNA
<213> ORGANISM: artificial sequence
<220> FEATURE:
<223> OTHER INFORMATION: prAT5G43840 contains promoter fragment from
      prAT5G43840 or prG1947, found in Genbank acc. AB026651,
      GI:4757407)

<400> SEQUENCE: 68
cgattttcga ataaattatt tgagctttcc aaactgtaat tcaagtatta ttacttatat      60
agtgttagtg tacttcaaaa gttaaagcat aaattttctt atatttgaaa tgacctcttc     120
tttacaaaat cttcttaaaa ttatgcatta tcaatatatt aattgtatat atatatataa     180
tgtataattc tgcttgtgtc gtgcttaacc gtttgatttg gtgtggttag atctggtttt    240
cccccaaccc aattcaattg aatcaaggat caatcaaatt ttcaaaggat actcttgttc    300
tctacacaaa tctttcaaag ggttccacca aaatcccat cattctgact tcagaataaa     360
caaacaaacc acgaaacgta tctctatgca ttcactacaa cgtgtcatgg gcgaaaacga    420
agcttataaa tgttggagca tagtcactaa atttataatg attaattaaa ttttagattt    480
tctgatattc atagaagaca aaagaacaca aaagtagcat cttccaatga atgtatgaca    540
ctatgatctc tcatttccat ttatagcaaa tcggctttgt ccacatcaaa gataactaat    600
aaatagactt atccaaaaca ctcaaaagca atacatttct atccaaaaat attaaacccc    660
aaaaatatag acagcataaa agcatcctca agcttcagct attcatcaca actattctct    720
cctctctctt tttttattaa aaaagctcaa atttatatag gttttttgtt cacaaaccct    780
aaaaaagaga agaaccagag gagattcaat tagaggataa aattgatggg aagagggaag    840
attgtgatcc aaaggatcga tgattcaacg agtagacaag tcactttctc caaacgaaga    900
aagggcctta tcaagaaagc caagagcta gctattctct gtgatgccga ggtcggtctc    960
```

```
atcatcttct ctagcaccgg aaagctctat gactttgcaa gctccagcat gaagtcggtt    1020
attgatagat acaacaagag caagatcgag caacaacaac tattgaaccc cgcatcagaa    1080
gtcaagtttt ggcagagaga agctgctgtt ctaagacaag aactgcatgc tttgcaagaa    1140
aatcatcggc aaatgatggg agaacagcta aatggtttaa gtgttaacga gctaaacagt    1200
cttgagaatc aaattgagat aagtttgcgt ggaattcgta tgagaaagga caactgttg     1260 actcaagaaa tccaagaact aagccaaaag aggaatctta ttcatcagga aaacctcgat    1320
ttatctagga aagtacaacg gattcatcaa gaaaatgtgg agctctacaa gaaggcttat    1380
atggcaaaca caaacgggtt tacacaccgt gaagtagctg ttgcggatga tgaatcacac    1440
actcagattc ggctgcaact aagccagcct gaacattccg attatgacac tccaccaaga    1500
gcaaacgaat aacagagaga ttgaagttgg aagataccat gatgttgaag aacactccaa    1560
aggccttggt ttgaataagg ttcttgaact ggaaacctct atacaccaag ccacgtacga    1620
taagcagcat ggttcttcta acatagtcat attttcaatc ctaaatataa ttaaagcata    1680
tataattaaa atccggtgtt gttatactca tcttgagtat taatattgta cttgtttata    1740
accatagatt cgtcaattaa tagagaaaaa tcatatgaat tattatccaa aaaaaaaaa     1800 aaaaaaaaaa aaaa                                                     1814

<210> SEQ ID NO 69
<211> LENGTH: 1725
<212> TYPE: DNA
<213> ORGANISM: artificial sequence
<220> FEATURE:
<223> OTHER INFORMATION: P28765 (SUC2::G1760)

<400> SEQUENCE: 69
atgggaagag ggaagattgt gatccaaagg atcgatgatt caacgagtag acaagtcact      60
ttctccaaac gaagaaaggg ccttatcaag aaagccaaag agctagctat tctctgtgat     120
gccgaggtcg gtctcatcat cttctctagc accggaaagc tctatgactt tgcaagctcc     180
agcatgaagt cggttattga tagatacaac aagagcaaga tcgagcaaca caactattg      240 aaccccgcat cagaagtcaa gttttggcag agagaagctg ctgttctaag acaagaactg     300
catgctttgc aagaaaatca tcggcaaatg atgggagaac agctaaatgg tttaagtgtt     360
aacgagctaa acagtcttga gaatcaaatt gagataagtt tgcgtggaat tcgtatgaga     420
aaggaacaac tgttgactca agaaatccaa gaactaagcc aaaagaggaa tcttattcat     480
caggaaaacc tcgatttatc taggaaagta caacggattc atcaagaaaa tgtggagctc     540
tacaagaagg cttatatggc aaacacaaac gggtttacac accgtgaagt agctgttgcg     600
gatgatgaat cacacactca gattcggctg caactaagcc agcctgaaca ttccgattat     660
gacactccac caagagcaaa cgaatagccc taaaaagag aagaaccaga ggagattcaa      720
ttagaggata aaattgatgg aagagggaa gattgtgatc caaggatcg atgattcaac       780 gagtagacaa gtcactttct ccaaacgaag aaagggcctt atcaagaaag ccaagagct      840 agctattctc tgtgatgccg aggtcggtct catcatcttc tctagcaccg gaaagctcta    900
tgactttgca agctccagca tgaagtcggt tattgataga caacaaga gcaagatcga     960 gcaacaacaa ctattgaacc ccgcatcaga agtcaagttt ggcagagag aagctgctgt    1020 tctaagacaa gaactgcatg ctttgcaaga aaatcatcgg caaatgatgg gagaacagct    1080
aaatggttta agtgttaacg agctaaacag tcttgagaat caaattgaga taagtttgcg    1140
tggaattcgt atgagaaagg acaactgttg gactcaagaa atccaagaac taagccaaaa    1200
```

```
gaggaatctt attcatcagg aaaacctcga tttatctagg aaagtacaac ggattcatca    1260
agaaaatgtg gagctctaca agaaggctta tatggcaaac acaaacgggt ttacacaccg    1320
tgaagtagct gttgcggatg atgaatcaca cactcagatt cggctgcaac taagccagcc    1380
tgaacattcc gattatgaca ctccaccaag agcaaacgaa taacagagag attgaagttg    1440
gaagatacca tgatgttgaa gaacactcca aaggccttgg tttgaataag gttcttgaac    1500
tggaaacctc tatacaccaa gccacgtacg ataagcagca tggttcttct aacatagtca    1560
tattttcaat cctaaatata attaaagcat atataattaa aatccggtgt tgttatactc    1620
atcttgagta ttaatattgt acttgtttat aaccatagat tcgtcaatta atagagaaaa    1680
atcatatgaa ttattatcca aaaaaaaaaa aaaaaaaaaa aaaaa                   1725
```

<210> SEQ ID NO 70  
<211> LENGTH: 922  
<212> TYPE: DNA  
<213> ORGANISM: artificial sequence  
<220> FEATURE:  
<223> OTHER INFORMATION: P5310 (prRSI1::m35S::oEnh::LexAGal4(GFP))

<400> SEQUENCE: 70

```
caatcaacta aatggacttt tcttgtgcat tggtcccatt tttacgccct aatattcgct      60
tacttgcttt tttgtatttt atttatttta gttttaattt tatctacctc caaattgata     120
gaaataatta cacttatagt cctttgaaa aattataatt atagcattca agtaaataaa     180
aatacgtatt tttagtcact ttgtaatgta taattttgag ttgaaaatgt atcaaaagta    240
aatttatatt cttaagatat ggataaagtt tacatataca ttatccgttt catacccctat   300 ttatagtatt acattgcata agttattgta gatcttgatc gaaagtatgt gatattaata    360 ctattttag aattatgtta ttctcagtta tggagtgata tttaaaatca atagtata      420 tcgataatca gatagtttaa ttcttatttt ctccatccaa tttatataat gatattataa   480
tcaattttac gaatgagatg gatatttga aattttagt ttaaaataaa ttttaaattt    540
tttgtgggtc tataaattat ctaattaaga ggtaaaatag aagtttgaa attaattatt    600 acttactaaa tatataaata tgtcattttt tcttaaactg atttagaaga aaagagtgtc   660
atatacatgg acagaacgaa tataatttga taattaaatt tgtaaagatt catagttaat   720
agggatcaaa attgcacgta tccattacta aaggtcata tttgcttcat aaaatcatc     780 aggatcaaaa atcagaattt atattatatt tgagggacta aaaatgctaa tatcacaaat   840
taaaattagt ctataaatat tcacacttta ctcttctaat tccatcaaat atttccattt    900
atcttctctt cttcttaaat at                                             922
```

<210> SEQ ID NO 71  
<211> LENGTH: 2365  
<212> TYPE: DNA  
<213> ORGANISM: artificial sequence  
<220> FEATURE:  
<223> OTHER INFORMATION: P5311 (prARSK1::m35S::oEnh::LexAGal4(GFP))

<400> SEQUENCE: 71

```
ggcgagtgat ggtatattta ttggttgggc ttaaatatat ttcagatgca aaaccatatt     60
gaatcaataa attataaata catagcttcc ctaaccactt aaaccaccag ctacaaaacc    120
aataaacccg atcaatcatt atgttttcat aggatttcct gaacatacat taaattattt   180
ttcattttct tggtgctctt ttctgtctta ttcacgtttt aatggacata atcggtttca    240
```

```
tattgtaaat ctctttaacc taacgaacaa tttaatgacc ctagtaatag gataagaagg      300
tcgtgaaaaa tgaacgagaa aaacccacc aaaacactat ataagaaaga ccgaaaaagt       360
aaaaagggtg agccataaac caaaaacctt accagatgtt gtcaaagaac aaaaatcatc      420
atccatgatt aacctacgct tcactactaa gacaaggcga ttgtgtcccg gttgaaaagg      480
ttgtaaaaca gtttgaggat gctacaaaag tggatgttaa gtatgaagcg gctaaggttt      540
tggatttggt ctaggagcac attggttaag caatatcttc ggtggagatt gagttttag       600 agatagtaga tactaattca tctatggaga catgcaaatt catcaaaatg cttggatgaa      660
ttagaaaaac taggtggaga atacagtaaa aaaattcaaa aagtgcatat tgtttggaca      720
acattaatat gtacaaatag tttacattta aatgtattat tttactaatt aagtacatat      780
aaagttgcta aactaaacta atataatttt tgcataagta aatttatcgt taaaagtttt      840
ctttctagcc actaaacaac aatacaaaat cgcccaagtc acccattaat taatttagaa      900
gtgaaaaaca aaatcttaat tatatggacg atcttgtcta ccatatttca agggctacag      960
gcctacagcc gccgaataaa tcttaccagc cttaaaccag aacaacggca aataagttca     1020
tgtggcggct ggtgatgatt cacaatttcc ccgacagttc tatgataatg aaactatata     1080
attattgtac gtacatacat gcatgcgacg aacaacactt caatttaatt gttagtatta     1140
aattacattt atagtgaagt atgttgggac gattagacgg atacaatgca cttatgttct     1200
ccggaaaatg aatcatttgt gttcagagca tgactccaag agtcaaaaaa gttattaaat     1260
ttatttgaat ttaaaactta aaaatagtgt aattttttaac cacccgctgc cgcaaacgtt     1320
ggcggaagaa tacgcggtgt taaacaattt ttgtgatcgt tgtcaaacat ttgtaaccgc     1380
aatctctact gcacaatctg ttacgtttac aatttacaag ttagtataga agaacgttcg     1440
tacctgaaga ccaaccgacc tttagttatt gaataaatga ttatttagtt aagagtaaca     1500
aaatcaatgg ttcaaatttg tttctcttcc ttacttctta aattttaatc atggaagaaa     1560
caaagtcaac ggacatccaa ttatggccta atcatctcat tctcctttca acaaggcgaa     1620
tcaaatcttc tttatacgta atatttattt gccagcctga aatgtatacc aaatcatttt     1680
taaattaatt gcctaaatta ttagaacaaa aactattagt aaataactaa ttagtcttat     1740
gaaactagaa atcgagatag tggaatatag agagacacca ttaaattcac aaaatcattt     1800
ttaaattacc taaattatta caacaaaaac tattagacag aactaagtct ataatgaaac     1860
gagagatcgt atttggaatg tagagcgaga gacaattttc aattcattga atatataagc     1920
aaaattatat agcccgtaga ctttggtgag atgaagtcta agtacaaaca actgaatgaa     1980
tttataatca ataatattga ttatattgtg attagaaaaa gaaaacaact tgcgttattt     2040
ttcaatatta ttgtgaggat taatgtgaac atggaatcgt gtttctcctg aaaaaaatat     2100
cagcatagag cttagaacaa tataaatata tccaccaaaa ataacttcaa cattttata     2160 caactaatac aaaaaaaaaa aagcaaactt tttgtatata taaataaatt tgaaaactca     2220
aaggtcggtc agtacgaata agacacaaca actactataa attagaggac tttgaagaca     2280
agtaggttaa ctagaacatc cttaatttct aaacctacgc actctacaaa agattcatca     2340
aaaggagtaa aagactaact ttctc                                          2365
```

<210> SEQ ID NO 72
<211> LENGTH: 687
<212> TYPE: DNA
<213> ORGANISM: artificial sequence
<220> FEATURE:
<223> OTHER INFORMATION: P28771 (prGmF6::G1760)

<400> SEQUENCE: 72

```
atgggaagag ggaagattgt gatccaaagg atcgatgatt caacgagtag acaagtcact    60
ttctccaaac gaagaaaggg ccttatcaag aaagccaaag agctagctat tctctgtgat   120
gccgaggtcg gtctcatcat cttctctagc accggaaagc tctatgactt tgcaagctcc   180
agcatgaagt cggttattga tagatacaac aagagcaaga tcgagcaaca caactattg    240
aaccccgcat cagaagtcaa gttttggcag agagaagctg ctgttctaag acaagaactg   300
catgctttgc aagaaaatca tcggcaaatg atgggagaac agctaaatgg tttaagtgtt   360
aacgagctaa acagtcttga gaatcaaatt gagataagtt tgcgtggaat tcgtatgaga   420
aaggaacaac tgttgactca agaaatccaa gaactaagcc aaaagaggaa tcttattcat   480
caggaaaacc tcgatttatc taggaaagta caacggattc atcaagaaaa tgtggagctc   540
tacaagaagg cttatatggc aaacacaaac gggtttacac accgtgaagt agctgttgcg   600
gatgatgaat cacacactca gattcggctg caactaagcc agcctgaaca ttccgattat   660
gacactccac caagagcaaa cgaatag                                        687
```

<210> SEQ ID NO 73
<211> LENGTH: 687
<212> TYPE: DNA
<213> ORGANISM: artificial sequence
<220> FEATURE:
<223> OTHER INFORMATION: P28778 (prCYCD3::G1760)

<400> SEQUENCE: 73

```
atgggaagag ggaagattgt gatccaaagg atcgatgatt caacgagtag acaagtcact    60
ttctccaaac gaagaaaggg ccttatcaag aaagccaaag agctagctat tctctgtgat   120
gccgaggtcg gtctcatcat cttctctagc accggaaagc tctatgactt tgcaagctcc   180
agcatgaagt cggttattga tagatacaac aagagcaaga tcgagcaaca caactattg    240
aaccccgcat cagaagtcaa gttttggcag agagaagctg ctgttctaag acaagaactg   300
catgctttgc aagaaaatca tcggcaaatg atgggagaac agctaaatgg tttaagtgtt   360
aacgagctaa acagtcttga gaatcaaatt gagataagtt tgcgtggaat tcgtatgaga   420
aaggaacaac tgttgactca agaaatccaa gaactaagcc aaaagaggaa tcttattcat   480
caggaaaacc tcgatttatc taggaaagta caacggattc atcaagaaaa tgtggagctc   540
tacaagaagg cttatatggc aaacacaaac gggtttacac accgtgaagt agctgttgcg   600
gatgatgaat cacacactca gattcggctg caactaagcc agcctgaaca ttccgattat   660
gacactccac caagagcaaa cgaatag                                        687
```

<210> SEQ ID NO 74
<211> LENGTH: 687
<212> TYPE: DNA
<213> ORGANISM: artificial sequence
<220> FEATURE:
<223> OTHER INFORMATION: P28753 (prCAB1::G1760)

<400> SEQUENCE: 74

```
atgggaagag ggaagattgt gatccaaagg atcgatgatt caacgagtag acaagtcact    60
ttctccaaac gaagaaaggg ccttatcaag aaagccaaag agctagctat tctctgtgat   120
gccgaggtcg gtctcatcat cttctctagc accggaaagc tctatgactt tgcaagctcc   180
agcatgaagt cggttattga tagatacaac aagagcaaga tcgagcaaca caactattg    240
```

```
aaccccgcat cagaagtcaa gttttggcag agagaagctg ctgttctaag acaagaactg    300
catgctttgc aagaaaatca tcggcaaatg atgggagaac agctaaatgg tttaagtgtt    360
aacgagctaa acagtcttga gaatcaaatt gagataagtt tgcgtggaat tcgtatgaga    420
aaggaacaac tgttgactca agaaatccaa gaactaagcc aaaagaggaa tcttattcat    480
caggaaaacc tcgatttatc taggaaagta caacggattc atcaagaaaa tgtggagctc    540
tacaagaagg cttatatggc aaacacaaac gggtttacac accgtgaagt agctgttgcg    600
gatgatgaat cacacactca gattcggctg caactaagcc agcctgaaca ttccgattat    660
gacactccac caagagcaaa cgaatag                                        687
```

```
<210> SEQ ID NO 75
<211> LENGTH: 16
<212> TYPE: PRT
<213> ORGANISM: artificial sequence
<220> FEATURE:
<223> OTHER INFORMATION: derived from wheat, rye, and tomato
<220> FEATURE:
<221> NAME/KEY: MISC_FEATURE
<222> LOCATION: (3)..(3)
<223> OTHER INFORMATION: Arg or Lys
<220> FEATURE:
<221> NAME/KEY: MISC_FEATURE
<222> LOCATION: (8)..(8)
<223> OTHER INFORMATION: any unknown amino acid
<220> FEATURE:
<221> NAME/KEY: MISC_FEATURE
<222> LOCATION: (11)..(11)
<223> OTHER INFORMATION: any unknown amino acid

<400> SEQUENCE: 75

Pro Lys Xaa Pro Ala Gly Arg Xaa Lys Phe Xaa Glu Thr Arg His Pro
1               5                   10                  15
```